US008669277B2

(12) United States Patent
Oberholzer et al.

(10) Patent No.: US 8,669,277 B2
(45) Date of Patent: Mar. 11, 2014

(54) SOLID FORMS OF AN AZOCYCLIC AMIDE

(75) Inventors: Matthew Richard Oberholzer, Wilmington, DE (US); Robert James Pasteris, Newark, DE (US); Rafael Shapiro, Wilmington, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 13/265,138

(22) PCT Filed: Apr. 19, 2010

(86) PCT No.: PCT/US2010/031546
§ 371 (c)(1),
(2), (4) Date: Oct. 19, 2011

(87) PCT Pub. No.: WO2010/123791
PCT Pub. Date: Oct. 28, 2010

(65) Prior Publication Data
US 2012/0034315 A1    Feb. 9, 2012

Related U.S. Application Data

(60) Provisional application No. 61/171,573, filed on Apr. 22, 2009, provisional application No. 61/311,512, filed on Mar. 8, 2010.

(51) Int. Cl.
*A61K 31/454* (2006.01)
*C07D 417/14* (2006.01)

(52) U.S. Cl.
USPC .......................................... 514/326; 546/209

(58) Field of Classification Search
USPC .......................................... 514/326; 546/209
See application file for complete search history.

(56) References Cited

U.S. PATENT DOCUMENTS

2009/0156592 A1   6/2009   Pasteris et al.
2010/0240619 A1   9/2010   Gregory et al.

FOREIGN PATENT DOCUMENTS

WO   2008/013622 A2   1/2008

OTHER PUBLICATIONS

Dean "Analytical Chemistry handbook" p. 10.24-10.26 (1995).*
Kirk-Othmer "Crystallization" Encyclopedia of Chem. Tech. p. 95-147 (2002).*
Polymorph "Chemistry Glossary" p. 1 (2013 from internet).*
Harwood et al., "Experimental Organic Chemistry—Principles and Practice", (Jan. 1, 1989), Blackwell Science, ISBN: 978-0-632-02016-4.
Anderson, "Practical Process Research and Development", (Jan. 1, 2000), pp. 223-247.

(Continued)

*Primary Examiner* — Celia Chang
(74) *Attorney, Agent, or Firm* — Renee M. Lett

(57) ABSTRACT

Disclosed are solid forms of 1-[4-[4-[5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone (Compound 1). Methods for the preparation of solid forms of Compound 1 and for the conversion of one solid form of Compound 1 into another are disclosed.
Disclosed are fungicidal compositions comprising a fungicidally effective amount of a solid form of Compound 1 and at least one additional component selected from the group consisting of surfactants, solid diluents and liquid carriers. Compositions comprising a mixture of a solid form of Compound 1 and at least one other fungicide or insecticide are also disclosed.
Also disclosed are methods for controlling plant diseases caused by fungal plant pathogens comprising applying to a plant or portion thereof, or to a plant seed, a fungicidally effective amount of a solid form of Compound 1.

12 Claims, 2 Drawing Sheets

(56) References Cited

OTHER PUBLICATIONS

Beckmann, "Seeding the Desired Polymorph: Background, Possibilities, Limitations and Case Studies", Org. Proc. Res. Dev., vol. 4, No. 5, pp. 372-383 (Aug. 26, 2000).

Caira, "Crystalline Polymorphism of Organic Compounds", Topics Cur. Chem., vol. 198, pp. 163-208 (Jan. 1, 1998).

* cited by examiner

SOLID FORMS OF AN AZOCYCLIC AMIDE

FIELD OF THE INVENTION

This invention relates to solid forms of 1-[4-[4-[5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]-ethanone and their compositions, and methods of their use as fungicides.

BACKGROUND OF THE INVENTION

The solid state of chemical compounds can be amorphous (i.e. no long-range order in the positions of atoms) or crystalline (i.e. atoms arranged in an orderly repeating pattern). While only one crystal form is known for the solid state of many compounds, polymorphs have been discovered for some compounds. The term "polymorph" refers to a particular crystal form (i.e. structure of crystal lattice) of a chemical compound that can exist in more than one crystal form in the solid state. Polymorphs can differ in such chemical and physical (i.e. physiochemical) properties as crystal shape, density, hardness, color, chemical stability, melting point, hydroscopicity, suspensibility and dissolution rate, and such biological properties as biological availability.

Predicting physiochemical properties such as melting point for a crystal form or crystal forms in which the solid state of a chemical compound can exist remains impossible. Furthermore, even predicting whether the solid state of a compound may be present in more than one crystal form is not possible.

PCT Patent Publication WO 08/013,925 discloses the fungicidal azocyclic amide 1-[4-[4-[5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone and methods for its preparation, as well as the utility of this compound as a fungicide. New solid forms of this compound, their compositions and methods of their preparation and use have now been discovered.

SUMMARY OF THE INVENTION

This invention relates to solid forms of 1-[4-[4-[5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]-ethanone (Compound 1). More particularly, this invention is directed to a crystalline polymorph of Compound 1 designated Form B characterized by a powder X-ray diffraction pattern having at least the 2θ reflection positions 14.902, 18.123, 18.87, 20.204, 20.883, 21.79, 24.186 and 26.947.

This invention also relates to methods for the direct preparation of various solid forms of Compound 1 (i.e. not starting with other solid forms of Compound 1). More particularly, this invention is directed to a method for preparing a desired crystalline polymorph of Compound 1 comprising: forming a reaction mixture by contacting 2-bromo-1-[4,5-dihydro-5-(2,6-difluorophenyl)-3-isoxazolyl]ethanone and 1-[2-[5-methyl-3-(trifluoromethyl)-1H-pyrazol-1-yl]acetyl]-4-piperidinecarbothioamide in the presence of an alkanol solvent; neutralizing the reaction mixture with base; and adding water and seed crystals of the desired crystalline polymorph to the reaction mixture. This invention also relates to methods for the conversion of one solid form of Compound 1 into another. More particularly, this invention is directed to a method for preparing a crystalline polymorph of Compound 1 designated Form B, the method comprising: mixing a crystalline polymorph of Compound 1 designated Form A characterized by a powder X-ray diffraction pattern having at least the 2θ reflection positions 13.321, 17.353, 17.563, 19.329, 22.93, 24.326, 25.852 and 26.792 with a solvent comprising an alkanol to form a slurry; adding seed crystals of polymorph Form B to the slurry; and maintaining the slurry while the polymorph Form A converts to polymorph Form B.

This invention also relates to a fungicidal composition comprising (a) at least one solid form of Compound 1; and (b) at least one additional component selected from the group consisting of surfactants, solid diluents and liquid carriers.

This invention also relates to a fungicidal composition comprising (a) at least one solid form of Compound 1; and (b) at least one other fungicide (e.g., at least one other fungicide having a different site of action) and/or insecticide.

This invention further relates to a method for controlling plant diseases caused by fungal plant pathogens comprising applying to a plant or portion thereof, or to a plant seed, a fungicidally effective amount of at least one solid form of Compound 1 (e.g., as a composition described herein).

DETAILED DESCRIPTION OF THE INVENTION

Figure 1:
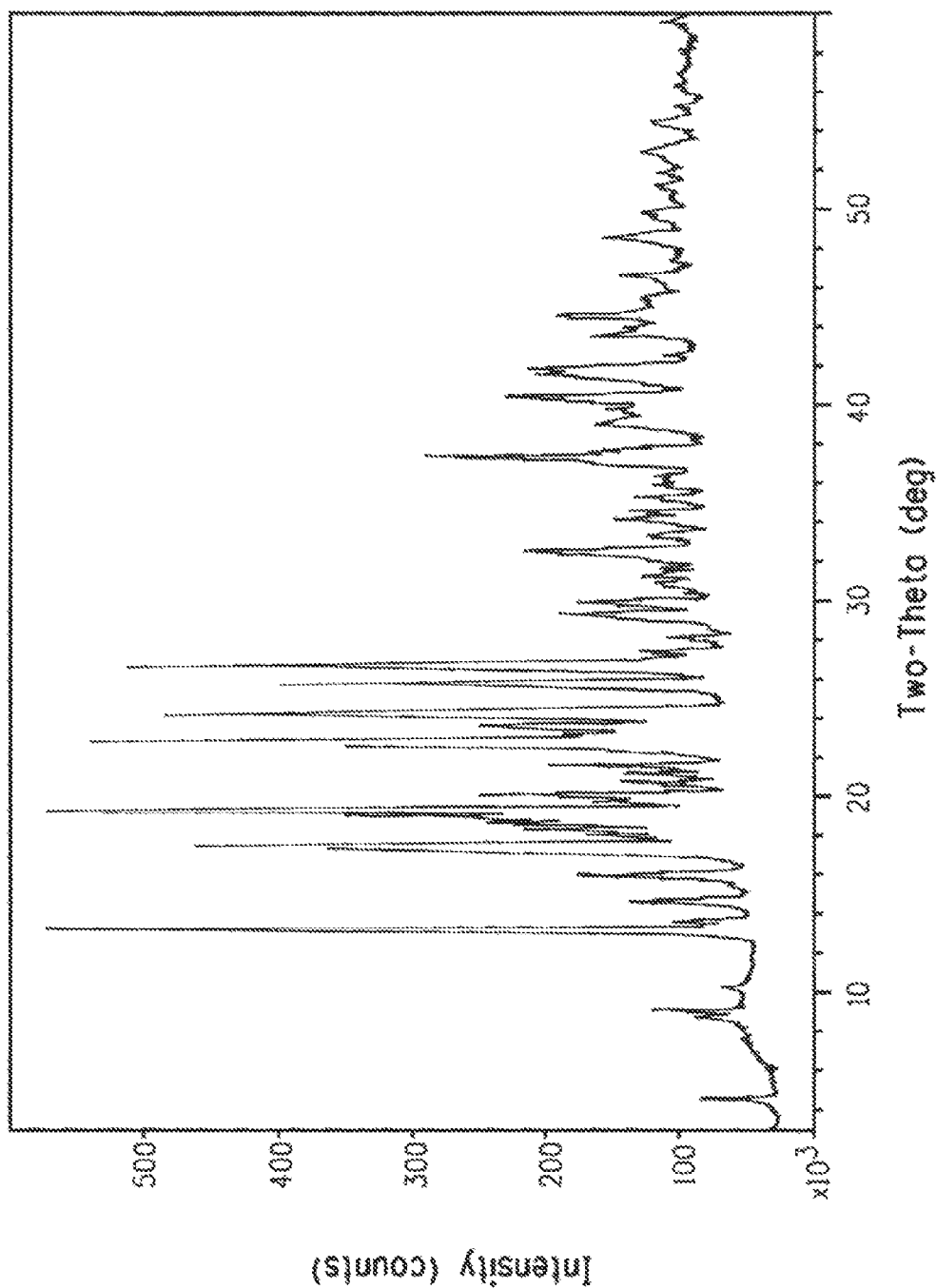
FIG. 1 is a powder X-ray diffraction pattern of polymorph crystal Form A of Compound 1 showing absolute intensity count graphed against 2θ reflection positions.

As used herein, the terms "comprises," "comprising," "includes," "including," "has," "having", "contains" or "containing" or any other variation thereof, are intended to cover a non-exclusive inclusion. For example, a composition, process, method, article, or apparatus that comprises a list of elements is not necessarily limited to only those elements but may include other elements not expressly listed or inherent to such composition, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

As referred to in the present disclosure and claims, "plant" includes members of Kingdom Plantae, particularly seed plants (Spermatopsida), at all life stages, including young plants (e.g., germinating seeds developing into seedlings) and mature, reproductive stages (e.g., plants producing flowers and seeds). Portions of plants include geotropic members typically growing beneath the surface of the growing medium (e.g., soil), such as roots, tubers, bulbs and corms, and also members growing above the growing medium, such as foliage (including stems and leaves), flowers, fruits and seeds.

As referred to herein, the term "seedling", used either alone or in a combination of words means a young plant developing from the embryo of a seed.

The term "water-miscible" in the context of "water-miscible solvent" means a liquid solvent (including mixtures of solvent compounds) that is completely soluble in water (and water soluble in the solvent) in all proportions at the temperature of the (e.g., reaction) medium comprising the water-miscible solvent. Methanol, ethanol, acetone and acetonitrile are examples of water-miscible solvents.

Conversely, the term "water-immiscible" in the context of a substance that is a "water-immiscible organic compound", "water-immiscible liquid component" or "water-immiscible liquid carrier" denotes that the substance is not soluble in water (and water soluble in the substance) in all proportions at relevant temperatures (for formulated compositions around room temperature, e.g. about 20° C.). Typically water-immiscible substances used as liquid carriers or other liquid components in formulated compositions have little water solubility and water has little solubility in the water-immiscible substances. Often water-immiscible substances used in formulation are soluble in water in an extent of less than about 1%, or less than about 0.1%, or even less than about 0.01% by weight at about 20° C.

The expression "continuous liquid phase" in the context of liquid formulated compositions refers to the liquid phase formed by the liquid carrier. The continuous liquid phase provides the bulk liquid medium in which other formulating components are dissolved, dispersed (as solid particulates) or emulsified (as liquid droplets). When the liquid carrier is aqueous (water optionally containing dissolved water-soluble compounds), a liquid emulsified in the aqueous liquid carrier is formed by a water-immiscible liquid component.

Embodiments of the present invention include:

Embodiment 1. The crystalline polymorph of 1-[4-[4-[5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone (Compound 1) designated Form A in the Summary of the invention and characterized by powder X-ray diffraction pattern having at least the 2θ reflection positions

| 2θ |
|---|
| 13.321 |
| 17.353 |
| 17.563 |
| 19.329 |
| 22.93 |
| 24.326 |
| 25.852 |
| 26.792. |

Embodiment 2. The crystalline polymorph of 1-[4-[4-[5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone (Compound 1) designated Form B in the Summary of the Invention and characterized by powder X-ray diffraction pattern having at least the 2θ reflection positions

| 2θ |
|---|
| 14.902 |
| 18.123 |
| 18.87 |
| 20.204 |
| 20.883 |
| 21.79 |
| 24.186 |
| 26.947. |

Embodiment 3. The method described in Summary of the invention for preparing a desired crystalline polymorph of Compound 1 comprising forming a reaction mixture prepared by contacting 2-bromo-1-[4,5-dihydro-5-(2,6-difluorophenyl)-3-isoxazolyl]ethanone and 1-[2-[5-methyl-3-(trifluoromethyl)-1H-pyrazol-1-yl]acetyl]-4-piperidinecarbothioamide in the presence of an alkanol solvent; neutralizing the reaction mixture with base; and adding water and seed crystals of the desired crystalline polymorph to the reaction mixture.

Embodiment 4. The method of Embodiment 3 wherein the reaction mixture is formed by contacting 2-bromo-1-[4,5-dihydro-5-(2,6-difluorophenyl)-3-isoxazolyl]ethanone and 1-[2-[5-methyl-3-(trifluoromethyl)-1H-pyrazol-1-yl]acetyl]-4-piperidinecarbothioamide in a molar ratio ranging from about 1.2:1 to about 1:1.2.

Embodiment 5. The method of Embodiment 4 where the molar ratio is about 1:1.

Embodiment 6. The method of any one of Embodiments 3 through 5 wherein the alkanol solvent is selected from lower alkanols (i.e. $C_1$-$C_4$ alkanols) (including mixtures thereof).

Embodiment 7. The method of Embodiment 6 wherein the alkanol solvent is selected from methanol and ethanol (including mixtures thereof).

Embodiment 8. The method of any one of Embodiments 3 through 7 wherein the 2-bromo-1-[4,5-dihydro-5-(2,6-difluorophenyl)-3-isoxazolyl]ethanone and 1-[2-[5-methyl-3-(trifluoromethyl)-1H-pyrazol-1-yl]acetyl]-4-piperidinecarbothioamide are contacted in the presence of the alkanol solvent at a reaction temperature of at least about 20° C.

Embodiment 9. The method of Embodiment 8 wherein the reaction temperature is at least about 45° C.

Embodiment 10. The method of any one of Embodiments 3 through 9 wherein the 2-bromo-1-[4,5-dihydro-5-(2,6-difluorophenyl)-3-isoxazolyl]ethanone and 1-[2-[5-methyl-3-(trifluoromethyl)-1H-pyrazol-1-yl]acetyl]-4-piperidinecarbothioamide are contacted in the presence of the alkanol solvent at a reaction temperature of no more than about 60° C.

Embodiment 11. The method of Embodiment 10 wherein the reaction temperature is no more than about 55° C.

Embodiment 12. The method of any one of Embodiments 3 through 11 wherein the base comprises an alkali metal salt of carbonic acid or a carboxylic acid.

Embodiment 13. The method of Embodiment 12 wherein the base comprises sodium acetate or sodium bicarbonate.

Embodiment 14. The method of Embodiment 13 wherein the base comprises sodium acetate.

Embodiment 15. The method of any one of Embodiments 3 through 14 wherein at least about 1 equivalent of the base (relative to the reactant selected from 2-bromo-1-[4,5-dihydro-5-(2,6-difluorophenyl)-3-isoxazolyl]ethanone and 1-[2-[5-methyl-3-(trifluoromethyl)-1H-pyrazol-1-yl]acetyl]-4-piperidinecarbothioamide that is in lesser molar amount) is added to neutralize the reaction mixture.

Embodiment 16. The method of any one of Embodiments 3 through 15 wherein no more than about 1.5 equivalents of the base is added to neutralize the reaction mixture.

Embodiment 17. The method of any one of Embodiments 3 through 16 comprising an additional step wherein a second alkanol solvent is added to the reaction mixture after the step of contacting 2-bromo-1-[4,5-dihydro-5-(2,6-difluorophenyl)-3-isoxazolyl]ethanone and 1-[2-

[5-methyl-3-(trifluoromethyl)-1H-pyrazol-1-yl]acetyl]-4-piperidinecarbothioamide in the presence of the (first) alkanol solvent and before the step of neutralizing the reaction mixture with base.

Embodiment 18. The method of any one of Embodiments 3 through 17 wherein the water is added in an amount of at least about 5% of the volume of the alkanol solvent or solvents forming the reaction mixture.

Embodiment 19. The method of Embodiment 18 wherein the water is added in an amount of at least about 10% of the volume of the alkanol solvent or solvents forming the reaction mixture.

Embodiment 20. The method of any one of Embodiments 3 through 19 wherein the water is added in an amount up to about 50% of the volume of the alkanol solvent or solvents forming the reaction mixture.

Embodiment 21. The method of Embodiment 20 wherein the water is added in an amount up to about 40% of the volume of the alkanol solvent or solvents forming the reaction mixture.

Embodiment 22. The method of Embodiment 21 wherein the water is added in an amount up to about 30% of the volume of the alkanol solvent or solvents forming the reaction mixture.

Embodiment 23. The method of Embodiment 22 wherein the water is added in an amount up to about 25% of the volume of the alkanol solvent or solvents forming the reaction mixture.

Embodiment 24. The method of any one of Embodiments 3 through 23 comprising after adding the water and the seed crystals to the reaction mixture the additional step of cooling the reaction mixture to a temperature below about 40° C.

Embodiment 25. The method of Embodiment 24 wherein after adding the water and the seed crystals to the reaction mixture the reaction mixture is cooled to a temperature below about 30° C.

Embodiment 26. The method of any one of Embodiments 3 through 25 wherein the seed crystals are polymorph Form A of Embodiment 1.

Embodiment 27. The method of any one of Embodiments 3 through 25 wherein the seed crystals are polymorph Form B of Embodiment 2.

Embodiment 27a. The method of any one of Embodiments 3 through 27a wherein the reaction mixture is agitated after adding the seed crystals.

Embodiment 27b. The method of Embodiment 27a wherein the reaction mixture is agitated by stirring after adding the seed crystals.

Embodiment 28. The method described in Summary of the invention for preparing the polymorph Form B of Embodiment 2 comprising mixing the polymorph Form A of Embodiment 1 with a solvent comprising an alkanol to form a slurry; adding seed crystals of the polymorph Form B to the slurry; and maintaining the slurry while the polymorph Form A converts to polymorph Form B.

Embodiment 29. The method of Embodiment 28 wherein at least about 5% by volume (relative to the volume of components other than water in the solvent comprising an alkanol) of water is added to the solvent comprising an alkanol.

Embodiment 30. The method of Embodiment 29 wherein at least about 10% by volume of water is added to the solvent comprising an alkanol.

Embodiment 31. The method of Embodiment 30 wherein at least about 20% by volume of water is added to the solvent comprising an alkanol.

Embodiment 32. The method of any one of Embodiments 28 through 31 wherein no more than about 50% by volume (relative to the volume of components other than water in the solvent comprising an alkanol) of water is added to the solvent comprising an alkanol.

Embodiment 33. The method of Embodiment 32 wherein no more than about 40% by volume of water is added to the solvent comprising an alkanol.

Embodiment 34. The method of Embodiment 33 wherein no more than about 30% by volume of water is added to the solvent comprising an alkanol.

Embodiment 35. The method of any one of Embodiments 29 through 34 wherein the solvent comprising an alkanol contains no more than about 5% by volume of water before the water is added.

Embodiment 36. The method of any one of Embodiments 29 through 35 wherein the solvent comprising an alkanol that is mixed with Polymorph Form A consists essentially of one or more alkanols and optionally water (and optionally containing dissolved Compound 1).

Embodiment 36a. The method of Embodiments 28 through 36 wherein the slurry consists essentially of Compound 1 (in one or more solid forms or dissolved) and one or more alkanols, and optionally water.

Embodiment 36b. The method of any one of Embodiments 28 through 36a wherein the alkanol is selected from lower alkanols (i.e. $C_1$-$C_4$ alkanols) (including mixtures thereof).

Embodiment 36c. The method of Embodiment 36b wherein the alkanol is selected from methanol and ethanol (including mixtures thereof).

Embodiment 36d. The method of Embodiment 36c wherein the alkanol is methanol.

Embodiment 36e. The method of any one of Embodiments 28 through 36a wherein the slurry consists essentially of Compound 1 with methanol or with methanol and water, or consists essentially of a mixture of Compound 1 with ethanol or with ethanol and water.

Embodiment 37. The method of any one of Embodiments 28 through 36e wherein the slurry is maintained at a temperature of at least about 20° C. before the step adding the seed crystals of the polymorph Form B and then continuing during the step of maintaining the slurry while the polymorph Form A converts to polymorph Form B.

Embodiment 38. The method of Embodiment 37 wherein the slurry is maintained at a temperature of at least about 30° C. before the step adding the seed crystals of the polymorph Form B and then continuing during the step of maintaining the slurry while the polymorph Form A converts to polymorph Form B.

Embodiment 39. The method of Embodiment 38 wherein the slurry is maintained at a temperature of at least about 40° C. before the step adding the seed crystals of the polymorph Form B and then continuing during the step of maintaining the slurry while the polymorph Form A converts to polymorph Form B.

Embodiment 40. The method of Embodiment 39 wherein the slurry is maintained at a temperature of at least about 50° C. before the step adding the seed crystals of the polymorph Form B and then continuing during the step of maintaining the slurry while the polymorph Form A converts to polymorph Form B.

Embodiment 41. The method of any one of Embodiments 28 through 40 wherein the slurry is maintained at a temperature of no more than about 100° C. before the step adding the seed crystals of the polymorph Form B and then continuing during the step of maintaining the slurry while the polymorph Form A converts to polymorph Form B.

Embodiment 42. The method of Embodiment 41 wherein the slurry is maintained at a temperature of no more than about 80° C. before the step adding the seed crystals of the polymorph Form B and then continuing during the step of maintaining the slurry while the polymorph Form A converts to polymorph Form B.

Embodiment 43. The method of Embodiment 42 wherein the slurry is maintained at a temperature of no more than about 60° C. before the step adding the seed crystals of the polymorph Form B and then continuing during the step of maintaining the slurry while the polymorph Form A converts to polymorph Form B.

Embodiment 44. The method of any one of Embodiments 28 through 43 wherein the slurry is agitated during the step of maintaining the slurry while the polymorph Form A converts to polymorph Form B.

Embodiment 45. The method of Embodiment 44 wherein the slurry is stirred to agitate the slurry.

Embodiment 46. The method of any one of Embodiments 28 through 45 further comprising the additional step of collecting the polymorph Form B (after maintaining the slurry while the polymorph Form A converts to the polymorph Form B).

Embodiment 47. A method of any one of Embodiments 28 through 46 wherein the polymorph Form A mixed with the alkanol solvent is in admixture with the polymorph Form B.

Embodiment 48. A fungicidal composition comprising (a) at least one solid form of 1-[4-[4-[5-(2,6-difluorophenyl)-4,5-dihydro-3-isoxazolyl]-2-thiazolyl]-1-piperidinyl]-2-[5-methyl-3-(trifluoromethyl)-1H-pyrazol-yl]ethanone; and (b) at least one additional component selected from the group consisting of surfactants, solid diluents, and liquid carriers.

Embodiment 49. The composition of Embodiment 48 wherein component (a) comprises polymorph Form A of Embodiment 1.

Embodiment 50. The composition of Embodiment 48 wherein component (a) comprises polymorph Form B of Embodiment 2.

Embodiment 51. The composition of Embodiment 50 comprising a liquid carrier forming a continuous liquid phase in which component (a) is dispersed.

Embodiment 52. The composition of Embodiment 51 wherein the liquid carrier forming the continuous liquid phase comprises water (i.e. the liquid carrier is an aqueous liquid carrier).

Embodiment 53. The composition of Embodiment 52 wherein water is at least about 50% by weight of the liquid carrier forming the continuous liquid phase.

Embodiment 54. The composition of Embodiment 53 wherein water is at least about 60% by weight of the liquid carrier forming the continuous liquid phase.

Embodiment 55. The composition of Embodiment 54 wherein water is at least about 70% by weight of the liquid carrier forming the continuous liquid phase.

Embodiment 56. The composition of Embodiment 55 wherein water is at least about 80% by weight of the liquid carrier forming the continuous liquid phase.

Embodiment 57. The composition of Embodiment 56 wherein water is at least about 90% by weight of the liquid carrier forming the continuous liquid phase.

Embodiment 58. The composition of any one of Embodiments 50 through 57 comprising:
(a) from about 1 to about 25% of polymorph Form B of Embodiment 2;
(b1) from about 50 to about 70% of water;
(b2) from about 0.5 to about 10% of a surfactant component having a dispersant property; and
(c) from about 0.1 to about 5% of a suspending agent component;
by weight based on the total weight of the composition.

Embodiment 59. The composition of Embodiment 58 wherein component (b2) (i.e. the surfactant component having a dispersing property) comprises at least one dispersing agent selected from the group consisting of alkoxylated alcohols, methyl methacrylate graft copolymers, block copolymers based on poly-12-hydroxystearic acid and polyethylene glycol and polyethylene oxide-polypropylene oxide block copolymers.

Embodiment 60. The composition of any one of Embodiments 51 through 59 containing less than about 5% by weight of water-immiscible organic compounds in a liquid phase.

Embodiment 61. The composition of Embodiment 60 containing less than about 1% by weight of water-immiscible organic chemical compounds in a liquid phase.

Embodiment 62. The composition of any one of Embodiments 51 through 61 wherein the continuous liquid phase is the only liquid phase in the composition (i.e. the composition is a single-liquid phase composition).

Embodiment 63. The composition of any one of Embodiments 52 through 57 farther comprising a water-immiscible liquid component.

Embodiment 64. The composition of Embodiment 63 wherein the water-immiscible liquid component is emulsified in the continuous liquid phase.

Embodiment 65. The composition of Embodiment 63 or 64 comprising:
(a) from about 10 to about 25% of polymorph Form B of Embodiment 2;
(b1) from about 30 to about 50% of water;
(b2) from about 5 to about 20% of a surfactant component having a dispersant property; and
(c) from about 0.1 to about 5% of a suspending agent component; and
(d) from about 5 to about 40% of the water-immiscible liquid component;
by weight based on the total weight of the composition.

Embodiment 66. The composition of Embodiment 65 wherein component (b2) (i.e. the surfactant component having a dispersant property) also has an emulsifier property.

Embodiment 67. The composition of any one of Embodiments 63 through 66 wherein the water-immiscible liquid component (i.e. component (d)) comprises at least one substance selected from glycerol esters of fatty acids, lower alkyl esters of fatty acids and mineral oils.

Embodiment 68. The composition of Embodiment 67 wherein component (d) comprises at least one substance selected from methyl esters of fatty acids and medium ($C_7$ to $C_9$) chain glycerol esters of fatty acids.

Embodiment 69. The composition of any one of Embodiments 65 through 68 wherein component (b2) comprises at least one substance selected from the group consisting of calcium dodecylbenzene sulfonates, ethoxylated tallowamine sulfates, ethoxylated non-ionic surfactants (e.g. ethoxylated castor oil and ethoxylated tristyrlphenols), fatty acid hexaesters of ethoxylated sorbitol, alkyl polyglycosides, block copolymers based on poly-12-hydroxystearic acid and polyethylene glycol, alkoxylated alcohols and polyethylene oxide-polypropylene oxide block copolymers Embodiment 69a. The composition of any one of Embodiments 65 through 68 wherein component (b2) comprises at least one substance selected from the group consisting of calcium dodecylbenzene sulfonates, ethoxylated tallowamine sulfates, ethoxylated non-ionic surfactants (e.g. ethoxylated castor oil and ethoxylated tristyrlphenols), block copolymers based on poly-12-hydroxystearic acid and polyethylene glycol, alkoxylated alcohols and polyethylene oxide-polypropylene oxide block copolymers Embodiment 70. The composition of any one of Embodiments 63 through 69 further comprising an antifoam component in an amount of from about 0.01% to about 5% by weight of the composition.

Embodiment 71. The composition of any one of Embodiments 63 through 70 further comprising a biocide component in an amount of from about 0.001% to about 1% by weight of the composition.

Embodiment 72. The composition of any one of Embodiments 63 through 71 further comprising an antifreeze component in an amount of from about 1% to about 10% by weight of the composition.

Embodiment 73. The composition of any one of Embodiments 63 through 62 further comprising a pH-buffer component in an amount of from about 0.1% to about 10% of the composition by weight.

Embodiment 74. The composition of Embodiment 51 wherein the liquid carrier forming the continuous liquid phase is water-immiscible.

Embodiment 75. The composition of Embodiment 74 wherein the composition contains not more than about 10% water by weight.

Embodiment 76. The composition of Embodiment 75 wherein the composition contains not more than about 5% water by weight.

Embodiment 77. The composition of any one of Embodiments 74 through 76 comprising:
(a) from about 1 to about 20% of polymorph Form B of Embodiment 2;
(b1) from about 10 to about 60% of the water-immiscible liquid component;
(b2) from about 2 to about 15% of a surfactant component having a dispersing property; and
(c) from about 0.1 to about 10% of a suspending agent component;
by weight based on the total weight of the composition.

Embodiment 78. The composition of Embodiment 77 wherein component (b2) (i.e. the surfactant component having a dispersant property) also has an emulsifier property.

Embodiment 79. The composition of Embodiment 77 or 78 further comprising water in an amount of from about 0.1 to about 5% by weight.

Embodiment 80. The composition of any one of Embodiments 77 through 79 wherein component (b1) comprises at least one substance selected from the group consisting of medium ($C_7$ to $C_9$) chain glycerol esters of fatty acids, lower alkyl esters of fatty acids and mineral oils.

Embodiment 81. The composition of any one of Embodiments 77 through 80 wherein component (b2) comprises at least one substance selected from the group consisting of calcium dodecylbenzene sulfonates, ethoxylated tallowamine sulfates, ethoxylated non-ionic surfactants (e.g. ethoxylated castor oil and ethoxylated tristyrlphenols), alkyl polyglycosides, fatty acid hexaesters of ethoxylated sorbitol, fatty acid triesters of sorbitan and polyethylene glycol alkyd resins.

Embodiment 81a. The composition of any one of Embodiments 77 through 80 wherein component (b2) comprises at least one substance selected from the group consisting of calcium dodecylbenzene sulfonates, ethoxylated tallowamine sulfates, ethoxylated non-ionic surfactants (e.g. ethoxylated castor oil and ethoxylated tristyriphenols) and polyethylene glycol alkyd resins.

Embodiment 82. The composition of any one of Embodiments 77 through 81 wherein component (c) comprises at least one substance selected from the group consisting of fumed silica, organically modified silicas and organically modified bentonite clays.

Embodiment 83. The composition of any one of Embodiments 48 through 82 wherein the composition further comprises one or more additional active ingredients selected from fungicides and insecticides.

Embodiment 84. The composition of Embodiment 83 wherein the one or more additional active ingredients are in an amount of from 0.1 to about 40% by weight of the composition.

Embodiments of this invention, including Embodiments 1-84 above as well as any other embodiments described herein, can be combined in any manner.

Compound 1 is 1-[4-[4-[5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone and has the following molecular structure:

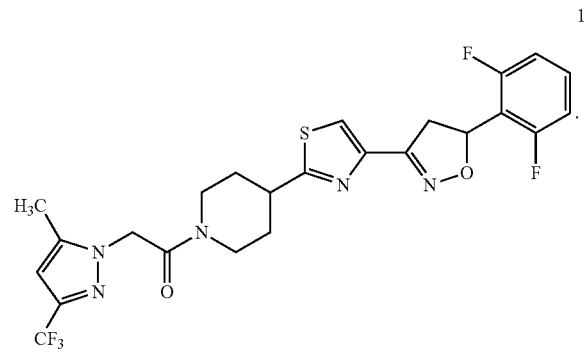 [SMILES: Cc1cc(C(F)(F)F)nn1CC(=O)N1CCC(c2nc(C3=NOC(c4c(F)cccc4F)C3)cs2)CC1]

The molecular structure of Compound 1 can exist as two distinct stereoisomers (i.e. enantiomers). However, the present invention relates to a racemic mixture of Compound 1 comprising equal amounts of the two possible enantiomers.

The solid state of Compound 1 has now been discovered to be preparable in more than one solid form. These solid forms include an amorphous solid form, in which there is no long-range order in the positions of molecules (e.g., foams and glasses). These solid forms also include crystalline forms, in which constituent molecules are arranged in an orderly repeating pattern extending in all three spatial dimensions. The term "polymorph" refers to a particular crystalline form of a chemical compound that can exist in more than one crystal structure (e.g. lattice type) in the solid state. The term "packing polymorphs" refers to particular crystalline forms of a compound having different crystal packing. Crystalline forms of Compound 1 in this invention relate to embodiments which include a single polymorph (i.e. single crystalline form) and to embodiments which include a mixture of polymorphs (i.e. different crystalline forms). Polymorphs can differ in such chemical, physical and biological properties as crystal shape, density, hardness, color, chemical stability, melting point, hygroscopicity, suspensibility, dissolution rate and biological availability. One skilled in the art will appreciate that a polymorph of Compound 1 can exhibit beneficial effects (e.g., suitability for preparation of useful formulations, improved biological performance) relative to another polymorph or a mixture of polymorphs of Compound 1. Differences with respect to chemical stability, filterability, solubility, hygroscopicity, melting point, solid density and flowability can have a significant effect on the development of production methods and formulations, and the quality and efficacy of plant treatment agents. Preparation and isolation of particular polymorphs of Compound 1 has now been achieved.

One crystalline polymorph form of Compound 1 is designated as Form A. This solid form is unsolvated and racemic. Form A can be characterized by X-Ray powder diffraction (XRPD), single crystal X-Ray structure analysis and Differential Scanning Calorimetry (DSC).

The powder X-ray diffraction pattern of polymorph Form A of Compound 1 is shown in FIG. 1. The corresponding 2θ values are tabulated in Table 1 of Characterization Example 1. Polymorph Form A of Compound 1 can be identified by a powder X-ray diffraction pattern having at least the 2θ reflection positions

| 2θ |
|---|
| 13.321 |
| 17.353 |
| 17.563 |
| 19.329 |
| 22.93 |
| 24.326 |
| 25.852 |
| 26.792. |

Single crystal X-ray diffraction can also be used to characterize polymorph Form A. A full description of single crystal X-ray diffraction of polymorph Form A is provided in Characterization Example 2. Crystals of polymorph Form A have a triclinic unit cell and typically exhibit a needle-like morphology.

Polymorph Form A of Compound 1 can also be characterized by Differential Scanning Calorimetry. DSC indicates the melting point of polymorph Form A is about 127° C. The details of a DSC experiment are provided in Characterization Example 3. Polymorph Form A is physically stable and non-hydrated in its pure solid form (shown in Characterization Example 4).

Polymorph Form A of Compound 1 can be prepared by dissolving the amorphous solid form of Compound 1 in a solvent at room temperature (illustrated in Preparation Example 1) or near the boiling point of the solvent and then cooling back to room temperature or lower. Methanol, ethanol or mixtures of methanol and water are particularly useful solvents for this method. Polymorph Form A can also be prepared directly during the preparation of Compound 1 (see Preparation Examples 1 and 2).

A second crystalline polymorph form of Compound 1, designated as Form B, was originally isolated from a solubility/MSZW (metastable zone width) determination experiment for crystal Form A (see Preparation Example 3). This solid form is unsolvated and racemic. Polymorph Form B can be characterized by X-Ray powder diffraction, single crystal X-Ray structure analysis and Differential Scanning Calorimetry.

Figure 2:
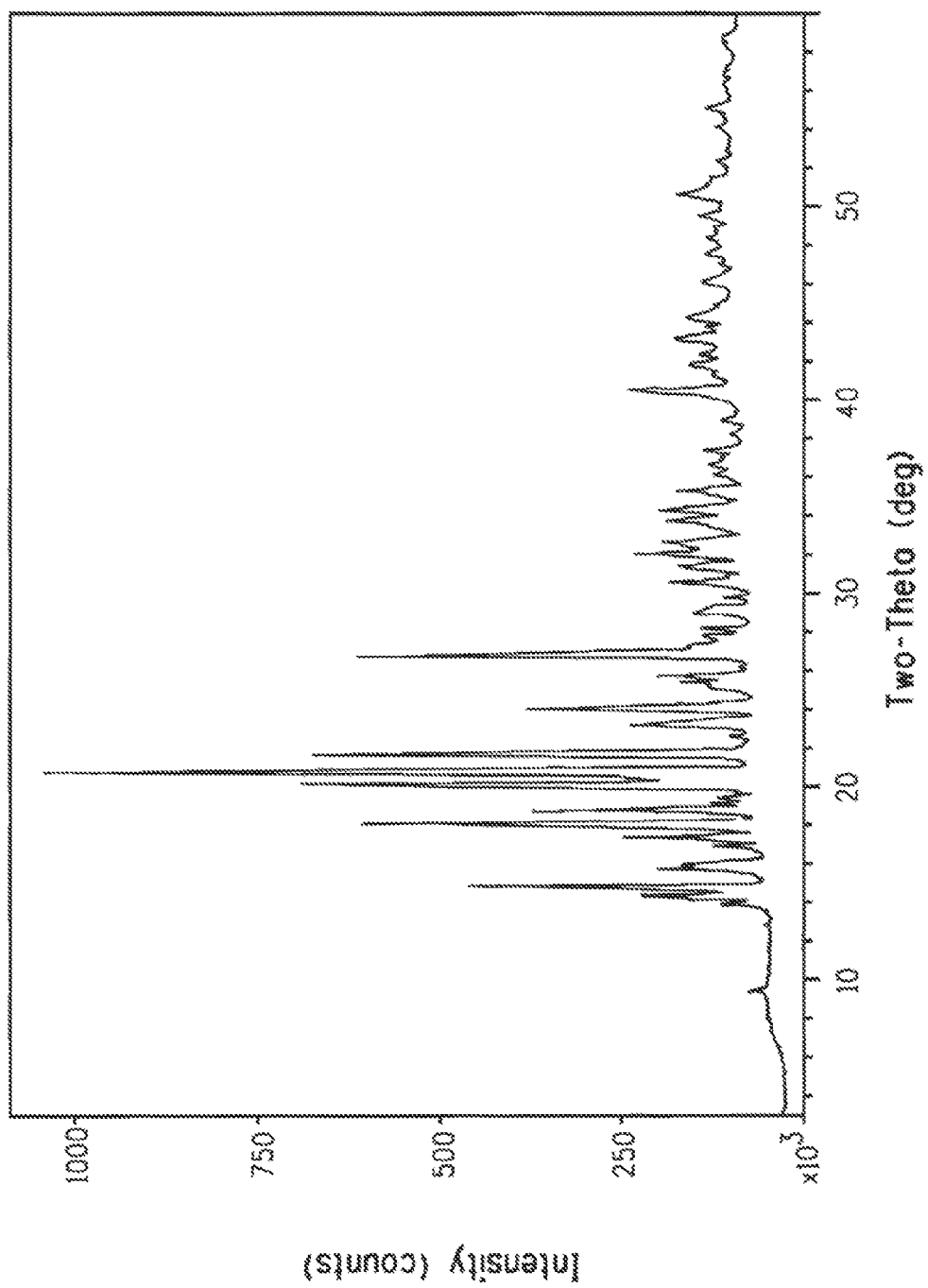
FIG. 2 is a powder X-ray diffraction pattern of polymorph crystal Form B of Compound 1 showing absolute intensity count graphed against 2θ reflection positions.

The powder X-ray diffraction pattern of polymorph Form B of Compound 1 is shown in FIG. 2. The corresponding 2θ values are tabulated in Table 2 of Characterization Example 1. Polymorph Form B of Compound 1 can be identified by a powder X-ray diffraction pattern having at least the 2θ reflection positions

| 2θ |
|---|
| 14.902 |
| 18.123 |
| 18.87 |
| 20.204 |
| 20.883 |
| 21.79 |
| 24.186 |
| 26.947. |

Single crystal X-ray diffraction can also be used to characterize polymorph Form B. A full description of single crystal X-ray diffraction of polymorph Form B is provided in Characterization Example 5. Crystals of polymorph Form B have an orthorhombic unit cell and typically exhibit a blade-like morphology.

Single crystal X-ray diffraction shows polymorph Forms A and B are packing polymorphs that contain primarily different molecular conformations of Compound 1. Form A typically contains one molecular conformation and Form B typically is composed of a mixture of about 71% of one conformation and about 29% of another conformation. The minor molecular conformation in Form B resembles the molecular conformation in Form A. The principal difference between the major molecular conformation in Form B and the molecular conformation in Form A involves rotation of the bond linking the piperidine ring to the thiazole ring.

Polymorph Form B of Compound 1 can also be characterized by Differential Scanning Calorimetry. DSC indicates the melting point of polymorph Form B is about 148° C. The details of a DSC experiment are provided in Characterization Example 3. Polymorph Form B is physically stable and non-hydrated in its pure solid form (shown in Characterization Example 4).

Polymorph Form B can be prepared by heating the solid polymorph Form A in methanol/water and then cooling, adding seed crystals of polymorph Form B and filtering (Preparation Example 4). Polymorph Form B can also be prepared directly during the preparation of Compound 1 (Preparation Example 5).

The relative stability of polymorphic Forms A and B of Compound 1 was characterized with Differential Scanning Calorimetry and a competitive interconversion experiment (see Characterization Example 6). These experiments support the conclusion that polymorph Form B is more thermodynamically stable than polymorph Form A and thus the transformation of polymorph Form A into polymorph Form B is irreversible.

Compound 1 can also exist as an amorphous solid. The XRPD pattern for amorphous solid Compound 1 shows no significant signals and thus is readily distinguished from the patterns of polymorph Forms A and B.

The amorphous form of Compound 1 can also be characterized by Modulated Differential Scanning Calorimetry (MDSC). As described in Characterization Example 7 the glass transition temperature of an amorphous form of Compound 1 was determined to be about 68° C. The amorphous form of Compound 1 is stable and non-hydrated in its pure solid form (shown in Characterization Example 4).

The amorphous solid form can be prepared by evaporation to dryness of solutions containing Compound 1 in a solvent (e.g., foam obtained from concentration of chromatography solvent in Preparation Example 1), by cooling melted Compound 1 (obtained by heating any solid form above the melting point), or by spray drying a solution of Compound 1.

As already mentioned, polymorph Form A and B can be prepared directly during the preparation of Compound 1. A method for preparing polymorph Form A or Form B directly from precursor starting materials is shown in Scheme 1. The method involves mixing a compound of Formula 2 and a compound of Formula 3 in the presence of an alkanol solvent. When the reaction is complete the mixture is treated with base to neutralize the one equivalent of generated acid. The reaction mixture is then diluted with water to dissolve salts and encourage the product to crystallize out of solution. Also, seed crystals of the desired crystalline polymorph are added to cause the product to crystallize in the particular polymorphic form.

The reaction of Scheme 1 can be run using a slight excess of either one of the starting compounds of Formula 2 or 3. Typically the molar ratio of the compound of Formula 2 to the compound of Formula 3 is in the range of about 1.2:1 to about 1:1.2. Of note is a molar ratio of about 1:1 (e.g., 1.05:1). Although water-miscible solvents (e.g., acetone, acetonitrile or alcohols) generally work well for the reaction to prepare Compound 1, alkanol solvents work particularly well for both the reaction forming Compound 1 and the crystallization of polymorph Form A or B. Of note are lower (i.e. $C_1$-$C_4$) alkanols. Methanol and ethanol are particularly useful for solubilizing starting materials and promoting clean crystallization of product. The leaving group X in the compound of Formula 3 can be, for example, chloride, bromide, iodide, methanesulfonate or trifluoromethanesulfonate. Chloride, iodide and especially bromide are particularly useful leaving groups for this method. When X is Cl (i.e. chloride), it can be converted in situ to Br (i.e. bromide) by adding one equivalent of a bromide salt (e.g., sodium bromide, lithium bromide or tetrabutylammonium bromide) to the reaction mixture. The compounds of Formula 2 and 3 react to form Compound 1 at ambient temperature; however, the reaction mixture can also be heated to the reflux temperature of the solvent. Heating at or near the boiling point of the solvent is particularly useful for providing a faster rate of reaction. Reactions run at or near the boiling point of the solvent are complete in about 0.5 hour to about 1.5 hours.

Upon completion of the reaction, the reaction mixture is usually diluted with more alkanol solvent (e.g. 0.5 to 1.5 times the original volume of solvent) to promote stirring, and then base and water are added. The alkanol solvent subsequently added to promote stirring can be a different alkanol solvent from that used to conduct the reaction, but the alkanol solvent is typically the same. The reaction forms 1 equivalent (relative to the limiting reagent—i.e. the compound of Formula 2 or 3 that was in lesser molar amount) of acid, which in the absence of base would protonate the product of Formula 1. Therefore typically at least about 1 equivalent of a base is added to neutralize the acid formed. More than 1 equivalent of base can be added, although to minimize cost and waste disposal, typically not more than about 1.5 equivalent of base is added. A wide variety of bases can be used to neutralize the acid formed, and even comparatively weak bases are suitable. Water-soluble bases are preferable, because both the excess base and conjugate acid formed from neutralizing the acid are soluble in the water-containing reaction medium and thus do not contaminate the crystallizing product. Examples of suitable water-soluble bases include alkali metal salts of carbonic acid and carboxylic acids. Sodium bicarbonate and sodium acetate are particularly useful for this method, because they are water-soluble bases available at low cost.

Water is added to the reaction mixture to enhance solubility of byproducts and reduce the solubility of the product, thus promoting clean crystallization of the desired polymorph. The amount of water added typically ranges from about 5% to about 30% by volume relative to the liquid phase. Besides the base and water, an oxidizing agent is optionally added to remove foul-smelling sulfur-containing impurities derived from the thioamide of Formula 2. An aqueous solution of hydrogen peroxide is particularly useful for this purpose. When hydrogen peroxide is added, the amount is typically about 5 to 20 mol % relative to the amount of thioamide of Formula 2 used in the reaction.

After addition of base and water, the reaction mixture is allowed to cool to about 15 to 25° C. below the boiling point of the solvent, at which point seed crystals of the desired polymorph are added. Cooling the reaction mixture prevents the dissolution of the seed crystals before they are able to initiate crystallization of the product. After addition of the seed crystals, the reaction mixture is preferably agitated (e.g., stirred or shaken) to promote nucleation and incipient crystal growth. Agitation is optionally continued while crystallization occurs. The reaction mixture is preferably cooled to about 10 to about 20° C. to ensure complete crystallization of the product from the reaction mixture and to facilitate handling the reaction mixture. The mixture is then filtered to collect the desired crystalline polymorph of Compound 1.

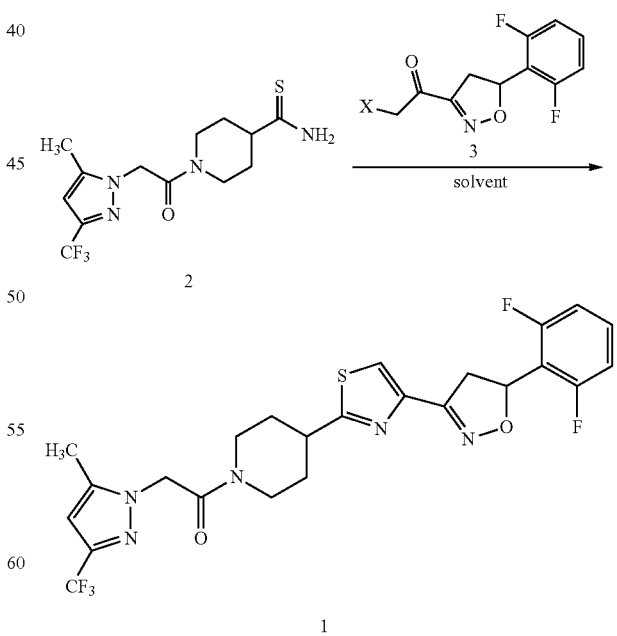

wherein X is Cl, Br, I, $OS(O)_2CH_3$ or $OS(O)_2CF_3$

Polymorph Form B can be prepared from polymorph Form A, because polymorph Form B is the more thermodynamically stable crystalline form. The conversion of polymorph Form A into polymorph Form B can be accomplished by mixing polymorph Form A with an alkanol solvent to form a slurry, adding seed crystals of polymorph Form B to the slurry, and maintaining the slurry while the polymorph Form A converts to polymorph Form B.

Solvents comprising an alkanol work well for the conversion of polymorph Form A to polymorph Form B, because polymorph Form A is somewhat soluble in alkanols, and not only does the polarity of alkanols limit the solubility of Form B, but the solubility can be easily further reduced by addition of water. Inexpensive alkanols that work well for this conversion are lower alkanols (i.e. $C_1$-$C_4$ alkanols), to which can be added water (typically up to about 30% by volume). Of particular note are the alkanols methanol and ethanol. An example of the conversion of polymorph Form A to Form B in pure ethanol is described in the competitive interconversion experiment of Characterization Example 6. Adding water to a solvent comprising an alkanol reduces the solubility of polymorph Form B, thereby enabling more complete and therefore efficient recovery of Form B from the reaction mixture. Including water may also increase the rate of crystallization of polymorph Form B. Typically at least about 5% by volume up to about 50% by volume of water is added relative to the volume of components (e.g., alkanols) in the solvent other than any water already in the solvent. Typically the solvent comprising an alkanol contains no more than about 5% by volume of water before adding water. Also typically after addition of water, the solvent contains about 5% by volume up to about 33% by volume of water. The time and temperature needed to complete conversion of polymorph Form A to polymorph Form B are inversely related. For conversion of polymorph Form A to polymorph Form B the temperature of the reaction mixture is typically at least about 5° C. and not more than about 100° C. Because methanol and ethanol normally boil at considerably lower temperatures than 100° C., when the solvent comprises methanol or ethanol, the temperature is typically not more than about 60° C. At low temperatures (e.g., 5 to 25° C.) the reaction is slow, requiring about 12 to about 48 h to complete conversion to polymorph Form B. At higher temperatures (e.g., 45 to 60° C.) the reaction is fast, requiring about 0.5 to about 4 h to complete conversion to polymorph Form B. An example of a conversion performed in this upper temperature range is described in Preparation Example 4. Completion of the conversion can be easily determined by filtering solid from an aliquot and comparing its melting point to the known melting points of polymorph Forms A and B.

Although adding seed crystals of polymorph Form B to initiate conversion is not necessary (as illustrated in Preparative Example 3), addition of seed crystals ensures that conversion begins without delay and can help accelerate the conversion. An example of the conversion with seed crystals is described in Preparation Example 4.

Polymorph conversion generally benefits from some form of agitation (e.g., stirring or shaking), and therefore the equipment for polymorph conversion usually provides for agitation. Particularly at the beginning of polymorph conversion, the crystallization of polymorph Form B can be accelerated by agitating the reaction mixture, but the conversion can be completed in the absence of agitation. Preparation Example 4 describes a reaction where the conversion was initiated by stirring in the presence of seed crystals and completed by cooling without agitation.

Embodiments of this invention also relate to mixtures of polymorph Forms A and B of Compound 1. A mixture of polymorph Forms A and B can be prepared simply by mixing a sample of polymorph Form A with a sample of polymorph Form B. Any method useful for mixing powders is suitable for this method. Alternatively, mixtures of polymorph Form A and B of Compound 1 can be prepared from polymorph Form A by isolating the mixture of crystals after various time periods (determined by melting point of aliquots) as described in the conversion procedures above. This method can also be used to increase the amount of polymorph B starting with a mixture of polymorph crystal forms.

Without further elaboration, it is believed that one skilled in the art using the preceding description can utilize the present invention. The following Examples are, therefore, to be construed as merely illustrative, and not limiting of the disclosure in any way whatsoever.

PREPARATION EXAMPLE 1

Preparation of Polymorph a of Compound 1

To a stirred solution of 2-chloro-1-[4,5-dihydro-5-(2,6-difluorophenyl)-3-isoxazolyl]ethanone (obtained following a procedure similar to Example 7, Step C in PCT Patent Publication WO 08/013,925) (2.64 g, 10.2 mmol) in acetone (64 mL) was added 1-[2-[5-methyl-3-(trifluoromethyl)-1H-pyrazol-1-yl]acetyl]-4-piperidinecarbothioamide (obtained following the procedure in Example 8, Step C in PCT Patent Publication WO 08/013,925) (3.40 g, 10.2 mmol) and sodium bromide (1.57 g, 15.3 mmol). The reaction mixture was refluxed for 3 hours, cooled to room temperature and then treated with solid sodium bicarbonate (0.92 g, 11.0 mmol) for 30 minutes. The mixture was concentrated, and the residue was partitioned between water and dichloromethane. The organic phase was separated, dried ($MgSO_4$), filtered and concentrated to give the crude reaction product as an oil. The residue was purified by chromatography on silica gel (120 g) using 50-100% ethyl acetate in hexanes as eluant to give the product as a solid foam. The glassy foam was taken up in methanol at room temperature, from which the product crystallized as needles (2.0 g, m.p. 127-130° C.).

PREPARATION EXAMPLE 2

Another Preparation of Polymorph A of Compound 1

To a solution of 2-bromo-1-[4,5-dihydro-5-(2,6-difluorophenyl)-3-isoxazolyl]ethanone (obtained following a procedure similar to Example 12, Step E in PCT Patent Publication WO 08/013,925) (192 g, 0.63 mol) in methanol (500 mL) was added 1-[2-[5-methyl-3-(trifluoromethyl)-1-pyrazol-1-yl]acetyl]-4-piperidinecarbothioamide (obtained following the procedure in Example 8, Step C in PCT Patent Publication WO 08/013,925) (220 g, 0.66 mol), and the reaction mixture was mechanically stirred at room temperature under a nitrogen atmosphere. The solids gradually dissolved and the reaction mixture warmed to 42° C. The reaction mixture was heated to 48° C. for 1.5 h, and then the heat source was removed to allow the reaction mixture to cool. Methanol (1 L) was added to the reaction mixture, followed by dropwise addition of a solution of sodium acetate (54 g, 0.66 mol) in water (120 mL) and aqueous hydrogen peroxide (7 g of 35 wt %). The reaction mixture was heated to 50° C., and water (80 mL) was added dropwise, followed by the removal of the external heat source. After the reaction mixture had cooled to 38° C. and become turbid, seed crystals of polymorph Form A were added. A thick suspension gradually formed when the mixture cooled to about 34° C. The slurry was then externally cooled to 20° C. The solids were collected by filtration, washed with cold methanol/water (2:1 by volume) and dried under vacuum at 50° C. to yield 264 g of polymorph Form A of Compound 1 as a white solid (m.p. 125-128° C.).

PREPARATION EXAMPLE 3

Original Preparation of Polymorph B from Polymorph A

A polythermal method was utilized to measure the solubility and metastable zone width (MSZW) of polymorph Form A. A LARA™ Controlled Laboratory Reactor with a turbidity probe was utilized to detect the disappearance of solids during dissolution trials and the beginning of crystallization during successive cooling experiments. A known amount of polymorph Form A (7.2 g or 5.4 g) was charged into a pre-cooled vessel containing 250 mL of methanol/water (3:1 by volume). The suspensions were continuously stirred at 400 rpm. Two heating profiles of warming from 5° C. to 60° C. and cooling from 60° C. to 5° C. at 0.40 and 0.75° C./min were applied. Optical density changes detected by light transmittance were used to track the dissolution and crystallization of the material during this temperature cycling. Concentration adjustments were made by varying the amount of polymorph Form A added to a fixed volume of solvent.

Dissolution/crystallization profiles (% transmittance vs temperature) were obtained at the two concentrations (29 mg/mL and 21 mg/mL). The profiles from second runs were atypical of the original solid polymorph Form A. The resulting solids isolated by filtration from both experiments exhibited XRPD patterns that were not characteristic of polymorph Form A. This new solid form of Compound 1 was further characterized by single crystal X-ray analysis and Differential Scanning Calorimetry and determined to be a new polymorph (Form B).

PREPARATION EXAMPLE 4

Preparation of Polymorph B of Compound 1 from Polymorph A

Polymorph Form A of Compound 1 (210 g) was combined with methanol (1.5 L) in a Morton flask equipped with magnetic stirring and heated to 60° C. Water (150 mL) was added over 30 minutes while the mixture was maintained at 55-60° C., and then seed crystals of polymorph Form B (10 g) were added to the mixture. The temperature was maintained at 55° C. over 20 minutes during which time the slurry thinned. The mixture was transferred to an Erlenmeyer flask and was allowed to stand at about 45° C. for 15 minutes. The slurry was filtered and the filtrate returned to the Morton flask. The collected solid was washed with 2×100 mL methanol/water (4:1 by volume), and the washings were returned to the Morton flask. The wet solid was dried in a vacuum oven at 60° C. The filtrate and washings in the Morton flask was reheated to 55° C. and polymorph Form A (200 g) was added. The procedure was repeated with this mixture and twice more with additional portions of polymorph Form A to yield a total of 840 g of polymorph Form B melting at 146-148° C.

PREPARATION EXAMPLE 5

Preparation of Polymorph B of Compound 1

To a solution of 2-bromo-1-[4,5-dihydro-5-(2,6-difluorophenyl)-3-isoxazolyl]ethanone (obtained following a procedure similar to Example 12, Step F in PCT Patent Publication WO 08/013,925) (12 g, 40 mmol) in methanol (45 mL) was added 1-[2-[5-methyl-3-(trifluoromethyl)-1H-pyrazol-1-yl]acetyl]-4-piperidinecarbothioamide (obtained following the procedure in Example 8, Step C in PCT Patent Publication WO 08/013,925) (14 g, 42 mmol) and the reaction mixture was magnetically stirred at room temperature under a nitrogen atmosphere. The mixture was warmed to 55° C. over 30 minutes and held at that temperature for an additional 30 minutes. Methanol (45 mL) was added, followed by an aqueous solution of sodium acetate (3.5 g in 8 mL). The mixture cooled to 50° C., and water (6.5 mL) was added dropwise. When the reaction mass became cloudy, seed crystals of polymorph Form B were added, and the mixture was allowed to cool to 47° C., at which temperature crystallization began to occur. Additional water (18.5 mL) was added, and the mixture allowed to cool to room temperature and then to 10° C. with external cooling (ice bath). The slurry was filtered and the solids were washed with 50% methanol/water (2×10 mL). After the solid was air dried for 2 hours the melting point was determined (140-145° C.). The broad melting range suggested the presence of some polymorph Form A, so the solid was reslurried in 3:1 methanol/water (120 mL) and stirred at room temperature overnight. The solid was then collected by filtration, washed with 50% methanol/water (2×10 mL) and dried in air for 1 hour and in a vacuum oven at 50° C. for 18 hours. The resultant white solid (20 g) had a sharp melting point (143-145° C.) consistent with polymorph Form B.

CHARACTERIZATION EXAMPLE 1

X-Ray Powder Diffraction Experiments

Powder X-ray diffraction was used to identify the crystallized phases of both polymorph Forms A and B of Compound 1. To characterize polymorph Forms A and B, data were obtained with a Philips X'PERT Model 3040 automated powder diffractometer. Samples at room temperature were run in a batch mode with a Model PW 1775 or Model PW 3065 multi-position sample changer. The diffractometer was equipped with an automatic variable slit, an X'Celerator solid state detector, and a nickel filter. The radiation was Cu (Kα), 45 kV, 40 mA. Samples were packed powders in an aluminum sample holder. Data were collected at 2θ angles from 2 to 60 degrees using a continuous scan with an equivalent step size of 0.03 degrees and a count time of 2.0 seconds per step. MDI/Jade software was used with the International Committee for Diffraction Data database for phase identification and comparison of diffraction patterns of the samples with those of reference materials.

TABLE 1

2θ X-ray maxima for Polymorph A of Compound 1

| 2θ | 2θ | 2θ | 2θ | 2θ | 2θ | 2θ |
|---|---|---|---|---|---|---|
| 4.595 | 17.563 | 22.116 | 29.924 | 35.937 | 43.67 | 51.904 |
| 8.773 | 18.104 | 22.684 | 30.388 | 36.409 | 43.974 | 52.962 |
| 9.145 | 18.366 | 22.93 | 30.841 | 37.348 | 44.624 | 54.268 |
| 10.293 | 18.69 | 23.621 | 31.306 | 37.691 | 45.533 | 54.447 |
| 13.321 | 18.996 | 24.326 | 31.692 | 39.028 | 46.661 | 55.353 |
| 13.701 | 19.329 | 25.852 | 32.109 | 39.771 | 47.5 | 56.401 |
| 14.685 | 19.81 | 26.792 | 32.565 | 40.441 | 48.63 | 56.938 |
| 15.515 | 20.118 | 27.412 | 33.302 | 41.083 | 49.556 | 58.087 |
| 15.99 | 20.717 | 28.087 | 34.131 | 41.66 | 49.834 | 58.507 |
| 17.086 | 21.194 | 28.583 | 34.53 | 41.887 | 50.646 | 59.265 |
| 17.353 | 21.615 | 29.331 | 35.246 | 42.609 | 51.198 | |

TABLE 2

2θ X-ray maxima for Polymorph B of Compound 1

| 2θ | 2θ | 2θ | 2θ | 2θ | 2θ | 2θ |
|---|---|---|---|---|---|---|
| 9.594 | 19.208 | 25.807 | 32.145 | 38.355 | 47.204 | 55.279 |
| 13.01 | 19.508 | 26.208 | 32.756 | 39.081 | 47.776 | 56.395 |
| 14.081 | 20.204 | 26.947 | 33.513 | 40.615 | 48.547 | 57.101 |
| 14.489 | 20.883 | 27.413 | 33.825 | 41.416 | 48.95 | 58.479 |
| 14.902 | 21.79 | 27.814 | 34.388 | 41.932 | 49.669 | 58.931 |
| 15.931 | 22.718 | 28.255 | 35.201 | 42.515 | 50.814 | |
| 16.1 | 23.328 | 29.127 | 35.389 | 43.308 | 51.403 | |
| 16.998 | 24.186 | 29.318 | 36.264 | 43.853 | 52.479 | |
| 17.503 | 24.422 | 29.891 | 36.728 | 44.416 | 53.151 | |
| 18.123 | 25.224 | 30.651 | 37.039 | 46.234 | 54.347 | |
| 18.87 | 25.469 | 31.492 | 37.469 | 46.564 | 54.903 | |

CHARACTERIZATION EXAMPLE 2

Single Crystal X-Ray Diffraction for Polymorph Form A

A colorless needle of polymorph Form A of Compound 1 having approximate dimensions of 0.56×0.13×0.04 mm was mounted on a glass fiber in random orientation. Preliminary examination and data collection were performed with Mo $K_\alpha$ radiation ($\lambda$=0.71073 Å) on a Nonius KappaCCD diffractometer equipped with a graphite crystal, incident beam monochromator. Refinements were performed on a computer workstation running the program SHELX97 on a LINUX operating system. Cell constants and an orientation matrix for data collection were obtained from least-squares refinement using the setting angles of 16278 reflections in the range 2°<θ<27°. The refined mosaicity from Denzo/Scalepack is 0.68° indicating moderate crystal quality. The space group was determined by the program XPREP. There were no systematic absences, and the space group was determined to be P-1 (no. 2). The data were collected to a maximum 2θ value of 54.9°, at a temperature of 150±1 K.

The triclinic cell parameters and calculated volume were determined to be: a=6.2489(2) Å, b=10.0340(5) Å, c=19.2458(10) Å, $\alpha$=83.1638(18)°, $\beta$=88.2845(19)°, $\gamma$=85.174(3)°, V=1193.67(9) Å$^3$. The molecular weight of Compound 1 is 539.53 g mol$^{-1}$ With Z=2, the resultant density was calculated to be 1.501 g cm$^{-3}$. The space group was determined to be P-1 (no. 2). The crystal structure of Form A adopts a centrosymmetric space group, despite the presence of a chiral center at C22. The non-chiral space group occurs because Form A crystallizes as a racemate with alternating layers of R and S absolute molecular configurations. Compound 1 adopts a single conformation in this polymorph form. The single crystal X-ray data is listed in Tables 3 and 4. The atomic coordinates (×10$^4$) and equivalent isotropic displacement parameters (A$^2$×10$^3$) are listed and U(eq) is defined, as one third of the trace of the orthogonalized Uij tensor. The estimated standard deviations are shown in parentheses.

TABLE 3

Atomic coordinates and their estimated standard deviations for polymorph Form A

| Atom | x | y | z | U(eq) |
|---|---|---|---|---|
| S15 | 0.08617(10) | 0.07506(6) | 0.09057(3) | 0.02888(19) |
| F1 | 0.6509(2) | 0.12563(19) | -0.47798(9) | 0.0562(6) |
| F2 | 0.5325(3) | 0.33158(18) | -0.50243(9) | 0.0545(6) |
| F3 | 0.3923(3) | 0.17644(19) | -0.54884(8) | 0.0505(6) |
| F25 | -1.1151(2) | 0.24418(15) | 0.31793(8) | 0.0404(5) |
| F29 | -0.4850(2) | 0.46381(15) | 0.26681(8) | 0.0358(4) |
| O7 | 0.4288(3) | 0.13635(17) | -0.22611(9) | 0.0327(5) |
| O21 | -0.7571(3) | 0.38682(18) | 0.16391(9) | 0.0309(5) |
| N1 | 0.1681(3) | 0.2291(2) | -0.33351(10) | 0.0251(6) |
| N2 | 0.3275(3) | 0.2679(2) | -0.37866(10) | 0.0280(6) |
| N8 | 0.3129(3) | 0.2991(2) | -0.15860(10) | 0.0248(5) |
| N18 | -0.1609(3) | 0.29174(19) | 0.06342(10) | 0.0235(5) |
| N20 | -0.5695(3) | 0.3651(2) | 0.12246(10) | 0.0263(6) |
| C3 | 0.3141(4) | 0.1919(3) | -0.43008(13) | 0.0269(7) |
| C4 | 0.1495(4) | 0.1056(3) | -0.41880(14) | 0.0312(8) |
| C5 | 0.0568(4) | 0.1321(2) | -0.35583(13) | 0.0270(7) |
| C6 | 0.1402(4) | 0.2931(3) | -0.27018(13) | 0.0266(7) |
| C7 | 0.3078(4) | 0.2355(2) | -0.21600(12) | 0.0235(6) |
| C9 | 0.1545(4) | 0.4054(3) | -0.13909(14) | 0.0262(7) |
| C10 | 0.0191(4) | 0.3496(3) | -0.07777(13) | 0.0229(7) |
| C11 | 0.1587(4) | 0.2908(2) | -0.01565(13) | 0.0234(7) |
| C12 | 0.3373(4) | 0.1893(3) | -0.03802(14) | 0.0273(7) |
| C13 | 0.4610(4) | 0.2492(3) | -0.10195(14) | 0.0282(8) |
| C14 | 0.0194(4) | 0.2315(2) | 0.04337(12) | 0.0232(7) |
| C16 | -0.1423(4) | 0.0948(3) | 0.14017(13) | 0.0261(7) |
| C17 | -0.2532(4) | 0.2142(2) | 0.11896(12) | 0.0228(6) |
| C19 | -0.4565(4) | 0.2613(2) | 0.15104(12) | 0.0230(6) |
| C22 | -0.7599(4) | 0.2817(3) | 0.22422(13) | 0.0257(7) |
| C23 | -0.5472(4) | 0.1960(3) | 0.21839(14) | 0.0266(7) |
| C24 | -0.7990(4) | 0.3514(2) | 0.28886(12) | 0.0239(6) |
| C25 | -0.9766(4) | 0.3342(2) | 0.33245(13) | 0.0273(7) |
| C26 | -1.0239(4) | 0.4035(3) | 0.38979(14) | 0.0350(8) |
| C27 | -0.8830(5) | 0.4950(3) | 0.40448(14) | 0.0355(8) |
| C28 | -0.6995(4) | 0.5157(3) | 0.36317(14) | 0.0334(8) |
| C29 | -0.6646(4) | 0.4439(3) | 0.30746(13) | 0.0271(7) |
| C31 | 0.4699(4) | 0.2064(3) | -0.48928(14) | 0.0347(8) |
| C51 | -0.1311(5) | 0.0752(3) | -0.31645(17) | 0.0377(9) |

TABLE 4

Hydrogen coordinates and their estimated standard deviations for polymorph Form A

| Atom | x | y | z | U(eq) |
|---|---|---|---|---|
| H4 | 0.106(4) | 0.044(3) | -0.4467(14) | 0.038(8) |
| H11 | 0.232(4) | 0.363(3) | -0.0003(13) | 0.028(7) |
| H16 | -0.185(4) | 0.029(2) | 0.1774(13) | 0.024(6) |
| H22 | -0.883(4) | 0.227(2) | 0.2185(12) | 0.024(6) |
| H26 | -1.159(4) | 0.391(3) | 0.4176(14) | 0.039(8) |
| H27 | -0.914(4) | 0.543(3) | 0.4446(15) | 0.043(8) |
| H28 | -0.601(4) | 0.573(3) | 0.3733(15) | 0.044(9) |
| H62 | -0.004(4) | 0.280(2) | -0.2527(12) | 0.025(6) |
| H71 | 0.149(4) | 0.389(3) | -0.2825(12) | 0.024(6) |
| H91 | 0.236(4) | 0.479(3) | -0.1279(13) | 0.035(7) |
| H92 | 0.066(4) | 0.440(2) | -0.1789(13) | 0.027(7) |
| H101 | -0.087(4) | 0.419(3) | -0.0644(13) | 0.030(7) |
| H102 | -0.066(4) | 0.279(2) | -0.0938(12) | 0.020(6) |
| H121 | 0.442(4) | 0.164(2) | 0.0000(13) | 0.027(7) |
| H122 | 0.274(4) | 0.108(3) | -0.0494(13) | 0.030(7) |
| H131 | 0.535(4) | 0.331(3) | -0.0894(14) | 0.037(7) |
| H132 | 0.566(3) | 0.184(2) | -0.1181(11) | 0.013(5) |
| H231 | -0.451(4) | 0.201(2) | 0.2570(13) | 0.025(7) |
| H232 | -0.570(4) | 0.098(3) | 0.2172(13) | 0.031(7) |
| H51A | -0.098(5) | 0.037(3) | -0.2691(17) | 0.051(9) |
| H51B | -0.245(5) | 0.143(3) | -0.3110(15) | 0.054(9) |
| H51C | -0.179(5) | 0.005(3) | -0.3431(17) | 0.059(10) |

CHARACTERIZATION EXAMPLE 3

Differential Scanning Calorimetry Experiments

Differential scanning calorimetry was performed on a Thermal Analysis Q2000 Differential Scanning Calorimeter. A sample (2.3 mg) was placed in an aluminum DSC pan. The sample cell was heated under a nitrogen purge at 10° C./minute. Indium metal was used as the calibration standard.

The DSC curve for polymorph Form A of Compound 1 was observed to exhibit a sharp endotherm, confirmed as the melt by hotstage microscopy, with an onset temperature at 120° C. (signal maximum at 127° C.). The heat of fusion was determined to 63 J/g.

The DSC curve for polymorph Form B of Compound 1 was observed to exhibit a sharp endotherm, confirmed as the melt by hotstage microscopy, with an onset temperature at 144° C. (signal maximum at 148° C.). The heat of fusion was determined to 82 J/g.

CHARACTERIZATION EXAMPLE 4

Stability Experiments for Solid Forms of Compound 1

The physical stability of polymorph Form A was characterized. Samples of Form A maintained at 40, 60, and 80° C. for 4 days remained unchanged by XRPD. Samples of Form A exposed to 53, 75, and 85% relative humidity at ambient temperature (10 days) were also unchanged, as determined by XRPD.

The physical stability of polymorph Form B was characterized. Samples of Form B maintained at 40° C. and 25° C. for 4 days remained unchanged by XRPD. Samples of Form B exposed to 85% relative humidity at ambient temperature (10 days) were also unchanged, as determined by XRPD.

The physical stability of the amorphous material was characterized. Amorphous Compound 1 samples exposed to elevated temperatures (60, 80 and 100° C.) and humidities (75 and 85% relative humidity) for 10-12 days remained unchanged by XRPD. This indicates that the amorphous solid is physically stable at these conditions.

CHARACTERIZATION EXAMPLE 5

Single Crystal X-Ray Diffraction for Polymorph Form B

A rectangular plate of polymorph Form B of Compound 1 having approximate dimensions of 0.20×0.09×0.02 mm was mounted on a glass fiber in random orientation. Preliminary examination and data collection were performed with Mo K$_\alpha$ radiation ($\lambda$=0.71073 Å) on a Bruker Apex-II CCD diffractometer equipped with a graphite crystal, incident beam monochromator. Refinements were performed on a computer workstation running the program SHELX97 on a LINUX operating system. Cell constants and an orientation matrix for data collection were obtained from least-squares refinement using the setting angles of 16001 reflections in the range 1.63°<θ<24.15°. Data were integrated using the program SAINT. The space group was determined by the program XPREP. The space group was determined to be Pbca (no. 2) based upon the systematic absences. The data were collected to a maximum 2θ value of 48.30°, at a temperature of 173±1 K.

The orthorhombic cell parameters and calculated volume were determined to be: a=13.434(3) Å, b=14.661(3) Å, c=24.237(5) Å, α=90°, β=90, γ=90, V=4773.5(17) Å$^3$. The molecular weight of Compound 1 is 539.53 g mol$^{-1}$. With Z=8 the resultant density was calculated to be 1.501 g cm$^{-3}$. The space group was determined to be Pbca. The crystal structure of polymorph Form B adopts a centric space group consistent for a racemate. One end of the molecule is disordered. Compound 1 adopts two different conformations in this polymorph (one conformation in 71% abundance and another in 29% abundance). The single crystal X-ray data is listed in Tables 5 and 6. Note that the atoms are numbered differently than for polymorph Form A (e.g., the chiral center where the isoxazoline ring joins the difluorophenyl ring is C18 in Form B and C22 in Form A). The atomic coordinates (×10$^4$) and equivalent isotropic displacement parameters (Å$^2$×10$^3$) are listed and U(eq) is defined as one third of the trace of the orthogonalized Uij tensor. The estimated standard deviations are shown in parentheses.

TABLE 5

Atomic coordinates and their estimated standard deviations for polymorph Form B

| Atom | x | y | z | U(eq) |
|---|---|---|---|---|
| S(1) | 4497(1) | 1123(1) | 3429(1) | 45(1) |
| O(1) | 4707(3) | 5575(3) | 4272(2) | 52(1) |
| F(1) | 6512(3) | 8851(2) | 5106(2) | 68(1) |
| N(1) | 6152(3) | 6775(3) | 4036(2) | 34(1) |
| C(1) | 5888(4) | 8118(4) | 4318(2) | 36(2) |
| F(2) | 6022(3) | 9684(2) | 4436(1) | 64(1) |
| N(2) | 6265(3) | 7323(3) | 4485(2) | 34(1) |
| C(2) | 5540(4) | 8080(4) | 3775(2) | 37(1) |
| F(3) | 4960(3) | 8975(2) | 4944(2) | 71(1) |
| N(3) | 5673(3) | 4324(3) | 4220(2) | 40(1) |
| C(3) | 5711(4) | 7204(4) | 3604(2) | 36(1) |
| N(4) | 6402(3) | 1167(3) | 3370(2) | 37(1) |
| C(4) | 5840(5) | 8899(4) | 4695(3) | 47(2) |
| N(5) | 7714(4) | −85(3) | 2816(2) | 57(2) |
| C(5) | 5497(5) | 6720(4) | 3078(2) | 53(2) |
| C(6) | 6429(4) | 5818(3) | 4073(2) | 39(2) |
| C(7) | 5518(4) | 5224(4) | 4200(2) | 36(1) |
| C(8) | 6633(4) | 3874(4) | 4154(2) | 44(2) |
| C(9) | 6529(4) | 3061(3) | 3759(2) | 38(2) |
| C(10) | 5748(4) | 2392(3) | 3965(2) | 33(1) |
| C(11) | 4759(4) | 2905(4) | 4046(2) | 41(2) |
| C(12) | 4898(4) | 3719(4) | 4427(2) | 42(2) |
| C(13) | 5651(4) | 1587(3) | 3591(2) | 34(1) |
| C(14) | 6073(4) | 443(4) | 3044(2) | 39(2) |
| C(15) | 5070(4) | 328(4) | 3032(2) | 40(2) |
| C(16) | 6758(4) | −148(5) | 2759(2) | 55(2) |
| O(2) | 8210(3) | −832(3) | 2529(2) | 31(1) |
| C(17) | 6468(5) | −985(5) | 2423(3) | 41(2) |
| C(18) | 7448(5) | −1473(5) | 2325(3) | 35(2) |
| C(19) | 7691(6) | −1711(6) | 1742(3) | 27(2) |
| C(20) | 7695(6) | −1087(5) | 1315(3) | 32(2) |
| C(21) | 7878(8) | −1279(8) | 777(5) | 54(3) |
| C(22) | 8032(7) | −2083(8) | 631(4) | 56(3) |
| C(23) | 8080(8) | −2831(8) | 992(4) | 46(3) |
| C(24) | 7899(6) | −2598(7) | 1563(3) | 37(2) |
| F(4) | 7507(3) | −199(3) | 1453(2) | 50(2) |
| F(5) | 7894(3) | −3249(3) | 1975(2) | 55(2) |
| O(2') | 8096(9) | −369(10) | 2270(6) | 51(4) |
| C(17') | 6361(10) | −510(12) | 2161(7) | 25(5) |
| C(18') | 7349(12) | −517(12) | 1837(7) | 48(6) |
| C(19') | 7621(15) | −1409(10) | 1565(6) | 29(6) |
| C(20') | 7696(15) | −2233(12) | 1832(7) | 37(6) |
| C(21') | 7952(15) | −3081(13) | 1631(9) | 39(6) |
| C(22') | 8094(15) | −3067(12) | 1146(8) | 24(6) |
| C(23') | 8102(12) | −2381(10) | 746(7) | 8(4) |
| C(24') | 7820(20) | −1482(13) | 992(8) | 69(10) |
| F(4') | 7558(10) | −2236(10) | 2390(5) | 79(5) |
| F(5') | 7714(10) | −679(10) | 714(5) | 77(5) |

TABLE 6

Hydrogen coordinates for polymorph Form B

| Atom | x | y | z | U(eq) |
|---|---|---|---|---|
| H(2A) | 5252 | 8550 | 3573 | 45 |
| H(5A) | 6109 | 6499 | 2922 | 80 |
| H(5B) | 5185 | 7132 | 2824 | 80 |
| H(5C) | 5061 | 6214 | 3149 | 80 |

TABLE 6-continued

Hydrogen coordinates for polymorph Form B

| Atom | x | y | z | U(eq) |
|---|---|---|---|---|
| H(6A) | 6922 | 5740 | 4361 | 47 |
| H(6B) | 6724 | 5625 | 3727 | 47 |
| H(8A) | 6870 | 3664 | 4509 | 53 |
| H(8B) | 7114 | 4304 | 4007 | 53 |
| H(9A) | 6343 | 3280 | 3396 | 46 |
| H(9B) | 7165 | 2752 | 3727 | 46 |
| H(10A) | 5964 | 2169 | 4327 | 39 |
| H(11A) | 4514 | 3113 | 3691 | 49 |
| H(11B) | 4268 | 2494 | 4202 | 49 |
| H(12A) | 4276 | 4052 | 4456 | 50 |
| H(12B) | 5077 | 3506 | 4793 | 50 |
| H(15A) | 4742 | −124 | 2833 | 49 |
| H(17A) | 6010 | −1369 | 2627 | 49 |
| H(17B) | 6161 | −810 | 2077 | 49 |
| H(18A) | 7466 | −2028 | 2550 | 42 |
| H(21A) | 7889 | −812 | 517 | 65 |
| H(22A) | 8121 | −2195 | 256 | 67 |
| H(23A) | 8216 | −3422 | 875 | 55 |
| H(17C) | 6071 | −1114 | 2186 | 29 |
| H(17D) | 5881 | −94 | 1999 | 29 |
| H(18B) | 7363 | −19 | 1568 | 58 |
| H(21B) | 8006 | −3601 | 1848 | 47 |
| H(22B) | 8230 | −3641 | 1002 | 29 |
| H(23B) | 8260 | −2472 | 377 | 9 |

CHARACTERIZATION EXAMPLE 6

Relative Stability Experiments for Polymorph Form A and Form B

The relative stability of polymorphic Forms A and B of Compound 1 was characterized with Differential Scanning Calorimetry and a competitive interconversion experiment. Phase transitions of solids can be thermodynamically reversible or irreversible. Crystalline polymorphs which transform reversibly at a specific transition temperature ($T_{tr}$) are called enantiotropic polymorphs. If the crystalline polymorphs are not interconvertable, the system is monotropic (i.e. one polymorph is thermodynamically stable relative to the other over the entire temperature range up to melting). The relationship between forms can be determined by the application of the heat of fusion rule (Burger, A.; Ramberger, R. *Mikrochim. Acta [Wein]*, 1979 II, 259-271). The rule states that if the higher melting form has the lower heat of fusion, then the two forms are enantiotropic. Otherwise, they are monotropic. Based on this rule, the DSC data (measured in Characterization Example 3) show that polymorph Form A (mp~120° C., $\Delta H_f$=64 J/g) and polymorph Form B (mp~144° C., $\Delta H_f$=82 J/g) are monotropically related. More specifically, polymorph Form B is the most stable form throughout the temperature range up to the melt.

To support this conclusion, a competitive interconversion experiment between polymorph Forms A and B was performed in ethanol at room temperature. Equal amounts of Forms A and B were added to saturated ethanol and the suspension was continuously stirred for 4 days. The solids were recovered by vacuum filtration and identified as polymorph Form B by XRPD. This indicates that polymorph Form B is more stable than polymorph Form A under these conditions, consistent with prediction from the DSC data for polymorph Forms A and B.

CHARACTERIZATION EXAMPLE 7

Modulated Differential Scanning Calorimetry Experiment

Modulated Differential Scanning Calorimetry was performed on a TA Instruments 2920 Differential Scanning Calorimeter equipped with a refrigerated cooling system (RCS). Compound 1 (4.4 mg) was placed in an aluminum DSC pan. Temperature and heat capacity measurements were calibrated using indium metal and sapphire as calibration standards, respectively. The glass transition temperature was determined to be about 68° C. from the half-height/inflection of the step change in the reversible heat flow versus temperature curve.

Formulation/Utility

A solid form of Compound 1 will generally be used as a fungicidal active ingredient in a composition, i.e. formulation, with at least one additional component selected from the group consisting of surfactants, solid diluents and liquid carriers (i.e. liquid fluids that carry the active and possibly other ingredients; also called liquid diluents). The formulation or composition ingredients are selected to be consistent with the physical properties of the active ingredient, mode of application and environmental factors such as soil type, moisture and temperature.

Useful formulations of fungicidal active ingredients generally include both liquid and solid compositions. Liquid compositions include solutions (e.g., emulsifiable concentrates), emulsions (including micro-emulsions), dispersions and suspensions, and combinations of these forms (e.g., suspo-emulsions). The term "suspension" particularly refers to a dispersion of particulates that has been stabilized by addition of a chemical additive to minimize or stop sedimentation of the active ingredient. In a dispersion or suspension of particulates (e.g., aqueous suspension concentrate and oil dispersion formulations), a liquid carrier forms a continuous liquid phase in which the particulates (e.g., of a solid form of Compound 1) are dispersed or suspended. In a composition that combines a suspension or dispersion of particulates with an emulsion containing a second (immiscible) liquid (e.g., a suspo-emulsion formulation), a liquid carrier forms a continuous liquid phase in which not only the particulates are suspended but also droplets (i.e. non-continuous liquid phase) of the second liquid are emulsified.

Dispersions and suspensions may be aqueous (i.e. containing mainly water as the liquid carrier) or non-aqueous (i.e., comprising water-immiscible organic compounds, commonly referred to as "oil", as the liquid carrier) according to the nature of the liquid carrier forming the continuous liquid phase. The general types of aqueous liquid compositions include soluble concentrates, suspension concentrates, capsule suspensions, concentrated emulsions, micro-emulsions and suspo-emulsions. Thus in suspo-emulsions the liquid carrier forming the continuous liquid phase is aqueous (i.e. contains water as its main constituent) and a water-immiscible liquid component is emulsified in the aqueous liquid carrier. The general types of non-aqueous liquid compositions include emulsifiable concentrates, micro-emulsifiable concentrates, dispersible concentrates and oil dispersions. Suspension concentrates contain particulates dispersed in a continuous liquid phase and exists as particulate dispersions on addition to water. Suspo-emulsions and oil dispersions form both particulate dispersions and emulsions that coexist on addition to water, where one or more of these phases may contain active ingredient. (In the present compositions, the particulate dispersions comprise a solid form of Compound 1.)

The general types of solid compositions include dusts, powders, granules, pellets, prills, pastilles, tablets, filled films (including seed coatings) and the like, which can be water-dispersible ("wettable") or water-soluble. Films and coatings formed from film-forming liquids are particularly useful for seed treatment, in addition to having applications in both liquid and solid formulation types in general. Active ingredients can be encapsulated (including micro-encapsulated) and further formed into a liquid suspension or dispersion or into a solid formulation, to protect the active ingredient or control or delay release of the active ingredient on application to the target. Alternatively, the entire formulation, including the active ingredient, can be encapsulated (or "overcoated"). Encapsulation can also control or delay release of the active ingredient. High-strength compositions can be prepared and used as intermediates for subsequent use in preparing lower strength liquid and solid formulations.

Although the solid forms of Compound 1 according to the present invention can be used to prepare liquid solutions, emulsifiable concentrates and emulsions by combining with a solvent dissolving the solid forms, the solid forms can only retain their identity in formulated compositions containing Compound 1 as a solid (e.g., particles). The fungicidal compositions of the present invention wherein the composition comprises at least one solid form of Compound 1 thus include liquid compositions containing Compound 1 as a solid (e.g., dispersions, suspensions, suspo-emulsions) and solid compositions of Compound 1.

Even though both polymorph Form A and the amorphous solid form of Compound 1 can be used to prepare fungicidal compositions of the present invention, polymorph Form B is particularly useful for forming fungicidal compositions, especially liquid compositions, having excellent physical as well as chemical stability. Although both polymorph Form A and the amorphous solid form of Compound 1 are relatively stable when isolated and maintained near room temperature, they are nevertheless thermodynamically unstable relative to polymorph Form B. Therefore they are inherently susceptible to conversion to Polymorph Form B. Contact with solvents generally promotes conversion of crystal forms. Therefore liquid compositions comprising polymorph Form A or the amorphous solid form of Compound 1 are particularly vulnerable to spontaneous recrystallization to Polymorph Form B. Because of minimal nucleation and slow growth, the polymorph Form B crystals formed will be relatively few but large. This can result in both decreased biological efficacy and increased settling of the active ingredient, because high biological activity and suspensibility depend upon small particle size of solid active ingredient dispersed in liquid compositions. Using polymorph Form B to prepare fungicidal compositions removes the risk of later recrystallization in the compositions. Accordingly of note is a fungicidal composition of the invention comprising polymorph Form B.

Although any form of Compound 1 can be used to prepare liquid compositions wherein Compound 1 is completely dissolved (e.g., solutions, emulsifiable concentrates), polymorph Form B is advantageously used to develop formulation recipes for these types of liquid compositions. Consistent with its higher melting point, polymorph Form B is generally less soluble than polymorph Form A and the amorphous solid form of Compound 1. Therefore types and amounts of solvents found sufficient to completely dissolve polymorph Form B will provide recipes for stable formulations, whereas types and amounts of solvents found sufficient to completely dissolve polymorph Form A or the amorphous solid form of Compound 1 may result in later crystallization of polymorph Form B from the composition. After the types and amounts of solvents are determined to be sufficient for solubility of polymorph Form B, any form of Compound 1 can be then used to produce the composition. Other forms of Compound 1 may be less expensively produced than polymorph Form B, and thus preferable for making compositions in which Compound 1 is dissolved.

Both liquid and solid formulations comprising at least one solid form of Compound 1 will typically contain effective amounts of active ingredient, solid diluent or liquid carrier, and surfactant within the following approximate ranges, which add up to 100 percent by weight. General ranges of amounts of active ingredient (i.e. a solid form of Compound 1 and optionally other active ingredients), diluent and surfactant components in the present composition comprising at least one solid form of Compound 1 are as follows:

|  | Weight Percent | | |
| --- | --- | --- | --- |
|  | Active Ingredient | Diluent | Surfactant |
| Water-Dispersible Granules, Tablets and Powders | 0.001-90 | 0-99.999 | 0-25 |
| Oil Dispersions, Aqueous Suspensions | 1-60 | 40-99 | 0-50 |
| Dusts | 1-25 | 70-99 | 0-5 |
| Granules and Pellets | 0.001-95 | 5-99.999 | 0-20 |
| High Strength Compositions | 90-99 | 0-10 | 0-10 |

Solid diluents include, for example, traditional and organically modified clays such as bentonite, montmorillonite, attapulgite and kaolin, gypsum, cellulose, titanium dioxide, zinc oxide, starch, dextrin, sugars (e.g., lactose, sucrose), silica, talc, mica, diatomaceous earth, urea, calcium carbonate, sodium carbonate and bicarbonate, and sodium sulfate. Typical solid diluents are described in Watkins et al., *Handbook of insecticide Dust Diluents and Carriers,* 2nd Ed., Dorland Books, Caldwell, N.J.

Liquid carriers for formulation of agricultural active ingredients are generally liquids at room temperature (e.g., 20° C.). Liquid carriers include "aqueous" (i.e. water optionally containing dissolved water-soluble compounds) and "water-immiscible" (e.g. liquid containing water-immiscible organic compounds and, at most, an insignificant (e.g., no more than about 5% by weight) amount of water).

The term "aqueous liquid carrier" as used herein particularly refers to a liquid carrier comprising water as the main (i.e. at least 50% by weight) component. In addition to water, an aqueous liquid carrier can contain dissolved water-soluble compounds, including water-miscible solvents such as N-alkylpyrrolidones (e.g., N-methylpyrrolidinone), mono- and di-alkyl ethers of glycols and polyglycols (e.g., monomethyl ethers of mono-, di- and tri-propylene glycol), ethylene glycol, triethylene glycol, propylene glycol, dipropylene glycol, polypropylene glycol, propylene carbonate, glycerine, alcohols, which can be linear, branched, saturated or unsaturated (e.g., methanol, ethanol, n-propanol, isopropyl alcohol) and dimethyl sulfoxide.

The term "water-immiscible liquid carrier" as used herein particularly refers to a liquid carrier comprising one or more water-immiscible organic compounds in a total amount of at least about 50%, more typically at least about 60%, 70%, 80%, 90% or 95% of the carrier by weight. In this context, organic compound refers to molecules containing carbon as well as other atoms. The one or more water-immiscible organic compounds forming the water-immiscible liquid carriers for the present invention are typically soluble in water to an extent of less than about 0.1%, or less than about 0.01%, or less than about 0.001% by weight at 0° C. Often liquid water-immiscible organic compounds are described as "oils". Examples of water-immiscible organic compounds suitable as water-immiscible liquid carriers for compositions of the present invention include, but are not limited to: mineral oils, also known as liquid petrolatum, liquid paraffin, paraffin oil, normal paraffins, isoparaffins and paraffinic oil, comprised of a mixture of long-chain, liquid hydrocarbons obtained from petroleum. Mineral oils are commercially available from multiple sources, as a straight mineral oil or mineral oil blends with emulsifiers, for example, Isopar® H (Deutsche Exxon Chemicals) or Suremix® (DuPont, USA).

Also useful as water-immiscible organic compounds suitable as water-immiscible liquid carriers for compositions of the present invention are vegetable and animal-sourced oils. These oils are usually obtained by pressing or solvent extraction of plant seed (e.g, oils of olive, castor, linseed, sesame, corn (maize), peanut, sunflower, grapeseed, safflower, cottonseed, soybean, rapeseed, coconut and palm kernel) and the fractionation of animal-sourced fats (e.g., beef tallow, pork tallow, lard, cod liver oil, fish oil). These oils comprise mostly fatty acid glycerides, i.e. glycerol esters of saturated and unsaturated fatty acids (typically $C_6$-$C_{22}$). Alkylated fatty acids (e.g., methylated, ethylated, butylated) obtained by transesterification of both plant and animal-sourced glycerol esters, including higher-grade products that have been further purified by distillation, are commercially available and also useful as water-immiscible liquid carriers for the present compositions. Fatty acid esters of $C_1$-$C_4$ alkanols (i.e. fatty acids esterified with $C_1$-$C_4$ alkanols instead of glycerol) have lower viscosities than seed oils. The fatty acid portions of these esters typically consist of a carboxylate moiety bound to the hydrocarbon chain, which can be branched or unbranched. The latter is more typical of plant or animal-sourced esters. Of particular note are the fatty acid esters which are fatty acids esterified with $C_1$-$C_2$ alkanols (lower alkyl esters of fatty esters) for reasons including favorable physical properties, commercial availability and cost. The fatty acid alkanol esters in a composition of the present invention can also be derived from a mixture of alcohols (e.g., methanol and ethanol).

The hydrocarbon chain of commercially available fatty acid esters can be saturated or unsaturated, with the degree of unsaturation typically being no greater than 1 or 2 carbon-carbon double bonds. Fatty acid esters formed from fatty acids containing either both odd and even numbers of carbon in the hydrocarbon chain are useful in the compositions of the present invention. Although the compositions of the present invention can include short chain fatty acid esters ($C_4$-$C_6$), mixtures with longer chain fatty acids esters ($C_{10}$-$C_{22}$) are preferred and useful in controlling the polarity and volatility of the composition, the solubility of the active ingredient in the water-immiscible liquid carrier and the solubility of the water-immiscible liquid carrier in water and other aqueous liquid carriers of the present invention (e.g., the continuous liquid phase of a suspo-emulsion). Of note are fatty acids obtained from natural sources, typically containing an even number of carbon atoms ($C_{10}$-$C_{22}$) and alkanol esters of these fatty acids for reasons of commercial availability and cost. The ($C_{10}$-$C_{22}$) fatty acid esters with an even number of carbon atoms include: erucic acid, lauric acid, palmitic acid, stearic acid, oleic acid, linoleic acid and linolenic acid.

Commercially available fatty acid compositions obtained from natural sources (e.g., seed oils) typically consist of fatty acids having a range of chain lengths and different degrees of unsaturation. These mixtures can be useful in the compositions of the present invention without need to first separate the fatty acid esters. Of note is a liquid composition of the invention wherein the liquid carrier comprises fatty acid methyl esters derived from seed oils of sunflower, soybean, cotton or linseed or rapeseed, and particularly rapeseed (e.g., methyl canolate) or soybean (e.g., methyl soyate).

Fatty acid esters of alkanols and methods for their preparation are well known in the art. For example, "biodiesel" typically comprises fatty acid esters of ethanol or more commonly methanol. Two principal routes used to prepare fatty acid alkanol esters are transesterification starting with another fatty acid ester (often a naturally occurring ester with glycerol) and direct esterification starting with the fatty acid. A variety of methods are known for these routes. For example, direct esterification can be accomplished by contacting a fatty acid with an alkanol in the presence of a strong acid catalyst such as sulfuric acid. Transesterification can be accomplished by contacting a starting fatty acid ester with the alcohol in the presence of a strong acid catalyst such as sulfuric acid but more commonly a strong base such as sodium hydroxide.

Also useful as water-immiscible liquid carriers for liquid compositions of the present invention are alkoxylated fatty acid esters, including alkoxylated fatty acid glycerides. Besides utility as liquid carriers, alkoxylated fatty acid esters also are useful as surfactants and can self-emulsify. Polyalkoxylated triglycerides (also known as alkoxylated triglycerides, alkoxylated fatty acid glycerides, and polyalkoxylated fatty acid glycerides) are often regarded as "semi-natural" surfactants, as they are usually made from alkoxylation (e.g., ethoxylation or propoxylation) of glycerol fatty acid esters (i.e. fatty acid esters of glycerol) of natural origin such as vegetable oils (many of which are also referred to as seed oils). Alkoxylation refers to the insertion of oxyethylene units having the formula "—$OCH_2CH_2$—", which may be optionally substituted with alkyl, (i.e. alkoxyl units) into ester molecules. The more specific terms "ethoxylation" and "propoxylation" refer, respectively, to insertion of oxyethylene units and oxypropylene (i.e. methyl-substituted oxyethylene) units. Polyalkoxyated triglycerides are thus generally recognized to comprise oxyethylene units, optionally alkyl-substituted, interposed between the glycerol backbone and the fatty acid-derived ester substituents. More specifically, polyethoxylated triglycerides comprise unsubstituted oxyethylene units. In a polyalkoxylated triglyceride molecule, chains of optionally alkyl-substituted oxyethylene units are interposed between the glycerol backbone and one or more of the three fatty acid-derived ester substituents. Polyalkoxylated triglycerides typically contain from about 3 to about 100, more typically from about 5 to about 50 and most typically from about 10 to about 30, units derived from one or more alkylene oxides such as ethylene oxide or propylene oxide. Typically the units are derived from ethylene oxide, propylene oxide or combinations thereof, and most typically the units are derived from ethylene oxide.

In one method, glycerol fatty acid esters (e.g., vegetable oils) are polyethoxylated in a process typically involving heating with a catalytic amount of an alkali metal hydroxide or alkoxide, optionally a catalytic amount of an alcohol (e.g., glycerol), and an amount of ethylene oxide depending upon the extent of ethoxylation desired. These conditions apparently ethoxylate glycerol-based alcohol moieties with ethylene oxide to form ethoxylated species (typically comprising multiple ethylene oxide-derived units in a chain), which condense at the terminal end of the ethylene oxide-derived chain with carboxylic moieties to form ester linkages (e.g., through base-catalyzed transesterification), thereby liberating further glycerol-based alcohol moieties, which are then ethoxylated and condensed with carboxylic moieties to form esters. Ethoxylation continues until the quantity of ethylene oxide added is consumed. Under these conditions, hydroxyl groups on alkyl or alkenyl chains of a carboxylic acid (e.g., ricinoleic acid in castor oil) may also be ethoxylated. Preparation of ethoxylated fatty acid esters (including polyethoxylated triglycerides) by this method are described in GB Patent 1,050,497 and U.S. Pat. No. 6,103,770. Although this method is useful for preparing the polyalkoxylated triglyceride component for the present composition, alkoxylation of fatty esters using metal hydroxides or alkoxides can leave a significant portion of the starting fatty esters unalkoxylated, as is reported by Cox and Werasooriya, *Journal of the American Oil Chemists' Society* 1997, 74(7), 847-859. Furthermore, depending upon reaction conditions, significant amounts of alkoxylated fatty acid (also known as fatty acid alkoxylate) impurities can form.

In one embodiment of the present composition the amount of unmodified (e.g., unalkoxylated) triglycerides is minimized. For this embodiment the polyalkoxylated triglyceride component in the liquid carrier is prepared by processes minimizing residual unmodified triglycerides. An ethoxylation process minimizing residual unmodified triglycerides involves heating glycerol fatty acid esters (i.e. triglycerides) with ethylene oxide in the presence of a calcined or hydrophobicized (e.g., fatty-acid-modified) hydrotalcite heterogeneous catalyst as described in U.S. Pat. No. 5,292,910 and PCT Patent Publication WO 90/13533, particularly in the presence of a co-catalyst (e.g., lithium hydroxide, alkaline earth metal salts, tin salts) as described in U.S. Pat. No. 6,008,392. Ethoxylation using a calcined or hydrophobicized hydrotalcite heterogeneous catalyst also minimizes formation of alkoxylated (e.g., ethoxylated) fatty acid impurities. Cox and Werasooriya, *Journal of the American Oil Chemists' Society* 1997, 74(7), 847-859 discloses another ethoxylation process minimizing residual unmodified triglycerides by use of a calcium and aluminum alkoxyethoxylate catalyst prepared as described in U.S. Pat. No. 4,775,653.

In each of the above described alkoxylation processes, glycerol fatty acid esters can be propoxylated by substituting propylene oxide for all or part of the ethylene oxide in alkoxylation procedures. Furthermore, glycerol fatty acid esters can be alkoxylated using other alkylene oxides (e.g., butylene oxide).

Examples of additional organic compounds that are useful as liquid carriers in the composition of the present invention include: aromatic hydrocarbons, dearomatized aliphatics, alkylbenzenes, alkylnaphthalenes, ketones (e.g., cyclohexanone, 2-heptanone, isophorone and 4-hydroxy-4-methyl-2-pentanone), esters (e.g., isoamyl acetate, hexyl acetate, heptyl acetate, octyl acetate, nonyl acetate, tridecyl acetate and isobornyl acetate, including glycerol esters (e.g. glycerol triacetate) and esters such as alkylated lactate esters, dibasic esters and γ-butyrolactone), alcohols, which can be linear, branched, saturated or unsaturated, (e.g., n-hexanol, 2-ethylhexanol, n-octanol, decanol, isodecyl alcohol, isooctadecanol, cetyl alcohol, lauryl alcohol, tridecyl alcohol, oleyl alcohol, cyclohexanol, tetrahydrofurfuryl alcohol, diacetone alcohol and benzyl alcohol) and limonene. Additional liquid carriers are described in Marsden, *Solvents Guide,* 2nd Ed., Interscience, New York, 1950.

As already mentioned, suspo-emulsion compositions comprise a continuous liquid phase formed by an aqueous liquid carrier in which particulates (e.g., of a solid form of Compounds 1) are dispersed or suspended, and furthermore a water-immiscible liquid component is emulsified in the aqueous carrier. The term "water-immiscible liquid component" as used herein particularly refers to a water-immiscible liquid comprising one or more water-immiscible organic compounds in a total amount of at least about 50%, more typically at least about 60%, 70%, 80%, 90% or 95% of the carrier by weight. The one or more water-immiscible organic compounds forming the water-immiscible liquid component for the present invention (e.g., suspo-emulsion formulations) are typically soluble in water to an extent of less than about 1%, or less than about 0.1%, or less than about 0.01% by weight at 20° C. Particularly useful for the suspo-emulsion compositions of the present invention are water-immiscible liquid components comprising at least one substance selected from the group consisting of glycerol esters of fatty acids (e.g., vegetable and animal-sourced oils), lower alkyl esters of fatty acids (alternatively named fatty acid esters of lower alkanols) and mineral oils. These water-immiscible organic compounds (substances) have already been described in the above disclosure of water-immiscible liquid carriers.

The solid and liquid compositions of the present invention often include one or more surfactants. "Surfactant" is an abbreviation for surface active agent, reflecting the tendency to absorb at surfaces and interfaces. Surfactant molecules typically consist of at least two parts, one that is soluble in a specific solvent, or mixture of solvents (lyophilic), and one that is insoluble (lyophobic). When water is the solvent, the water-insoluble and water-soluble portions of the surfactant are referred to as the hydrophobic and hydrophilic portions, respectively. The hydrophobic or non-polar portion is usually oil or solvent-soluble. The polar portion, or "head" group, typically confers a degree of water-solubility to the surfactant, and can be ionic or non-ionic. The relative size of the hydrophobic and hydrophilic groups, in large part, determines the surface-active properties of the surfactant.

Considering the type and number of functional groups available to form the hydrophilic portion of a surfactant molecule, surfactants are often classified as being non-ionic, anionic or cationic. Non-ionic surfactants have a polar functional group or groups that do not ionize on contact with water. Non-ionic surfactants useful for the present compositions include, but are not limited to: linear and branched alcohols, alkylphenols, fatty acids, glycols, amines or other compounds and the products resulting from their alkoxylation (e.g., ethoxylations, propoxylation), including products based on natural and synthetic alcohols, and mixtures thereof; alkylpolysaccharides; amine ethoxylates, alkanolamides and ethoxylated alkanolamides; alkoxylated triglycerides (e.g., ethoxylated soybean, castor and rapeseed oils); alkylphenol alkoxylates (e.g. octylphenol ethoxylates, nonylphenol ethoxylates, dinonyl phenol ethoxylates and dodecyl phenol ethoxylates prepared from the phenols and ethylene oxide, propylene oxide, butylene oxide or mixtures thereof); polymeric random, graft and block polymers prepared from ethylene oxide or propylene oxide and reverse block polymers where the terminal blocks are prepared from propylene oxide; acrylic, acrylate/methacrylate and acrylic/styrene graft copolymers, optionally containing polyoxyethylene or polyoxypropylene; ethoxylated fatty acid and/or oils (e.g., ethoxylated methyl esters); ethoxylated tristyrylphenols, (e.g., those prepared from ethylene oxide, propylene oxide, butylene oxide or mixtures thereof); fatty acid esters, glycerol esters, lanolin-based derivatives, sorbitan and sorbitol esters and their corresponding alkoxylates (e.g., polyethoxylated sorbitan fatty acid esters, polyethoxylated sorbitol fatty acid esters and polyethoxylated glycerol fatty acid esters and other sorbitan derivatives such as sorbitan esters); polyalkylene oxide block copolymers; polyethylene glycol copolymers; alkyd peg (polyethylene glycol) resins, graft or comb polymers and star polymers; methylmethacrylate graft copolymers; butyl and isobutyl methacrylates; ethylene acrylate; ethylene/maleic anhydride; ethylene vinyl acetate copolymers and the like; polyethylene glycols (pegs); polyethylene glycol fatty acid esters; silicone-based surfactants; and sugar-derivatives such as sucrose esters, alkyl polyglycosides where the number of glucose units, (or other sugar units) referred to as degree of polymerization (D.P.), can range from 1 to 3 and the alkyl units can range from $C_6$ to $C_{14}$ (see *Pure and Applied Chemistry* 72, 1255-1264), and alkyl polysaccharides.

Nonionic surfactants often involve alkoxylation such as ethoxylation or propoxylation. As is well known in the art, the term "ethoxylation" and "propoxylation" refers to the process that results in the formation or appendage of chains comprising one or more oxyethylene (—OCH$_2$CH$_2$—) or oxypropylene (—OCH$_2$CH$_2$CH$_2$—) units formed by reaction of ethylene or propylene oxide with hydroxyl groups on present on the target chemistry resulting in its esterification, e.g. alkylphenol conversion to alkylphenol ethoxylate. If more than one oxyethylene unit is generally present on each surfactant molecule, "polyoxyethylene" can be included in the surfactant name, or alternatively a POE (polyoxyethylene) number can be included in the name to indicate the average number of oxyethylene units per molecule.

Anionic surfactants are surface-active molecules in which the hydrophilic group connected to the lipophilic portion of the molecule forms a negative ion (i.e. anion) when placed in aqueous solution. Charge bearing hydrophilic groups commonly found in anionic surfactants include: carboxylates, sulfates, sulfonates and phosphates.

Useful anionic surfactants include, but are not limited to: sulfonic acids, sulfates and sulfonates (e.g., alkylaryl sulfonic acids and their salts), alkylbenzene sulfonates and their derivatives, styryl phenol ether sulfates and sulfonates of oils and fatty acids, diphenyl sulfonate derivatives, lignin and lignin derivatives such as lignosulfonates, olefin sulfonates, styryl phenol ether sulfate, sulfates and sulfonates of oils and fatty acids, sulfates and sulfonates of ethoxylated alkylphenols, sulfates of alcohols, sulfates of ethoxylated alcohols, sulfonates of amines and amides such as N,N-alkyltaurates; carboxylated alcohol or alkylphenol ethoxylates, ethoxylated alkylphenols, alcohols, ethoxylated alcohols, carboxylated alcohol or alkylphenol ethoxylates; diphenyl sulfonate derivatives; lignin and lignin derivatives such as lignosulfonates; maleic or succinic acids or their anhydrides; olefin sulfonates; phosphate esters (e.g., phosphate esters of alcohol alkoxylates, phosphate esters of alkylphenol alkoxylates and phosphate polymeric surfactants such as random copolymers, block copolymers); styryl phenol ethoxylates; protein-based surfactants; sarcosine derivatives; styryl phenol ether sulfate; sulfonates of benzene, cumene, toluene, xylene, and dodecyl and tridecylbenzenes; sulfonates of condensed naphthalenes; sulfonates of naphthalene and alkyl naphthalene; sulfonates of fractionated petroleum; sulfosuccinamates; and sulfosuccinates and their derivatives such as dialkyl sulfosuccinate salts.

A cationic surfactant is a surface-active molecule in which the hydrophilic group connected to the lipophilic portion of the molecule forms a positive ion (i.e. cation) when placed in aqueous solution.

Useful cationic surfactants include, but are not limited to: amides and ethoxylated amides; amines such as N-alkyl propanediamines, tripropylenetriamines and dipropylenetetramines, and ethoxylated amines, ethoxylated diamines and propoxylated amines (prepared from the amines and ethylene oxide, propylene oxide, butylene oxide or mixtures thereof); amine salts such as amine acetates and diamine salts; quaternary ammonium salts such as quaternary salts, ethoxylated quaternary salts and diquaternary salts; and amine oxides such as alkyldimethylamine oxides and bis-(2-hydroxyethyl)-alkylamine oxides.

Nonionic, anionic and cationic surfactants and their recommended uses are disclosed in a variety of published references including *McCutcheon's Emulsifiers and Detergents*, annual American and International Editions published by McCutcheon's Division, The Manufacturing Confectioner Publishing Co.; Sisely and Wood, *Encyclopedia of Surface Active Agents*, Chemical Publ. Co., Inc., New York, 1964; and A. S. Davidson and B. Milwidsky, *Synthetic Detergents*, Seventh Edition, John Wiley and Sons, New York, 1987.

Surfactants are often classified as wetting agents or dispersants. Alternatively, depending on the intended use, surfactants are also classified by a measure of the balance between their polar and non-polar groups, by a value known as the hydrophile-lipophile balance (HLB).

When added to water or an aqueous liquid, surfactants that substantially reduce the surface tension of the liquid are typically referred to as wetting agents, even though they may also function as dispersants. Surfactants that have a minimal affect on surface tension but effectively disperse particulates are typically categorized as dispersants. Dispersants can reduce the tendency of solid particles to stick together either in the present composition before dilution or after dilution with water. Particles sticking together may result in flocculation (i.e. particles loosely sticking together) or coagulation (i.e. particles irreversibly agglomerating). Dispersants, also called dispersing agents or dispersing component, can reduce attractive forces between particles in close proximity. In the present disclosure and claims, the ability to disperse particulates in a continuous liquid phase is termed "a dispersant property". A surfactant component (e.g., in formulated compositions) that comprises as a constituent at least one dispersant or another surfactant having a dispersant property in addition to other surfactant properties is a surfactant component having a dispersant property.

A wide variety of dispersants are known in the art of formulation, including those described in *McCutcheon's Detergents and Emulsifiers Annual*, Allured Publ. Corp., Ridgewood, N.J., as well as Sisely and Wood, *Encyclopedia of Surface Active Agents*, Chemical Publ. Co., Inc., New York, 1964. Examples of dispersants include lignosulfonates, formaldehyde condensates of naphthalenesulfonates or alkylnaphthalenesulfonates (e.g., MORWET D425), condensed methylnaphthalenesulfonates (e.g., SUPRAGIL MNS/90), anionic condensation products of alkylphenol, formaldehyde and optionally sodium sulfite, salts of polycarboxylic acids (e.g., polyacrylic acids), phosphate esters of tristyrylphenol ethoxylates (e.g., SOPROPHOR 3D33), alkoxylated alcohols (e.g., SYNPERONIC A11), polyoxyethylene/polyoxypropylene block polymers (e.g., PLURONIC F108, ATLOX 4912, ATLAS G-5000, SYNPERONIC PE series copolymers), ethylene oxide-propylene oxide based polycarboxylic acid graft copolymers such as methyl methacrylate graft copolymers (e.g., ATLOX 4913) and poly-12-hydroxystearic acid graft copolymers, for example, with polyethylene glycol (e.g., ATLOX 4912), and polyethylene glycol alkyd resins (e.g., ATLOX 4914). Polymeric dispersants, such as ATLOX 4912, ATLOX 4914 and the ammonium salt of an ethoxylated styrylphenyl ether sulfate, also have weak emulsifier properties allowing them to function as emulsion stabilizers after a suspo-emulsion is formed using high-energy/high-shear mixing equipment.

Of note as particularly useful chemical classes of dispersants for aqueous compositions (e.g., aqueous suspension concentrates, suspo-emulsions) of the present invention are alkoxylated alcohols, methyl methacrylate graft copolymers, block copolymers based on poly-12-hydroxystearic acid and polyethylene glycol, and polyethylene oxide-polypropylene oxide block copolymers. Polyethylene glycol alkyd resins are of note as dispersants for non-aqueous compositions, because in addition to having a dispersant property, they also have a significant emulsifier property, which helps emulsify the water-immiscible carrier of the compositions after dilution with water (e.g., in a spray tank).

In addition to their ability to wet surfaces and disperse particles, surfactants can also be useful as emulsifiers. One measure of the balance between the polar and non-polar portions of a surfactant, given by a quantity called the hydrophile-lipophile balance (HLB), has been found to be extremely useful in selecting surfactants for use as emulsifiers. The HLB is an empirical quantity that is represented by a scale where the least hydrophilic materials have lowest HLB numbers. Increasing HLB corresponds to increasing hydrophilic character. The determination of HLB is done by various techniques and is available from many sources, including surfactant supplier product literature and standard surfactant texts. Surfactants with HLB values of approximately <6 are mostly water-insoluble and give unstable dispersions in water; surfactants with HLB values of approximately 6-10 form milky dispersions in water; surfactants with HLB values of approximately >10 are soluble and give translucent or clear solutions in water.

Surfactants that are useful as emulsifiers typically reside at the oil-water interface with their lipophilic portion immersed in the water-immiscible liquid droplets and their hydrophilic portion penetrating the surrounding aqueous phase, thereby causing reduction of surface tension. Emulsifiers (emulsifier component) can prevent the coalescence of water-immiscible liquid droplets in water and thus help maintain stable dispersions of water-immiscible liquid droplets in aqueous phase, which are known as emulsions. Emulsifiers are particularly relevant to liquid compositions of the present invention that are suspo-emulsions or suspension/dispersion concentrates that on dilution with water form suspensions of particles of a solid form of Compound 1 and also an emulsion of liquid droplets comprising other components (e.g., adjuvants, other active ingredients). In the present disclosure and claims, the ability to emulsify a liquid in a continuous liquid phase is termed "an emulsifier property". A surfactant component (e.g., in formulated compositions) that comprises as a constituent at least one emulsifier or another surfactant having an emulsifier property in addition to other surfactant properties is a surfactant component having an emulsifier property.

Of note as particularly useful chemical classes of emulsifiers for liquid compositions of the present invention comprising a water-immiscible liquid component emulsified in an aqueous carrier (e.g., suspo-emulsions) are calcium dodecylbenzene sulfonates, ethoxylated tallowamine sulfates, ethoxylated non-ionic surfactants (e.g. ethoxylated castor oil and ethoxylated tristyrlphenols), fatty acid hexaesters of ethoxylated sorbitol, ethoxylated castor oil and alkyl polyglycosides. Of note as particularly useful classes of emulsifiers for non-aqueous compositions that emulsify on dilution with water (e.g., in a spray tank) are calcium dodecylbenzene sulfonate and blends of calcium dodecylbenzene sulfonate with ethoxylated tallowamine sulfates and ethoxylated non-ionic surfactants (e.g. ethoxylated castor oil and ethoxylated tristyrlphenols), alkyl polyglycosides, fatty acid hexaesters of ethoxylated sorbitol and fatty acid triesters of sorbitan. Polyethylene glycol alkyd resins are also of note as surfactants for such non-aqueous compositions, because in addition to having a dispersant property, they also have a significant emulsifier properties as well as utility as deposition aids.

Also useful for the present compositions are surfactants that have been found to be useful as antifoams and defoamers. Of particular note as antifoams for the compositions of the present invention are polydimethylsiloxane emulsions in water.

Compositions of this invention may also contain formulation auxiliaries and additives, known to those skilled in the art as formulation aids (some of which may be considered to also function as solid diluents, liquid diluents or surfactants). Such formulation auxiliaries and additives may control: pH (buffers or pH-buffer component), foaming during processing (antifoams, defoamers or antifoam component), sedimentation of the active ingredients during storage (suspending agents or suspending agent component), viscosity (thickeners or viscosity builders), in-container microbial growth (antimicrobials or biocide component), product freezing (antifreezes or antifreeze component), color (dyes and pigments), wash-off (film formers or stickers), evaporation (evaporation retardants), and other formulation attributes. Examples of formulation auxiliaries and additives include those listed in *McCutcheon's Volume 2: Functional Materials*, annual International and North American editions published by McCutcheon's Division, The Manufacturing Confectioner Publishing Co.; and PCT Publication WO 03/024222.

The liquid compositions of the present invention particularly benefit from including one or more formulation agents described herein as "suspending agents". Suspending agents include thickeners and structuring agents. Thickeners are organic or inorganic liquid or solid additives that increase the viscosity of aqueous or non-aqueous dispersions. Structuring agents impart structure to aqueous or non-aqueous dispersions. Increasing the viscosity or structuring the dispersion in turn "stabilizes" the formulation by slowing, minimizing or eliminating the sedimentation of the active ingredient and/or reducing the rate and degree of phase separation that occurs during storage. Many suspending agents increase both viscosity and structure. An extensive list of thickeners and their applications can be found in *McCutcheon's 2005, Volume 2: Functional Materials* published by MC Publishing Company.

Suspending agents can be added to formulations for many reasons, e.g., to affect the pouring and dispersing properties of a formulation. However, the two primary reasons for their use are to inhibit the formation of sediment and the development of an undesirable amount of phase separation, both of which can be perceived as a sign of poor quality. Sedimentation and phase separation usually occur in dispersions where the viscosity is too low to effectively hinder the settling rate of the active ingredient and/or where there is antagonistic or insufficient interaction between the particulates of the dispersion (i.e. active ingredient and structuring agents) to form a stabilized and self-supporting network of particulates. Suspension concentrate (SC), suspo-emulsion (SE) and oil dispersion (OD) compositions are desirably stabilized to an extent where no more than a trace of sediment forms at the bottom of their container and no more than about 5 percent phase separation is visible after 18 months to two years of storage. However, depending on the nature of the sediment and ease with which the SC, SE, or OD can be reconstituted (e.g., a few inversions of the container), sediments of up to several millimeters and phase separation of up to about 20 percent can also be considered acceptable.

Suspending agents are typically included in SC, SE and OD compositions and many have been found to be effective at low concentrations. For example, polysaccharides can thicken the continuous aqueous phase of an SC or SE composition when added in an amount less than 0.5%; amounts less than about 0.2% are typical of commercial quality products currently on the market.

Suspending agents from the class of materials known as clays, organically modified clays, silica and organically modified silicas work well alone or in combination with the other components in the compositions of the present invention. The terms "clay" and "silica" in the present invention relate to naturally occurring materials composed primarily of fine-grained minerals that exhibit one or both characteristics of (1) plasticity when wet or (2) hardening when dried and/or fired. Without being bound by any particular theory, clays, organically modified clays, silica and organically modified silica are believed to increase viscosity through formation of a loose network structure comprising dispersed clays, organically modified clays, silica and organically modified silica particles, which are held together by hydrogen bonding and/or long-range electrostatic forces.

Clays are often classified as being in one of three primary groups: kaolinite, montmorillonite-smectite, and illite. Most "natural" clays are mixtures of these different types, along with other weathered minerals. Although the composition of clays can vary, many of their properties result from their fine particle size, e.g., absorbency, binding or stickiness once wetted and dried, plasticity when wet, the ability to form colloidal suspensions when dispersed in water, and the tendency to flocculate in water of various hardness, i.e. electrolyte content. The wide range of unique properties makes them useful in both solid and liquid formulation types.

Bentonite clays, for example, are smectites formed primarily from the alteration of volcanic ash. They swell on exposure to moisture and have the ability to absorb water and other materials on contact. Similarly, attapulgite clays are naturally occurring crystalline hydrated magnesium aluminosilicates that produce a three-dimensional chain structure that provides unique sorptive properties, making them useful as diluents, binders and absorbents in solid compositions, e.g., wettable powders, water dispersible granules, extruded granules.

Bentonite clays are also readily dispersible in water, and have the ability to form colloidal suspensions when dispersed in water and the tendency to flocculate in water depending on its hardness, i.e. electrolyte content. These properties make bentonites clays useful as structuring agents in aqueous suspension concentrates, suspo-emulsions and also in oil dispersions, depending on the polarity of the water-immiscible liquid carrier.

Attapulgite clays are naturally occurring crystalline hydrated magnesium aluminosilicates that produce a three-dimensional chain structure that results in unique colloidal properties in both aqueous and water-immiscible liquid carriers. These properties make attapulgite clays useful as structuring agents in aqueous suspension concentrates, suspo-emulsions and oil dispersions.

Bentonite clays that have been "organically modified" by reacting organic cations, such as a quaternary ammonium, with the surface of the sodium salt of the bentonite clay are also particularly suitable for use in thickening oil dispersions by forming a structured network of bentonite particles. The reaction changes the nature of the surface of the clay particles from hydrophilic to hydrophobic (alternatively described as oleophilic). This functionalization of the surface of the clay particles gives these clays the ability to impart various rheological characteristics to solvent-based or oil-based formulations to which they are added.

Particularly useful clays suitable for use in the aqueous suspension concentrates, suspension concentrate seed coating compositions, suspo-emulsions and oil dispersions of the present invention include but are not limited to: attapulgite clays, such as Attagel® 40 (BASF Corp.) and Attagel® 50 (BASF Corp.). Particularly useful clays suitable for use in the oil dispersion compositions of the present invention also include but are not limited to: organically modified bentonites, such as Garamite® 1458 (Southern Clay Products, Inc.), Bentone® 760 (Southern Clay Products, Inc.), Claytone® 40 (Southern Clay Products, Inc.) and Tixogel® EZ100 (Southern Clay Products, Inc.).

Silica is white or colorless crystalline substance consisting of silicon dioxide ($SiO_2$), which is found abundantly as quartz, sand, flint, agate and many other minerals, and used in many industries to manufacture a wide variety of materials, especially glass and concrete. Silica particles typically have free silanol (Si—OH) groups on their surface making them hydrophilic.

Commercially available silica compositions are manufactured by precipitation, spray drying or high temperature flame hydrolysis (fumed silica). The surface and size of the silica particles is dependent upon the particular manufacturing process. Variations of surface and size of silica particles in turn alter the properties and functionality of the silica interacting with the aqueous and water-immiscible liquid carriers of the present invention.

Fumed silica has properties most suitable for the compositions of the present invention. Fumed silica is hydrophilic due to the free silanol (Si—OH) groups on the surface of its particles. Fumed silica also comprises submicron particle aggregates with surface area exceeding 100 $m^2/g$. The submicron particle size, nature of the surface and large surface area of fumed silica together promote the development of a structured network and an accompanying increase in the viscosity of the liquid compositions of the present invention. Furthermore, the hydrophilic nature of fumed silica has been found to remain functional even in compositions comprising water-immiscible liquid carriers, e.g., oil dispersions, provided that the water-immiscible liquid carrier has sufficient polarity to enable the formation of a loose network structure and subsequent increase in viscosity. Such loose network structures are thought to occur as a result of the ability of silica particles to interact through hydrogen bonding and/or long-range electrostatic forces.

While coarser precipitated or spray dried silica can also be used in the compositions of the present invention, better results can be achieved with fumed silica especially when deagglomerated by wet milling or other means of size reduction or comminution.

Another advantage of hydrophilic fumed silica is that it has a slightly acidic pH, for example pH 4-6 for Aerosil® 200 (Evonik Degussa, GmbH), which helps prevent chemical degradation of base-sensitive fungicides and crystal growth resulting from an unacceptable increase in solubility of fungicides that can be formulated together with Compound 1 and whose solubility increases as the pH of the composition increases, e.g., cymoxanil.

For these reasons, fumed silica is the preferred form of silica for use in preparing the suspo-emulsion, suspension concentrate and in oil dispersion compositions of the present invention. A particularly useful fumed silica for preparing the compositions of the present invention is Aerosil® 200 (Evonik Degussa, GmbH).

Silica can also be rendered hydrophobic by capping the free silanol groups on the particle surface with hydrophobic groups, e.g., by reacting them with chlorotrimethylsilane, or 1,1,1,3,3,3-hexamethyldisilazane. Such surface treatments result in "organically modified silicas" that are suitable for use in compositions where a water-immiscible liquid carrier provides the continuous liquid phase of the suspension, e.g., oil dispersion compositions of the present invention. A particularly useful hydrophobically modified silica for preparing the compositions of the present invention is Aerosil® R972 (Evonik Degussa, GmbH).

To obtain a viscosity and structured network adequate to stabilize the compositions of the present invention, use of a single suspending agent may not be sufficient, because both an increase in viscosity and structuring of the suspension or dispersion is desired. To some extent, this problem can be overcome in formulations containing a water-immiscible liquid carrier by the addition of 0.1 to about 3% by weight of at least one protic solvent, such as water, a $C_1$-$C_{12}$ alkanol (straight or branched chain) or a $C_2$-$C_3$ glycol, which "activates" the surface of a hydrophilic silica and thereby provides sufficient structure and viscosity to stabilize the composition. Without being bound by any particular theory, one possible explanation for the activation of a hydrophilic silica by the addition of a protic solvent is that protic solvents transfer protons ($H^+$) to the silanol (Si—OH) surface groups on the silica, which allows the silica particles to develop a charge, which in turn extends the range of interactive forces between silica particles, thereby increasing the viscosity and extent of the particle-particle interaction resulting in a structured particle network capable of stabilizing the dispersion.

Of note is a liquid composition of the present invention comprising fumed silica and a protic solvent selected from water, methanol, ethanol and ethylene glycol. However, for reasons of cost and environmental safety, in oil dispersion compositions wherein a protic solvent is added, water is preferred.

Other suspending agents that can be used alone or in combination to increase viscosity or impart structure include polymers soluble in the liquid carrier. High molecular weight polysaccharides are useful suspending agents in compositions wherein water forms the liquid carrier. Surfactants included the liquid compositions of the present invention to promote dispersion and/or emulsification often interact cooperatively with suspending agents to reduce the settling tendency of particles of solid forms of Compound 1.

The amorphous solid form of Compound 1 can be incorporated into solid (sometimes termed "dry") compositions of the present invention by first dissolving Compound 1 in a solvent, applying the solution to a solid carrier, and then evaporating the solvent. Crystalline forms of Compound 1 (e.g., polymorph Forms A and B), including their mixtures with other active ingredients, are typically incorporated into the solid compositions of the present invention by first grinding the solid form of Compound 1 in the presence of a liquid or dry diluent. Solid formulations are often prepared using dry milling processes, which produce average particle diameters in the 2 to 10 μm range. Solid formulations may also be prepared using liquid milling processes followed by removal of the liquid, usually water, using technologies such as spray drying. Solid formulations can also be prepared by combining dry milling with the incorporation of water and/or other suitable liquid(s) to form a paste suitable for extrusion, pan or fluid bed granulation, or other agglomeration technique, where a drying step is often but not always required to reach the desired composition, size, shape and physical properties of the intended formulation. Dusts and powders can be prepared by blending and usually grinding (such as with a hammer mill or fluid-energy mill). Granules and pellets can be prepared by spraying the active material upon preformed granular carriers or by agglomeration techniques. For further information regarding agglomeration techniques, see Browning, "Agglomeration", *Chemical Engineering*, Dec. 4, 1967, pp 147-48, *Perry's Chemical Engineer's Handbook*, 4th Ed., McGraw-Hill, New York, 1963, pages 8-57 and following, and WO 91/13546. Often, aqueous slurries can also be prepared using suspension concentrate techniques (see, for example, U.S. Pat. No. 3,060,084), then further processed by spray drying to form the a dry composition, e.g. wettable powder or water-dispersible granules. Pellets can be prepared as described in U.S. Pat. No. 4,172,714. Water-dispersible and water-soluble granules can be prepared as taught in U.S. Pat. Nos. 4,144,050, 3,920,442 and DE 3,246,493. Tablets can be prepared as taught in U.S. Pat. Nos. 5,180,587, 5,232, 701 and 5,208,030. Films can be prepared as taught in GB 2,095,558 and U.S. Pat. No. 3,299,566.

Methods for making suspensions and dispersions of particles in liquids are well known and include ball-milling, bead-milling, sand-milling, colloid milling or air-milling combined with high-speed blending. Preparation of the dispersions and suspensions of particles in the present liquid compositions (e.g., aqueous suspension concentrates, oil dispersions, suspo-emulsions) typically involve first making a slurry of a solid form of Compound 1 and one or more of the other formulating ingredients. For preparing aqueous suspension concentrate formulations, all ingredients other than the active ingredient (e.g., a solid form of Compound 1) are typically first combined with the water, and then the active ingredient is added to form the slurry. Preparation of suspo-emulsions can begin with preparation of the aqueous suspension concentrate portion of the suspo-emulsion, and the water-immiscible liquid component and emulsifier are added after the desired particle size of the solid form of Compound 1 is achieved through milling. Depending on the particle size of the solid form of Compound 1 and any other active ingredients, an initial pre-milling step may be used to reduce the dimensions of the particle in the slurry to less than a millimeter prior to media milling. Such techniques include dry and wet milling steps, e.g., colloid milling of the coarse particulate slurry prior to media milling, or hammer milling of the active ingredient and/or mixture of the active ingredient and one or more of the formulation components, such as silica or clay.

Once the target average particle size of slurry is decided, the proper size milling media (e.g., glass or ceramic) can be charged to the media mill and the rate of flow through the media mill set to optimize the rate of particle size reduction. Best practices for the media-milling of slurries are well known in the art. For preparing aqueous suspension concentrate formulations, the mill typically contains glass or ceramic media in a size range of about 0.8 to 1.0 mm. If the functionality of the suspending agent degrades under the high shear that accompanies media milling, the suspending agent can be added after or towards the end of the media-milling step. In the liquid compositions of the present invention, a solid form of Compound 1 is typically reduced to average particle diameters of less than ~3 μm. Average particle diameter is preferably less than ~2 μm and more preferably less than ~1 μm to provide best biological availability of the active ingredient. Average (i.e. mean) particle diameter is the volume moment mean, also known as the volume mean and the De Broucker mean. The principles of particle size analysis are well known to those skilled in the art; for a technical paper providing a summary, see A. Rawle, "Basic Principles of Particle Size Analysis" (document MRK034 published by Malvern Instruments Ltd., Malvern, Worcestershire, UK).

For preparation of suspo-emulsion compositions, after the aqueous portion of the composition is milled to achieve the desired average particle diameter of active ingredient (i.e. a solid form of Compound 1 optionally mixed with other solid active ingredients), the water-immiscible liquid and emulsifier components (usually pre-blended) are typically added with stirring to complete preparation of the suspo-emulsion. Suspo-emulsion compositions can be prepared without including surfactants considered to be primarily emulsifiers by including polymeric surfactants known to be dispersants and using high-energy/high-shear mixing equipment.

A solid form of Compound 1 in a solid or liquid composition of the present invention can also be present in an encapsulated or micro-encapsulated form to protect Compound 1 from an incompatible formulating ingredient or to control or delay release of Compound 1 after application of the composition.

For further information regarding the art of formulation, see T. S. Woods, "The Formulator's Toolbox—Product Forms for Modern Agriculture" in *Pesticide Chemistry and Bioscience, The Food-Environment Challenge*, T. Brooks and T. R. Roberts, Eds., Proceedings of the 9th international Congress on Pesticide Chemistry, The Royal Society of Chemistry, Cambridge, 1999, pp. 120-133. See also U.S. Pat. No. 3,235,361, Col. 6, line 16 through Col. 7, line 19 and Examples 10-41; U.S. Pat. No. 3,309,192, Col. 5, line 43 through Col. 7, line 62 and Examples 8, 12, 15, 39, 41, 52, 53, 58, 132, 138-140, 162-164, 166, 167 and 169-182; U.S. Pat. No. 2,891,855, Col. 3, line 66 through Col. 5, line 17 and Examples 1-4; Klingman, *Weed Control as a Science*, John Wiley and Sons, Inc., New York, 1961, pp 81-96; Hance et al., *Weed Control Handbook*, 8th Ed., Blackwell Scientific Publications, Oxford, 1989; and *Developments in formulation technology*, PJB Publications, Richmond, UK, 2000.

The following formulation examples are presented to further illustrate but not limit the disclosure in any way whatsoever. All percentages are given by weight and all formulations are prepared using conventional techniques. Without further elaboration, it is believed that one skilled in the art using the preceding descriptions and references can utilize the present invention to its fullest extent.

FORMULATION EXAMPLE 1

| High Strength Concentrate | |
|---|---|
| polymorph Form B of Compound 1 | 75% |
| precipitated spray dried silica | 24% |
| synthetic amorphous fine silica | 1% |

High-strength compositions are prepared by mixing and dry milling to form an intermediate for subsequent use in preparing a lower strength liquid and solid formulations.

FORMULATION EXAMPLE 2

| Dusts | (a) | (b) |
|---|---|---|
| polymorph Form A of Compound 1 | 5.0% | 8.0% |
| talc | 94.0% | 2.0% |
| kaolin | — | 87% |
| sodium silicoaluminate | 1.0% | — |
| montmorillonite (calcined) | — | 3.0% |

Ready-to-use dusts are obtained by mixing the solid form of Compound 1 with the solid carrier. Dusts can also be prepared by dry milling using a suitable mill, depending on the intended application.

FORMULATION EXAMPLE 3

| Wettable Powder | (a) | (b) | (c) |
|---|---|---|---|
| polymorph Form A of Compound 1 | 25.0% | 60.0% | 75.0% |
| sodium lauryl sulfate | 2.5% | — | — |
| sodium disobutylnaphtalenesulfonate | — | — | 5.0% |
| polyoxyethylene alkyl ether | — | 2.0% | — |
| octylphenol polyethylene glycol ether (7-8 mol ethoxylate) | — | 2.5% | — |
| sodium naphthalene sulfonate | — | 1.5% | — |
| dodecylphenol polyethylene glycol ether | — | — | 2.0% |
| sodium ligninsulfonate | 5.0% | — | 5.0% |
| hydrophilic fumed silica | 2.5% | — | — |
| kaolinite clay | 65.0% | 34.0% | 13.0% |

The solid form of Compound 1 is thoroughly mixed with the formulating ingredients, and the resulting mixture is dry milled using a suitable mill (e.g., hammer-mill, air classifying mill). Wettable powders can be diluted with water to give suspensions of any desired concentration.

FORMULATION EXAMPLE 4

| Granule | (a) | (b) |
|---|---|---|
| amorphous form of Compound 1 | 5.0% | 10.0% |
| hydrophilic fumed silica | 1.0% | — |
| kaolinite clay granules | 94.0% | — |
| attapulgite granules (low volatile matter, 0.71/0.30 mm; U.S.S. No. 25-50 sieves) | — | 90.0% |

Compound 1 is dissolved in methylene chloride, the solution is sprayed onto the solid carrier, and the solvent is then evaporated in vacuo.

FORMULATION EXAMPLE 5

| Coated Granule | (a) | (b) |
|---|---|---|
| granules from Example 4 | 97.0% | 95.0% |
| polyethylene glycol (MW < 1000) | 3.0% | 5.0% |

The granules from Example 4 are moistened, and the polyethylene glycol is uniformly applied while mixing the granules. Dust-free coated granules are obtained in this manner.

FORMULATION EXAMPLE 6

| Water-dispersible Granule | (a) | (b) |
|---|---|---|
| polymorph Form A of Compound 1 | 10% | 50% |
| sodium alkylnaphthalenesulfonate formaldehyde condensate | 2% | 5% |
| ammonium ligonosulfonate | 8% | — |
| ammonium sulfate | 5% | — |
| alkyl sulfonate | — | 3% |
| sodium alkylnaphthalenesulfonate | — | 2% |
| cross-linked homopolymer of N-vinyl-2-pyrrolidone | — | 2% |
| encapsulated silicone | — | 1% |
| kaolinite clay | 75% | 37% |

The WG formulations of Formulation Example 6 are prepared by hammer-milling and/or air milling a mixture of all ingredients followed by granulation (e.g., fluid bed or pan granulation). The dried granules are typically added to a spray tank in the amount needed to produce a spray mix with the desired concentration of active ingredient.

FORMULATION EXAMPLE 7

| Extruded Pellet | (a) | (b) |
|---|---|---|
| polymorph Form A of Compound 1 | 10% | 25% |
| sodium lignonsulfonate | 2% | 5% |
| carboxymethyl cellulose | 1% | 5% |
| anhydrous sodium sulfate | — | 10% |
| crude calcium ligninsulfonate | — | 5% |
| sodium alkylnaphthalenesulfonate | — | 1% |
| kaolinite clay | 87% | — |
| calcium/magnesium bentonite | — | 49% |

The solid form of Compound 1 is mixed with the formulating ingredients and the mixture is ground and moistened with water. This mixture is extruded and then dried in a stream of air.

FORMULATION EXAMPLE 8

| Seed Treatment | |
|---|---|
| polymorph Form B of Compound 1 | 20.00% |
| polyvinylpyrrolidone-vinyl acetate copolymer | 5.00% |
| montan acid wax | 5.00% |
| calcium ligninsulfonate | 1.00% |
| polyoxyethylene/polyoxypropylene block copolymers | 1.00% |
| ethoxylated stearyl alcohol (POE 20) | 2.00% |
| polydimethylsilicone as a 75% aqueous emulsion | 0.20% |
| colorant red dye | 0.05% |
| water | 65.75% |

The solid form of Compound 1 is mixed with the other ingredients in the composition and media milled until the desired particle size is attained. The resulting suspension is applied in its initial concentration or further diluted and sprayed onto a moving bed of the seed in an amount required to achieve the desired weight or thickness of the coating.

FORMULATION EXAMPLE 9

| Aqueous Suspension Concentrate | (a) | (b) | (c) |
|---|---|---|---|
| polymorph Form B of Compound 1 | 10.0% | 20.0% | 40.0% |
| poly-12-hydroxystearic acid/polyethylene glycol block copolymer | — | — | 10.0% |
| propylene glycol | 15.0% | 10.0% | 6.0% |
| sodium ligninsulfonate | 10.0% | 10.0% | 2.0% |
| nonylphenol ethoxylated glycol ether | 6.0% | 6.0% | — |
| carboxymethylcellulose | 1.0% | 1.0% | — |
| polydimethylsilicone as a 75% aqueous emulsion | 0.8% | 0.8% | — |
| polyoxyethylene polyoxypropylene copolymer | — | — | 2.5% |
| aqueous dipropylene glycol solution containing 20% 1,2-benisothiazolin-3-one | 0.2% | — | — |
| polysiloxane emulsion in water | — | — | 0.5% |
| xanthan gum | — | — | 0.1% |
| water | 57.0% | 52.2% | 38.9% |

The solid form of Compound 1 and one or more of the other ingredients of the composition are mixed to form a slurry, followed by further size reduction by wet milling techniques to an average particle diameter of less than ~3 μm and addition of the remaining ingredients, if any.

FORMULATION EXAMPLE 10

| Suspoemulsion | (a) | (b) | (c) |
|---|---|---|---|
| polymorph Form B of Compound 1 | 10.0% | 20.0% | 30.0% |
| methylated seed oil | 25.0% | 30.0% | 30.0% |
| graft copolymer | 2.0% | — | 4.0% |
| propylene glycol | 6.0% | 6.0% | 3.0% |
| sodium lignosulfonate | 4.0% | 6.0% | 1.0% |
| nonylphenol polyethylene glycol ether (15 mole of ethylene oxide) | 6.0% | 6.0% | 6.0% |
| carboxymethylcellulose | 1.0% | 0.6% | — |
| silicone as a 75% aqueous emulsion | 0.8% | 0.8% | 0.5% |
| polyoxyethylene polyoxypropylene copolymer | — | — | 2.5% |
| aqueous dipropylene glycol solution containing 20% 1,2-benisothiazolin-3-one | 0.2% | 0.2% | 0.2% |
| xanthan gum | 0.5 | — | 0.1% |
| water | 44.5% | 30.4% | 22.7% |

The solid form of Compound 1 and one or more of the other ingredients of the composition are mixed to form a slurry followed by further size reduction by wet milling techniques to an average particle diameter of less than ~3 μm and addition of the remaining ingredients, if any.

FORMULATION EXAMPLE 11

| Oil Dispersion | (a) | (b) | (c) |
|---|---|---|---|
| polymorph Form B of Compound 1 | 10.0% | 15.0% | 20.0% |
| polyoxyethylene polyoxypropylene copolymer | 3.0% | — | — |
| liquid polyalkoxylated aliphatic alcohol | 15.0% | 15.0% | 4.0% |
| ethoxylated sorbitol hexaoleate | 8.5% | 12.0% | 11.0% |

| Oil Dispersion | (a) | (b) | (c) |
|---|---|---|---|
| mixture of calcium alkyl aryl sulfonate fatty alcohol ethoxylates and light aromatics | 5.0% | 5.0% | — |
| sorbitan trioleate | 5.0% | — | — |
| mixture of alkylbenzenes | 32.0% | — | — |
| light-weight mineral oil | — | 52.0% | 49.0% |
| medium-chain-length triglycerides | 20% | — | 15.0% |
| amorphous fumed silica | 1.5% | 1.0% | 1.0% |

The solid form of Compound 1 and one or more of the other ingredients of the composition are mixed to form a slurry followed by further size reduction by wet milling techniques to an average particle diameter of less than ~3 μm and addition of the remaining ingredients, if any.

Formulation Examples 12-16 below illustrate further liquid compositions of the present invention in which many of the formulating ingredients are identified as particular commercially available products. Formulation ingredients used in Examples 12-16 are categorized and further described regarding chemical identity and manufacturer as follows:

| Water-immiscible Liquids | |
|---|---|
| Agnique ® ME 18RD-U | methyl canolate (Cognis) |
| Agnique ® ME 18SD-U | distilled methyl soyate (Cognis) |
| Parol ® 6970 | low-viscosity white mineral oils (Penreco) |
| Stepan ® 108 | glycerol tricaprate/caprylate (Stepan) |
| Surfactants | |

Emulsifying Agents

| | |
|---|---|
| Agnique ® PG 9116 | alkyl polyglycoside, 50% aqueous solution (Cognis) |
| Agnique ® ME 8-3 | ethoxyated methyl caprylate (3 EO) (Cognis) |
| Agnique ® SBO-30 | ethoxylated soybean oil (30 EO) (Cognis) |
| Atlox ® G-1086 | ethoxylated sorbitol hexaoleate (40 EO) (Croda) |
| Cirrosol ® G-1086 | ethoxylated sorbitol hexaoleate (40 EO) (Croda) |
| Toximul ® 8240F | ethoxylated castor oil (40 EO) (Stepan) |
| Tween ® 85 | ethoxylated sorbitan trioleate (20 EO) |
| Proprietary Emulsifier Blends | |
| Agnique ® BL2030 | anionic/nonionic emulsifier blend (Cognis) |
| Toximul ® 3464F | proprietary anionic-nonionic blend (Stepan) |
| Toximul ® 3479F | calcium dodecylbenzene sulfonate/nonionic emulsifier high HLB blend (Stepan) |
| Toximul ® 3476F | calcium dodecylbenzene sulfonate/nonionic emulsifier low HLB blend (Stepan) |
| Wetting and Dispersing Agents | |
| Atlox ® 4912 | poly-12-hydroxystearic acid block copolymer with polyethylene glycol (Croda) |
| Atlox ® 4913 | methyl methacrylate - polyethylene glycol graft copolymer (Croda) |
| Atlox ® 4914 | polyisobutylene succinic anhydride copolymer with polyethylene glycol (Croda) |
| Atlas ® G-5000 | polyethylene oxide-polypropylene oxide block copolymer |
| Synperonic ® A11 | $C_{12}$-$C_{15}$ alcohol ethoxylate (Croda) |
| Break-Thru ® S240 | polyether modified trisiloxane (Evonik Goldschmidt) |
| Break-Thru ® OE441 | polyether-polymethylsiloxane (Evonik Goldschmidt) |
| Suspending Agents | |
| Aerosil ® 200 | amorphous fumed silica (Evonik) |
| Attagel ® 50 | attapulgite clay (BASF) |
| Bentone ® 760 | bis(hydrogenated tallow alkyl) dimethylammonium Bentonite (Elementis Specialities) |
| Rhodopol ® 23 | high-molecular-weight polysaccharide (Rhodia) |
| Tixogel ® EZ 100 | bis(hydrogenated tallow alkyl)dimethyl bentonite (Southern Clay Products) |
| Antifoams, Antifreezes and Biocides | |
| Agnique ® DFM 111S | polydimethylsiloxane emulsion - antifoam (Cognis) |
| propylene glycol | antifreeze |
| Legend ® MK | aqueous solution containing 5-chloro-2-methyl-4-isothiazolin-3-one mixture with 2-methyl-4-isothiazolin-3-one, also containing magnesium nitrate and magnesium chloride - biocide (Rohm and Haas) |
| pH Buffers | |
| acetic acid/sodium acetate | |
| Aqueous Liquid Carrier | |
| water. | |

FORMULATION EXAMPLE 12

| Aqueous Suspension Concentrate | (a) | (b) | (c) |
|---|---|---|---|
| Polymorph Form B of Compound 1 | 20.50% | 18.10% | 14.6% |
| Atlox ® 4912 | 1.50% | — | — |
| Atlox ® 4913 | 3.00% | 2.60% | 2.2% |
| Synperonic ® A11 | — | — | 2.7% |
| Propylene glycol | 10.00% | 10.4% | 8.4% |
| Agnique DFM 111S | 0.40% | 0.40% | 0.4% |
| Legend ® MK | 0.10% | 0.15% | 0.3% |
| Aerosil ® 200 | 0.40% | 1.0% | 2.1% |
| Rhodopol ® 23 | 0.20% | 0.35% | 0.3% |
| Water | 63.90% | 67.0% | 60.0% |

Polymorph Form B is added to the aqueous mixture of the above listed formulation ingredients with high-speed dispersion equipment in operation to break up agglomerated particles and to eliminate rapid settling of the solids in the slurry. If the particle size of the resulting slurry, referred to as the "mill-base", is still too large to feed directly to a media or sand mill, further size reduction and agglomerate break-up is accomplished using a colloid mill. Once the particle size of the mill-base is small enough, the final particle size reduction step is done with a media mill containing glass or ceramic media in a size range of 0.8 to 1.0 mm to effectively reduce the average particle diameter of the polymorph Form B to less than 3 µm.

FORMULATION EXAMPLE 13

| Suspo-emulsion | (a) | (b) | (c) | (d) | (e) |
|---|---|---|---|---|---|
| Polymorph Form B of Compound 1 | 21.00% | 10.00% | 10.50% | 10.50% | 10.50% |
| Agnique ® ME 18SD-U | 21.00% | 33.00% | 16.50% | — | — |
| Stepan ® 108 | — | — | — | 7.50% | 7.50% |
| Parol ® 6970 | — | — | 16.50% | 27.50% | 27.50% |
| Atlas G-5000 | — | — | — | 4.00% | 2.50% |
| Atlox ® 4913 | 1.40% | 1.50% | 1.50% | 2.00% | 2.50% |
| Atlox ® 4912 | — | — | — | 3.00% | 4.00% |
| Synperonic ® A11 | 1.40% | 1.50% | 1.50% | — | — |
| Agnique ® SBO-30 | — | — | 2.50% | — | — |
| Cirrosol ® G-1086 | — | — | 5.30% | — | — |
| Agnique PG 9116 | — | — | 2.50% | — | — |
| Toximul ® 3464F | 5.20% | 8.30% | — | — | — |
| Toximul ® 8240F | 1.40% | 2.10% | — | — | — |
| Propylene glycol | 1.90% | 2.50% | 6.00% | 6.00% | 6.00% |
| Agnique DFM 111S | 1.30% | 0.28% | 0.28% | 0.20% | 0.30% |
| Legend ® MK | 0.10% | 0.10% | 0.10% | 0.10% | 0.10% |
| Aerosil ® 200 | 0.05% | 0.20% | 0.20% | 0.30% | 0.20% |
| Rhodopol ® 23 | — | 0.02% | 0.02% | 0.20% | 0.20% |
| Acetic acid (glacial) | 1.80% | — | — | — | — |
| Sodium acetate trihydrate | 3.00% | — | — | — | — |
| Water | 40.45% | 40.50% | 36.60% | 38.70% | 38.70% |

Polymorph Form B is added to the aqueous mixture of the above listed formulation ingredients except for the water-immiscible liquid component (Agnique ME 18SD-U, Stepan 108, Parol 6970) and emulsifier (Atlas G-5000, Atlox 4913, Atlox 4912, Synperonic A11, Agnique SBO-30, Cirrosol G-1086, Agnique PG 9116, Toximul 3464F, Toximul 8240F) components with high-speed dispersion equipment in operation to break up agglomerated particles and to eliminate rapid settling of the solids in the slurry. The average particle diameter of the polymorph Form B is reduced to less than 3 nm by using the methods described for Formulation Example 11. The water-immiscible liquid component and emulsifier components are then mixed together, and then mixed with the milled slurry using stirring to form the suspo-emulsion compositions.

FORMULATION EXAMPLE 14

| Oil Dispersion | (a) | (b) | (c) | (d) | (e) |
|---|---|---|---|---|---|
| Polymorph Form B of Compound 1 | 15.0% | 10.5% | 10.0% | 10.0% | 10.5% |
| Agnique ® ME 18RD-U | — | — | 55.8% | — | — |
| Agnique ® ME 18SD-U | — | — | — | 40.0% | — |
| Parol ® 6970 | 52.5% | 54.7% | — | — | 54.3% |
| Stepan ® 108 | 14.2% | 15.0% | 15.0% | — | 15.0% |
| Agnique ® BL2030 | — | — | — | 4.0% | — |
| Agnique ® ME 8-3 | — | — | — | 20.0% | — |
| Agnique ® PG 9116 | 4.8% | 5.0% | 5.0% | 5.0% | 5.0% |
| Cirrosol ® G-1086 | 11.5% | 12.0% | 12.0% | 10.0% | 12.0% |
| Tween ® 85 | — | — | — | 10.0% | — |
| Aerosil ® 200 | 1.0% | 1.0% | 1.0% | — | 1.0% |
| Attagel ® 50 | — | — | — | 1.0% | — |
| Bentone ® 760 | — | — | — | — | 1.0% |
| Tixogel ® EZ 100 | — | 0.6% | — | — | — |
| Water | 1.0% | 1.2% | 1.2% | — | 1.2% |

The oil dispersion formulations of Formulation Example 14 are prepared by adding all of the formulating ingredients except for polymorph Form B to the water-immiscible liquid carrier (Agnique ME 14RD-U, Agnique ME 18SD-U, Parol 6970, Stepan 108) with adequate stirring and time to allow uniform mixing and dissolution of all dispersible and/or soluble components. Polymorph Form B is then added, homogenized to allow good contact with the other formulating ingredients, and milled in the same way as described for Formulation Example 13.

FORMULATION EXAMPLE 15

| Suspo-emulsion | (a) | (b) | (c) | (d) | (e) | (f) | (g) |
|---|---|---|---|---|---|---|---|
| Polymorph Form B of Compound 1 | 10.30% | 10.40% | 10.40% | 10.40% | 10.40% | 10.40% | 10.40% |
| Break-Thru ® S240 | — | — | — | — | — | 0.20% | — |
| Agnique ® ME 18 RD-U | — | 15.44% | 15.44% | 14.82% | 14.64% | 14.00% | 14.00% |
| Parol ® 6970 Low Pour | 27.40% | — | — | — | — | — | — |
| Stepan ® 108 | 7.50% | 18.48% | 18.48% | 17.73% | 17.52% | 17.00% | 17.00% |
| Break-Thru ® OE441 | — | 0.98% | 0.98% | 1.07% | 1.07% | 1.00% | 1.00% |
| Atlas ® G-5000 | 2.63% | — | 3.75% | 1.80% | 1.78% | 1.50% | 1.50% |
| Synperonic ® A11 | — | — | — | — | 2.21% | — | — |
| Toximul ® 3479 | — | — | — | — | — | 2.00% | 2.00% |
| Atlox ® 4912 | 4.12% | — | — | — | — | — | — |
| Atlox ® 4914 | — | — | — | 1.73% | — | 2.00% | 2.00% |
| Atlox ® 4913 | 2.25% | 9.00% | 5.25% | 6.90% | 6.83% | 6.35% | 6.55% |
| Rhodopol ® 23 | 0.20% | 0.20% | 0.20% | 0.20% | 0.20% | 0.20% | 0.20% |
| Aerosil ® 200 | 0.25% | 1.04% | 1.04% | 1.00% | 1.00% | 1.00% | 1.00% |
| Propylene glycol | 6.00% | 6.00% | 6.00% | 6.00% | 6.00% | 6.00% | 6.00% |
| Agnique DFM 111S | 0.25% | 0.25% | 0.25% | 0.25% | 0.25% | 0.25% | 0.25% |
| Legend ® MK | 0.10% | 0.10% | 0.10% | 0.10% | 0.10% | 0.10% | 0.10% |
| Water | 39.00% | 38.11% | 38.11% | 38.00% | 38.00% | 38.00% | 38.00% |

Polymorph Form B is added to the aqueous mixture of ingredients comprising the aqueous liquid component of the above formulations (Atlox 4913, Agnique DFM 111S, Legend MK, Aerosil 200, Rhodopol 23, Propylene Glycol and Water) with high-speed dispersion equipment in operation to break up agglomerated particles, aid in the wetting of hydrophobic surfaces and eliminate rapid settling of the solids in the slurry. The average particle diameter of the polymorph Form B is then reduced to less than 3 μm using the methods described for Formulation Example 11. The water-immiscible liquid components and emulsifier components are then blended until homogeneous then mixed with the milled slurry with stirring to form the suspo-emulsion compositions.

FORMULATION EXAMPLE 16

| Oil Dispersion | (a) | (b) | (c) | (d) | (e) | (f) | (g) |
|---|---|---|---|---|---|---|---|
| Polymorph Form B of Compound 1 | 10.30% | 10.30% | 10.30% | 10.30% | 10.40% | 10.40% | 10.40% |
| Break-Thru ® S240 | — | — | — | — | — | — | — |
| Atlox ® 4913 | — | — | — | — | 1.51% | 1.51% | 1.51% |
| Agnique ® ME 18 RD-U | 31.50% | 31.50% | 31.50% | 31.00% | 34.75% | 33.87% | 32.98% |
| Parol ® 6970 Low Pour | 24.30% | — | — | — | — | — | — |
| Stepan ® 108 | 15.40% | 39.70% | 37.70% | 37.00% | 41.48% | 40.42% | 39.36% |
| Break-Thru ® OE441 | — | — | 2.00% | 2.00% | 2.24% | 2.18% | 2.13% |
| Cirrasol ® G 1086 | 12.00% | 12.00% | 12.00% | 7.45% | — | — | — |
| Agnique ® PG 9116 | 5.00% | 5.00% | 5.00% | 7.45% | — | — | — |
| Toximul ® 3476F | — | — | — | — | — | — | — |
| Toximul ® 3479F | — | — | — | — | 8.00% | 8.00% | 12.00% |
| Atlox ® 4914 | — | — | — | 2.00% | — | 2.00% | — |
| Aerosil ® 200 | 0.40% | 0.40% | 0.40% | 1.00% | 1.01% | 1.01% | 1.01% |
| Tixogel ® EZ100 | 0.60% | 0.60% | 0.60% | 0.60% | 0.61% | 0.61% | 0.61% |
| Water | 0.50% | 0.50% | 0.50% | 1.20% | — | — | — |

FORMULATION EXAMPLE 16 (Continued)

| Oil Dispersion | (h) | (i) | (j) | (k) | (l) | (m) |
|---|---|---|---|---|---|---|
| Polymorph Form B of Compound 1 | 10.40% | 10.40% | 10.40% | 10.40% | 10.40% | 10.40% |
| Break-Thru ® S240 | — | — | — | 0.50% | — | 0.50% |
| Atlox ® 4913 | 1.51% | 1.51% | 1.51% | 1.51% | 1.51% | 1.51% |
| Agnique ® ME 18 RD-U | 34.75% | 33.87% | 32.98% | 34.53% | 31.30% | 32.76% |
| Parol ® 6970 Low Pour | — | — | — | — | — | — |
| Stepan ® 108 | 41.48% | 40.42% | 39.36% | 41.21% | 37.36% | 39.10% |
| Break-Thru ® OE441 | 2.24% | 2.18% | 2.13% | 2.23% | 2.02% | 2.11% |
| Cirrasol ® G 1086 | — | — | — | — | 9.79% | — |
| Agnique ® PG 9116 | — | — | — | — | — | — |
| Toximul ® 3476F | 4.00% | 4.00% | — | — | — | — |
| Toximul ® 3479F | 4.00% | 4.00% | 6.00% | 4.00% | — | 6.00% |
| Atlox ® 4914 | — | 2.00% | 6.00% | 4.00% | 6.00% | 6.00% |
| Aerosil ® 200 | 1.01% | 1.01% | 1.01% | 1.01% | 1.01% | 1.01% |
| Tixogel ® EZ100 | 0.61% | 0.61% | 0.61% | 0.61% | 0.61% | 0.61% |
| Water | — | — | — | — | — | — |

The oil dispersion formulations of Formulation Example 16 are prepared by adding all of the formulating ingredients to the water-immiscible liquid carrier (Agnique ME 18 RD-U, Parol 6970, Stepan 108) with adequate stirring and time to allow uniform mixing, dispersion and/or dissolution of all components. Polymorph Form B is then added, homogenized to allow good contact with the other formulating ingredients, then milled in the same or equivalent way as that described in Formulation Example 13.

Although the formulated solid and liquid compositions of the present invention can be applied directly to plants to be protected from disease or to their environment (e.g., their growing medium), for aerial or ground spray application to plant foliage the present compositions are usually first extended (i.e. diluted) in a suitable medium, typically water. Spray volumes of aqueous compositions for direct application to plants or portions thereof (e.g., spray tank compositions) can range from about one to several thousand liters per hectare, but are more typically in the range from about ten to several hundred liters per hectare. Aqueous compositions for spraying typically contain at least about 1 ppm or more (e.g., from 1 ppm to 100 ppm) of Compound 1. The liquid and solid formulations of the present invention can also be metered directly into drip irrigation systems, metered into the furrow during planting, and/or applied to seeds of crops and other desirable vegetation as seed treatments before planting to protect developing roots and other subterranean plant parts and/or foliage through systemic uptake.

For foliar treatment to prevent or cure plant disease, aqueous spray compositions prepared from the liquid compositions (e.g., aqueous suspension concentrates, suspo-emulsions, oil dispersions) comprising a solid form of Compound 1 according to the present invention typically are more efficacious than spray compositions prepared from solid compositions comprising a solid form of Compound 1. Accordingly, a fungicidal liquid composition comprising at least one solid form of Compound 1 is of particular note. The ratio of the volume of the liquid compositions of the present invention to the volume of water used to dilute these compositions is generally in the range from about 1:100 to about 1:1000, more typically from about 1:200 to about 1:800, and most typically from about 1:300 to about 1:600.

To supplement the ingredients contained in pesticide formulations, separately formulated adjuvant products can be added to spray tank mixtures. These additional adjuvants are commonly known as "spray adjuvants" or "tank-mix adjuvants", and include any substance mixed in a spray tank to improve the performance of a pesticide treatment, such as by enhancing efficacy (e.g., biological availability, adhesion, penetration, uniformity of coverage and durability of protection), or minimizing or eliminating spray application problems associated with incompatibility, foaming, drift, evaporation, volatilization and degradation. As no single adjuvant generally can provide all these benefits, compatible adjuvants are often combined to perform multiple functions. To obtain optimal performance, adjuvants are selected with regard to the properties of the active ingredient, formulation and target (e.g., the crop being sprayed and the properties of the active ingredient and composition being applied to the crop).

Among the spray adjuvants, oils including crop oils, crop oil concentrates, vegetable oil concentrates and methylated seed oil concentrates are used to improve their efficacy, possibly by means of promoting more even and uniform spray deposits. Products identified as "crop oil" typically contain 95 to 98% paraffin or naphtha-based petroleum oil and 1 to 2% of one or more surfactants functioning as emulsifiers. Products identified as "crop oil concentrates" typically consist of 80 to 85% of emulsifiable petroleum-based oil and 15 to 20% of non-ionic surfactants. Products identified as "vegetable oil concentrates" typically consist of 80 to 85% of vegetable oil (i.e. seed or fruit oil, most commonly from cotton, linseed, soybean or sunflower) and 15 to 20% of non-ionic surfactants. Adjuvant performance can be improved by replacing the vegetable oil with methyl esters of fatty acids that are typically derived from vegetable oils. Examples of methylated seed oil concentrates include MSO® Concentrate from UAP-Loveland Products, Inc. and Premium MSO Methylated Spray Oil from Helena Chemical Company. The amount of oil-based adjuvants added to spray mixtures generally does not exceed about 2.5% by volume, and more typically the amount is from about 0.1 to about 1% by volume. The application rates of oil-based adjuvants added to spray mixtures are typically between about 1 to about 5 L per hectare, and methylated seed oil-based adjuvants in particular are typically used at a rate from about 1 to about 2.5 L per hectare.

Spray adjuvants containing mixtures of emulsifiers with oils, particularly mineral oils, methylated seed oils and triglycerides, are compatible in tank mixtures with the liquid compositions of the present invention, e.g., aqueous suspension concentrates, suspo-emulsions and oil dispersions. Therefore one embodiment of the present invention relates to a method for controlling plant diseases caused by fungal pathogens diluting a liquid composition of the present invention with water, adding an adjuvant such as a mineral oil or methylated seed oil (in any order of addition or mixing) to form a diluted composition, and applying to the plant of portion thereof, or to the plant seed foliage, a fungicidally effective amount of the diluted composition.

The solid forms of Compound 1 are useful for controlling plant disease, particularly disease caused by Oomycete fungal plant pathogens. Not only can application of a solid form of Compound 1 to a plant, plant part, seed or growing medium prevent plant disease, but such application can cure or eradicate the spread of existing disease. Also, because of phloem mobility of Compound 1, application of a solid form to a seed or plant part can protect adjacent plant parts, including new foliage growth. Furthermore, a solid form of Compound 1 can be combined with one or more other active ingredients in fungicidal compositions of the present invention to provide a broader spectrum of plant disease control. The present invention therefore further comprises a method for controlling plant diseases caused by fungal plant pathogens comprising applying to the plant or portion thereof to be protected, or to the plant seed to be protected, an effective amount of a solid form of Compound 1 or a fungicidal composition comprising the solid form of Compound 1. The solid forms of Compound 1 and/or compositions of this invention provide control of diseases caused by a broad spectrum of fungal plant pathogens in the Basidiomycete, Ascomycete, Oomycete and Deuteromycete classes. They are effective in controlling a broad spectrum of plant diseases, particularly foliar pathogens of ornamental, turf, vegetable, field, cereal, and fruit crops. These pathogens include: Oomycetes, including *Phytophthora* diseases such as *Phytophthora infestans, Phytophthora megasperma, Phytophthora parasitica, Phytophthora cinnamomi* and *Phytophthora capsici, Pythium* diseases such as *Pythium aphanidermatum*, and diseases in the Peronosporaceae family such as *Plasmopara viticola, Peronospora* spp. (including *Peronospora tabacina* and *Peronospora parasitica*), *Pseudoperonospora* spp. (including *Pseudoperonospora cubensis*) and *Bremia lactucae*; Ascomycetes, including *Alternaria* diseases such as *Alternaria solani* and *Alternaria brassicae, Guignardia* diseases such as *Guignardia bidwell, Venturia* diseases such as *Venturia inaequalis,*

*Septoria* diseases such as *Septoria nodorum* and *Septoria tritici*, powdery mildew diseases such as *Erysiphe* spp. (including *Erysiphe graminis* and *Erysiphe polygoni*), *Uncinula necatur*, *Sphaerotheca fuligena* and *Podosphaera leucotricha*, *Pseudocercosporella herpotrichoides*, *Botrytis* diseases such as *Botrytis cinerea, Monilinia fructicola*, *Sclerotinia* diseases such as *Scerotinia sclerotorum, Magnaporthe grisea, Phomopsis viticola, Helminthosporium* diseases such as *Helminthosporium tritici repentis, Pyrenophora teres*, anthracnose diseases such as *Glomerella* or *Coletotrichum* spp. (such as *Coletotrichum graminicola* and *Coletotrichum orbiculare*), and *Gaeumnnanomnyces graminis*; Basidiomycetes, including rust diseases caused by *Puccinia* spp. (such as *Puccinia recondita, Puccinia striformis, Puccinia hordei, Puccinia graminis* and *Puccinia arachidis*), *Hemileia vastatrix* and *Phakopsora pachyrhizi*; other pathogens including *Rulstroemia floccosum* (also known as *Sclerontina homoeocarpa*); *Rhizoctonia* spp. (such as *Rhizoctonia solani*); *Fusarium* diseases such as *Fusarium roseum, Fusarium graminearum* and *Fusarium oxysporum; Verticillium dahliae; Sclerotium rolfsil; Rynchosporium secalis; Cercosporidium personatum, Cercospora arachidicola* and *Cercospora beticola*; and other genera and species closely related to these pathogens. In addition to their fungicidal activity, the compositions or combinations also have activity against bacteria such as *Erwinia amylovora, Xanthomonas campestris, Pseudomonas syringae*, and other related species.

The solid forms of Compound 1 and/or compositions of this invention provide control of diseases caused by a broad spectrum of fungal plant pathogens in the Basidiomycete, Ascomycete, Oomycete and Deuteromycete classes. They are effective in controlling a broad spectrum of plant diseases, foliar pathogens of crops including: cereal grain crops such as wheat, barley, oats, rye, triticale, rice, maize, sorghum and millet; vine crops such as table and wine grapes; field crops such as oilseed rape (canola), sunflower; sugar beets, sugar cane, soybean, peanuts (groundnut), tobacco, alfafa, clover, lespedeza, trefoil and vetch; pome fruits such as apple, pear, crabapple, loquat, mayhaw and quince; stone fruits such as peaches, cherries, plums, apricots, nectarines and almonds; citrus fruits such as lemons, limes, oranges, grapefruit, mandarin (tangerines) and kumquat; root and tuber vegetables and field crops (and their foliage) such as artichoke, garden and sugar beet, carrot, cassava, ginger, ginseng, horseradish, parsnip, potato, radish, rutabaga, sweet potato, turnip and yam; bulb vegetables such as garlic, leek, onion and shallot; leafy vegetables such as arugula (roquette), celery, celery, cress, endive (escarole), fennel, head and leaf lettuce, parsley, radicchio (red chicory), rhubarb, spinach and Swiss chard; *brassica* (cole) leafy vegetables such as broccoli, broccoli raab (rapini), Brussels sprouts, cabbage, bok choy, cauliflower, collards, kale, kohlrabi, mustard and greens; legume vegetables (succulent or dried) such as lupin, bean (*Phaseolus* spp.) (including field bean, kidney bean, lima bean, navy bean, pinto bean, runner bean, snap bean, tepary bean and wax bean), bean (*Vigna* spp.) (including adzuki bean, asparagus bean, blackeyed pea, catjang, Chinese longbean, cowpea, crowder pea, moth bean, mung bean, rice bean, southern pea, urd bean and yardlong bean), broad bean (fava), chickpea (garbanzo), guar, jackbean, lablab bean, lentil and pea (*Pisum* spp.) (including dwarf pea, edible-podded pea, English pea, field pea, garden pea, green pea, snowpea, sugar snap pea, pigeon pea and soybean); fruiting vegetables such as eggplant, groundcherry (*Physalis* spp.), pepino and pepper (including bell pepper, chili pepper, cooking pepper, pimento, sweet pepper; tomatillo and tomato); cucurbit vegetables such as Chayote (fruit), Chinese waxgourd (Chinese preserving melon), citron melon, cucumber, gherkin, edible gourd (including hyotan, cucuzza, hechima, and Chinese okra), *Momordica* spp. (including balsam apple, balsam pear, bittermelon and Chinese cucumber), muskmelon (including cantaloupe and pumpkin), summer and winter squash (including butternut squash, calabaza, hubbard squash, acorn squash, spaghetti squash) and watermelon; berries such as blackberry (including bingleberry, boysenberry, dewberry, lowberry, marionberry, olallieberry and youngberry), blueberry, cranberry, currant, elderberry, gooseberry, huckleberry, loganberry, raspberry and strawberry; tree nuts such as almond, beech nut, Brazil nut, butternut, cashew, chestnut, chinquapin, filbert (hazelnut), hickory nut, macadamia nut, pecan and walnut; tropical fruits and other crops such as bananas, plantains, mangos, coconuts, papaya, guava, avocado, lichee, agave, coffee, cacao, sugar cane, oil palm, sesame, rubber and spices; fiber crops such as cotton, flax and hemp; turfgrasses (including warm- and cool-season turfgrasses) such as bentgrass, Kentucky bluegrass, St. Augustine grass, tall fescue and Bermuda grass.

Plant disease control is ordinarily accomplished by applying an effective amount of a solid form of Compound 1 either pre- or post-infection, to the portion of the plant to be protected such as the roots, stems, foliage, fruit, seeds, tubers or bulbs, or to the media (soil or sand) in which the plants to be protected are growing. The solid form of Compound 1 can also be applied to seeds to protect the seeds and seedlings developing from the seeds. A formulation of a solid form of Compound 1 can also be applied through irrigation water to treat plants.

The optimal application rate of a solid form of Compound 1 for plant disease control is affected by a variety of factors such as the fungal pathogens to be controlled, the susceptibility of the fungal pathogens to Compound 1 and any other active ingredients present in the composition, the nature and concentration of any adjuvants, growth stage of the plants being protected, and environmental conditions at time of application and expected during the growing season, and can be determined by simple experimentation under actual use conditions. Foliage can normally be protected when treated at a rate of from less than about 1 g/ha to about 1000 g/ha of a solid form of Compound 1. Foliar application rates of a solid form of Compound 1 are typically at least about 2 g/ha, more typically at least about 5 g/ha, and most typically at least about 10 g/ha, and typically no more than about 400 g/ha, more typically no more than about 200 g/ha and most typically no more than about 100 g/ha. Seed and seedlings can normally be protected when seed is treated at a rate of from about 0.1 to about 10 g per kilogram of seed.

The solid forms of Compound 1 can also be mixed with one or more other biologically active compounds or agents including fungicides, insecticides, nematocides, bactericides, acaricides, herbicides, herbicide safeners, growth regulators such as insect molting inhibitors and rooting stimulants, chemosterilants, semiochemicals, repellents, attractants, pheromones, feeding stimulants, plant nutrients, other biologically active compounds or entomopathogenic bacteria, virus or fungi to form a multi-component pesticide giving an even broader spectrum of agricultural protection. Thus the present invention also pertains to a composition comprising a fungicidally effective amount of at least one solid form of Compound 1 and a biologically effective amount of at least one additional biologically active compound or agent and can further comprise at least one of a surfactant, a solid diluent or a liquid diluent. To provide mixtures of the present invention, one or more other biologically active compounds or agents can be formulated together with a solid form of Compound 1 to form a premix, or one or more other biologically active compounds or agents can be formulated separately from Compound 1, and the formulations combined together before application (e.g., in a spray tank) or, alternatively, applied in succession.

Of note is a composition which in addition to a solid form of Compound 1 includes at least one fungicidal compound selected from the group consisting of the classes (1) methyl benzimidazole carbamate (MBC) fungicides; (2) dicarboximide fungicides; (3) demethylation inhibitor (DM) fungicides; (4) phenylamide fungicides; (5) amine/morpholine fungicides; (6) phospholipid biosynthesis inhibitor fungicides; (7) carboxamide fungicides; (8) hydroxy(2-amino-)pyrimidine fungicides; (9) anilinopyrimidine fungicides; (10) N-phenyl carbamrnate funmgicides; (11) quinone outside inhibitor (QoI) fungicides; (12) phenylpyrrole fungicides; (13) quinoline fungicides; (14) lipid peroxidation inhibitor fungicides; (15) melanin biosynthesis inhibitors-reductase (MBI-R) fungicides; (16) melanin biosynthesis inhibitors-dehydratase (MBI-D) fungicides; (17) hydroxyanilide fungicides; (18) squalene-epoxidase inhibitor fungicides; (19) polyoxin fungicides; (20) phenylurea fungicides; (21) quinone inside inhibitor (QiI) fungicides; (22) benzamide fungicides; (23) enopyranuronic acid antibiotic fungicides; (24) hexopyranosyl antibiotic fungicides; (25) glucopyranosyl antibiotic: protein synthesis fungicides; (26) glucopyranosyl antibiotic: trehalase and inositol biosynthesis fungicides; (27) cyanoacetamideoxime fungicides; (28) carbamate fungicides; (29) oxidative phosphorylation uncoupling fungicides; (30) organo tin fungicides; (31) carboxylic acid fungicides; (32) heteroaromatic fungicides; (33) phosphonate fungicides; (34) phthalamic acid fungicides; (35) benzotriazine fungicides; (36) benzene-sulfonamide fungicides; (37) pyridazinone fungicides; (38) thiophene-carboxamide fungicides; (39) pyrimidinamide fungicides; (40) carboxylic acid amide (CAA) fungicides; (41) tetracycline antibiotic fungicides; (42) thiocarbamate fungicides; (43) benzamide fungicides; (44) host plant defense induction fungicides; (45) multi-site contact activity fungicides; (46) fungicides other than classes (1) through (45); and salts of compounds of classes (1) through (46).

Further descriptions of these classes of fungicidal compounds are provided below.

(1) "Methyl benzimidazole carbamate (MBC) fungicides" (Fungicide Resistance Action Committee (FRAC) code 1) inhibit mitosis by binding to β-tubulin during microtubule assembly. Inhibition of microtubule assembly can disrupt cell division, transport within the cell and cell structure. Methyl benzimidazole carbamate fungicides include benzimidazole and thiophanate fungicides. The benzimidazoles include benomyl, carbendazim, fuberidazole and thiabendazole. The thiophanates include thiophanate and thiophanate-methyl.

(2) "Dicarboximide fungicides" (Fungicide Resistance Action Committee (FRAC) code 2) are proposed to inhibit a lipid peroxidation in fungi through interference with NADH cytochrome c reductase. Examples include chlozolinate, iprodione, procymidone and vinclozolin.

(3) "Demethylation inhibitor (DMI) fungicides" (Fungicide Resistance Action Committee (FRAC) code 3) inhibit C14-demethylase, which plays a role in sterol production. Sterols, such as ergosterol, are needed for membrane structure and function, making them essential for the development of functional cell walls. Therefore, exposure to these fungicides results in abnormal growth and eventually death of sensitive fungi. DMI fungicides are divided between several chemical classes: azoles (including triazoles and imidazoles), pyrimidines, piperazines and pyridines. The triazoles include azaconazole, bitertanol, bronmuconazole, cyproconazole, difenoconazole, diniconazole (including diniconazole-M), epoxiconazole, fenbuconazole, fluquinconazole, flusilazole, flutriafol, hexaconazole, imibenconazole, ipconazole, metconazole, myclobutanil, penconazole, propiconazole, prothioconazole, simeconazole, tebuconazole, tetraconazole, triadimefon, triadimenol, triticonazole and uniconazole. The imidazoles include clotrimazole, imazalil, oxpoconazole, prochloraz, pefurazoate and triflumizole. The pyrimidines include fenarimol and nuarimol. The piperazines include triforine. The pyridines include pyrifenox. Biochemical investigations have shown that all of the above mentioned fungicides are DMI fungicides as described by K. H. Kuck et al. in *Modern Selective Fungicides—Properties, Applications and Mechanisms of Action*, H. Lyr (Ed.), Gustav Fischer Verlag: New York, 1995, 205-258.

(4) "Phenylamide fungicides" (Fungicide Resistance Action Committee (FRAC) code 4) are specific inhibitors of RNA polymerase in Oomycete fungi. Sensitive fungi exposed to these fungicides show a reduced capacity to incorporate uridine into rRNA, Growth and development in sensitive fungi is prevented by exposure to this class of fungicide. Phenylamide fungicides include acylalanine, oxazolidinone and butyrolactone fungicides. The acylalanines include benalaxyl, benalaxyl-M, furalaxyl, metalaxyl and metalaxyl-M/mefenoxam. The oxazolidinones include oxadixyl. The butyrolactones include ofurace.

(5) "Amine/morpholine fungicides" (Fungicide Resistance Action Committee (FRAC) code 5) inhibit two target sites within the sterol biosynthetic pathway, $\Delta^8 \rightarrow \Delta^7$ isomerase and $\Delta^{14}$ reductase. Sterols, such as ergosterol, are needed for membrane structure and function, making them essential for the development of functional cell walls. Therefore, exposure to these fungicides results in abnormal growth and eventually death of sensitive fungi. Amine/morpholine fungicides (also known as non-DMI sterol biosynthesis inhibitors) include morpholine, piperidine and spiroketal-amine fungicides. The morpholines include aldimorph, dodemorph, fenpropimorph, tridemorph and trimorphamide. The piperidines include fenpropidin and piperalin. The spiroketal-amines include spiroxamine.

(6) "Phospholipid biosynthesis inhibitor fungicides" (Fungicide Resistance Action Committee (FRAC) code 6) inhibit growth of fungi by affecting phospholipid biosynthesis. Phospholipid biosynthesis fungicides include phosphorothiolate and dithiolane fungicides. The phosphorothiolates include edifenphos, iprobenfos and pyrazophos. The dithiolanes include isoprothiolane.

(7) "Carboxamide fungicides" (Fungicide Resistance Action Committee (FRAC) code 7) inhibit Complex II (succinate dehydrogenase) fungal respiration by disrupting a key enzyme in the Krebs Cycle (TCA cycle) named succinate dehydrogenase. Inhibiting respiration prevents the fungus from making ATP, and thus inhibits growth and reproduction. Carboxamide fungicides include benzamides, furan carboxamides, oxathiin carboxamides, thiazole carboxamides, pyrazole carboxamides and pyridine carboxamides. The benzamides include benodanil, flutolanil and mepronil. The furan carboxamides include fenfuram. The oxathiin carboxamides include carboxin and oxycarboxin. The thiazole carboxamides include thifluzamide. The pyrazole carboxamides include furametpyr, penthiopyrad, bixafen, N-[2-(1S,2R)-[1,1'-bicyclopropyl]-2-ylphenyl]-3-(difluoromethyl)-1-methyl-1-pyrazole-4-carboxamide and N-[2-(1,3-dimethylbutyl)phenyl]-5-fluoro-1,3-dimethyl-1H-pyrazole-4-carboxamide. The pyridine carboxamides include boscalid.

(8) "Hydroxy(2-amino-)pyrimidine fungicides" (Fungicide Resistance Action Committee (FRAC) code 8) inhibit nucleic acid synthesis by interfering with adenosine deaminase. Examples include bupirimate, dimethirimol and ethirimol.

(9) "Anilinopyrimidine fungicides" (Fungicide Resistance Action Committee (FRAC) code 9) are proposed to inhibit biosynthesis of the amino acid methionine and to disrupt the secretion of hydrolytic enzymes that lyse plant cells during infection. Examples include cyprodinil, mepanipyrim and pyrimethanil.

(10) "N-Phenyl carbamate fungicides" (Fungicide Resistance Action Committee (FRAC) code 10) inhibit mitosis by binding to β-tubulin and disrupting microtubule assembly. Inhibition of microtubule assembly can disrupt cell division, transport within the cell and cell structure. Examples include diethofencarb.

(11) "Quinone outside inhibitor (QoI) fungicides" (Fungicide Resistance Action Committee (FRAC) code 11) inhibit Complex III mitochondrial respiration in fungi by affecting ubiquinol oxidase. Oxidation of ubiquinol is blocked at the "quinone outside" ($Q_o$) site of the cytochrome $bc_1$ complex, which is located in the inner mitochondrial membrane of fungi. Inhibiting mitochondrial respiration prevents normal fungal growth and development. Quinone outside inhibitor fungicides (also known as strobilurin fungicides) include methoxyacrylate, methoxycarbamate, oximinoacetate, oximinoacetamide, oxazolidinedione, dihydrodioxazine, imidazolinone and benzylcarbamate fungicides. The methoxyacrylates include azoxystrobin, enestroburin (SYP-Z071) and picoxystrobin. The methoxycarbamates include pyraclostrobin. The oximinoacetates include kresoxim-methyl and trifloxystrobin. The oximinoacetamides include dimoxystrobin, metominostrobin, orysastrobin, α-[methoxyimino]-N-methyl-2-[[[1-[3-(trifluoromethyl)phenyl]ethoxy]imino]-methyl]benzeneacetamide and 2-[[[3-(2,6-dichlorophenyl)-1-methyl-2-propen-1-ylidene]-amino]oxy]methyl]-α-(methoxyimino)-N-methylbenzeneacetamide.
The oxazolidinediones include famoxadone. The dihydrodioxazines include fluoxastrobin. The imidazolinones include fenamidone. The benzylcarbamates include pyribencarb.

(12) "Phenylpyrrole fungicides" (Fungicide Resistance Action Committee (FRAC) code 12) inhibit a MAP protein kinase associated with osmotic signal transduction in fungi. Fenpiclonil and fludioxonil are examples of this fungicide class.

(13) "Quinoline fungicides" (Fungicide Resistance Action Committee (FRAC) code 13) are proposed to inhibit signal transduction by affecting G-proteins in early cell signaling. They have been shown to interfere with germination and/or appressorium formation in fungi that cause powder mildew diseases. Quinoxyfen is an example of this class of fungicide.

(14) "Lipid peroxidation inhibitor fungicides" (Fungicide Resistance Action Committee (FRAC) code 14) are proposed to inhibit lipid peroxidation which affects membrane synthesis in fungi. Members of this class, such as etridiazole, may also affect other biological processes such as respiration and melanin biosynthesis. Lipid peroxidation fungicides include aromatic carbon and 1,2,4-thiadiazole fungicides. The aromatic carbon fungicides include biphenyl, chloroneb, dicloran, quintozene, tecnazene and tolclofos-methyl. The 1,2,4-thiadiazole fungicides include etridiazole.

(15) "Melanin biosynthesis inhibitors-reductase (MBI-R) fungicides" (Fungicide Resistance Action Committee (FRAC) code 16.1) inhibit the naphthal reduction step in melanin biosynthesis. Melanin is required for host plant infection by some fungi. Melanin biosynthesis inhibitors-reductase fungicides include isobenzofuranone, pyrroloquinolinone and triazolobenzothiazole fungicides. The isobenzofuranones include fthalide. The pyrroloquinnliones include pyroquilon. The triazolobenzothiazoles include tricyclazole.

(16) "Melanin biosynthesis inhibitors-dehydratase (MBI-D) fungicides" (Fungicide Resistance Action Committee (FRAC) code 16.2) inhibit scytalone dehydratase in melanin biosynthesis. Melanin in required for host plant infection by some fungi. Melanin biosynthesis inhibitors-dehydratase fungicides include cyclopropanecarboxamide, carboxamide and propionamide fungicides. The cyclopropanecarboxamides include carpropamid. The carboxamides include diclocymet. The propionamides include fenoxanil.

(17) "Hydroxyanilide fungicides (Fungicide Resistance Action Committee (FRAC) code 17) inhibit C4-demethylase which plays a role in sterol production. Examples include fenhexamid.

(18) "Squalene-epoxidase inhibitor fungicides" (Fungicide Resistance Action Committee (FRAC) code 18) inhibit squalene-epoxidase in ergosterol biosynthesis pathway. Sterols such as ergosterol are needed for membrane structure and function, making them essential for the development of functional cell walls. Therefore exposure to these fungicides results in abnormal growth and eventually death of sensitive fungi. Squalene-epoxidase inhibitor fungicides include thiocarbamate and allylamine fungicides. The thiocarbamates include pyributicarb. The allylamines include naftifine and terbinafine.

(19) "Polyoxin fungicides" (Fungicide Resistance Action Committee (FRAC) code 19) inhibit chitin synthase. Examples include polyoxin.

(20) "Phenylurea fungicides" (Fungicide Resistance Action Committee (FRAC) code 20) are proposed to affect cell division. Examples include pencycuron.

(21) "Quinone inside inhibitor (QiI) fungicides" (Fungicide Resistance Action Committee (FRAC) code 21) inhibit Complex III mitochondrial respiration in fungi by affecting ubiquinol reductase. Reduction of ubiquinol is blocked at the "quinone inside"($Q_i$) site of the cytochrome $bc_1$ complex, which is located in the inner mitochondrial membrane of fungi. Inhibiting mitochondrial respiration prevents normal fungal growth and development. Quinone inside inhibitor fungicides include cyanoimidazole and sulfamoyltriazole fungicides. The cyanoimidazoles include cyazofamid. The sulfamoyltriazoles include amisulbrom.

(22) "Benzamide fungicides" (Fungicide Resistance Action Committee (FRAC) code 22) inhibit mitosis by binding to β-tubulin and disrupting microtubule assembly. Inhibition of microtubule assembly can disrupt cell division, transport within the cell and cell structure. Examples include zoxamide.

(23) "Enopyranuronic acid antibiotic fungicides" (Fungicide Resistance Action Committee (FRAC) code 23) inhibit growth of fungi by affecting protein biosynthesis. Examples include blasticidin-S.

(24) "Hexopyranosyl antibiotic fungicides" (Fungicide Resistance Action Committee (FRAC) code 24) inhibit growth of fungi by affecting protein biosynthesis. Examples include kasugamycin.

(25) "Glucopyranosyl antibiotic: protein synthesis fungicides" (Fungicide Resistance Action Committee (FRAC) code 25) inhibit growth of fungi by affecting protein biosynthesis. Examples include streptomycin.

(26) "Glucopyranosyl antibiotic: trehalase and inositol biosynthesis fungicides"(Fungicide Resistance Action Committee (FRAC) code 26) inhibit trehalase in inositol biosynthesis pathway. Examples include validamycin.

(27) "Cyanoacetamideoxime fungicides (Fungicide Resistance Action Committee (FRAC) code 27) include cymoxanil.

(28) "Carbamate fungicides" (Fungicide Resistance Action Committee (FRAC) code 28) are considered multi-site inhibitors of fungal growth. They are proposed to interfere with the synthesis of fatty acids in cell membranes, which then disrupts cell membrane permeability. Propamacarb, propamacarb-hydrochloride, iodocarb, and prothiocarb are examples of this fungicide class.

(29) "Oxidative phosphorylation uncoupling fungicides" (Fungicide Resistance Action Committee (FRAC) code 29) inhibit fungal respiration by uncoupling oxidative phosphorylation. Inhibiting respiration prevents normal fungal growth and development. This class includes 2,6-dinitroanilines such as fluazinam, pyrimidonehydrazones such as ferimzone and dinitrophenyl crotonates such as dinocap, meptyldinocap and binapacryl.

(30) "Organo tin fungicides" (Fungicide Resistance Action Committee (FRAC) code 30) inhibit adenosine triphosphate (ATP) synthase in oxidative phosphorylation pathway. Examples include fentin acetate, fentin chloride and fentin hydroxide.

(31) "Carboxylic acid fungicides" (Fungicide Resistance Action Committee (FRAC) code 31) inhibit growth of fungi by affecting deoxyribonucleic acid (DNA) topoisomerase type II (gyrase). Examples include oxolinic acid.

(32) "Heteroaromatic fungicides" (Fungicide Resistance Action Committee (FRAC) code 32) are proposed to affect DNA/ribonucleic acid (RNA) synthesis. Heteroaromatic fungicides include isoxazole and isothiazolone fungicides. The isoxazoles include hymexazole and the isothiazolones include octhilinone.

(33) "Phosphonate fungicides" (Fungicide Resistance Action Committee (FRAC) code 33) include phosphorous acid and its various salts, including fosetyl-aluminum.

(34) "Phthalamic acid fungicides" (Fungicide Resistance Action Committee (FRAC) code 34) include teclofthalam.

(35) "Benzotriazine fungicides" (Fungicide Resistance Action Committee (FRAC) code 35) include triazoxide.

(36) "Benzene-sulfonamide fungicides" (Fungicide Resistance Action Committee (FRAC) code 36) include flusulfamide.

(37) "Pyridazinone fungicides" (Fungicide Resistance Action Committee (FRAC) code 37) include diclomezine.

(38) "Thiophene-carboxamide fungicides" (Fungicide Resistance Action Committee (FRAC) code 38) are proposed to affect ATP production. Examples include silthiofam.

(39) "Pyrimidinamide fungicides" (Fungicide Resistance Action Committee (FRAC) code 39) inhibit growth of fungi by affecting phospholipid biosynthesis and include diflumetorim.

(40) "Carboxylic acid amide (CAA) fungicides" (Fungicide Resistance Action Committee (FRAC) code 40) are proposed to inhibit phospholipid biosynthesis and cell wall deposition. Inhibition of these processes prevents growth and leads to death of the target fungus. Carboxylic acid amide fungicides include cinnamic acid amide, valinamide carbamate and mandelic acid amide fungicides. The cinnamic acid amides include dimethomorph and flumorph. The valinamide carbamates include benthiavalicarb, benthiavalicarb-isopropyl, iprovalicarb and valiphenal. The mandelic acid amides include mandipropamid, N-[2-[4-[[3-(4-chlorophenyl)-2-propyn-1-yl]oxy]-3-methoxyphenyl]ethyl]-3-methyl-2-[(methylsulfonyl)amino]butanamide and N-[2-[4-[[3-(4-chlorophenyl)-2-propyn-1-yl]oxy]-3-methoxyphenyl]ethyl]-3-methyl-2-[(ethylsulfonyl)amino]butanamide.

(41) "Tetracycline antibiotic fungicides" (Fungicide Resistance Action Committee (FRAC) code 41) inhibit growth of fungi by affecting complex 1 nicotinamide adenine dinucleotide (NADH) oxidoreductase. Examples include oxytetracycline.

(42) "Thiocarbamate fungicides (b42)" (Fungicide Resistance Action Committee (FRAC) code 42) include methasulfocarb.

(43) "Benzamide fungicides" (Fungicide Resistance Action Committee (FRAC) code 43) inhibit growth of fungi by delocalization of spectrin-like proteins. Examples include acylpicolide fungicides such as fluopicolide and fluopyram.

(44) "Host plant defense induction fungicides" (Fungicide Resistance Action Committee (FRAC) code P) induce host plant defense mechanisms. H-lost plant defense induction fungicides include benzo-thiadiazole, benzisothiazole and thiadiazole-carboxamide fungicides. The benzo-thiadiazoles include acibenzolar-S-methyl. The benzisothiazoles include probenazole. The thiadiazole-carboxamides include tiadinil and isotianil.

(45) "Multi-site contact fungicides" inhibit fungal growth through multiple sites of action and have contact/preventive activity. This class of fungicides includes: (45.1) "copper fungicides" (Fungicide Resistance Action Committee (FRAC) code M1)", (45.2) "sulfur fungicides" (Fungicide Resistance Action Committee (FRAC) code M2), (45.3) "dithiocarbamate fungicides" (Fungicide Resistance Action Committee (FRAC) code M3), (45.4) "phthalimide fungicides" (Fungicide Resistance Action Committee (FRAC) code M4), (45.5) "chloronitrile fungicides" (Fungicide Resistance Action Committee (FRAC) code M5), (45.6) "sulfamide fungicides" (Fungicide Resistance Action Committee (FRAC) code M6), (45.7) "guanidine fungicides" (Fungicide Resistance Action Committee (FRAC) code M7), (45.8) "triazine fungicides" (Fungicide Resistance Action Committee (FRAC) code M8) and (45.9) "quinone fungicides" (Fungicide Resistance Action Committee (FRAC) code M9). "Copper fungicides" are inorganic compounds containing copper, typically in the copper(II) oxidation state; examples include copper oxychloride, copper sulfate and copper hydroxide, including compositions such as Bordeaux mixture (tribasic copper sulfate). "Sulfur fungicides" are inorganic chemicals containing rings or chains of sulfur atoms; examples include elemental sulfur. "Dithiocarbamate fungicides" contain a dithiocarbamate molecular moiety; examples include mancozeb, metiram, propineb, ferbam, maneb, thiram, zineb and ziram. "Phthalimide fungicides" contain a phthalimide molecular moiety; examples include folpet, captan and captafol. "Chloronitrile fungicides" contain an aromatic ring substituted with chloro and cyano; examples include chlorothalonil. "Sulfamide fungicides" include dichlofluanid and tolyfluanid. "Guanidine fungicides" include dodine, guazatine, iminoctadine albesilate and iminoctadine triacetate. "Triazine fungicides" include anilazine. "Quinone fungicides" include dithianon.

(46) "Fungicides other than fungicides of classes (1) through (45)" include certain fungicides whose mode of action may be unknown. These include: (46.1) "thiazole carboxamide fungicides" (Fungicide Resistance Action Committee (FRAC) code U5), (46.2) "phenyl-acetamide fungicides" (Fungicide Resistance Action Committee (FRAC) code U6), (46.3) "quinazolinone fungicides" (Fungicide Resistance Action Committee (FRAC) code U7) and (46.4) "benzophenone fungicides" (Fungicide Resistance Action Committee (FAC) code U8). The thiazole carboxamides include ethaboxam. The phenyl-acetamides include cyflufenamid and N-[[(cyclopropylmethoxy)amino][6-(difluoromethoxy)-2,3-difluorophenyl]-methylene]benzeneacetamide. The quinazolinones include proquinazid and 2-butoxy-6-iodo-3-propyl-4H-1-benzopyran-4-one. The benzophenones include metrafenone. The (b46) class also includes bethoxazin, neo-asozin (ferric methanearsonate), pyrrolnitrin, quinomethionate, N-[2-[4-[[3-(4-chlorophenyl)-2-propyn-1-yl]oxy]-3-methoxy-phenyl]ethyl]-3-methyl-2-[(methylsulfonyl)amino]butanamide, N-[2-[4-[[3-(4-chloro-phenyl)-2-propyn-1-yl]oxy]-3-methoxyphenyl]ethyl]-3-methyl-2-[(ethylsulfonyl)amino]-butanamide, 2-[[2-fluoro-5-(tri fluoromethyl)phenyl]thio]-2-[3-(2-methoxyphenyl)-2-thiazolidinylidene]acetonitrile, 3-[5-(4-chlorophenyl)-2,3-dimethyl-3-isoxazolidinyl]pyridine, 4-fluorophenyl N-[1-[[[1-(4-cyanophenyl)ethyl]sulfonyl]methyl]propyl]carbamate, 5-chloro-6-(2,4,6-trifluorophenyl)-7-(4-methylpiperidin-1-yl)[1,2,4]triazolo[1,5-a]pyrimidine, N-(4-chloro-2-nitrophenyl)-N-ethyl-4-methylbenzenesulfonamide, N-[[(cyclopropylmethoxy)-amino][6-(difluoromethoxy)-2,3-difluorophenyl]methylene]benzeneacetamide, N'-[4-[4-chloro-3-(trifluoromethyl)phenoxy]-2,5-dimethylphenyl]-N-ethyl-N-methylmethanimidamide and 1-[(2-propenylthio)carbonyl]-2-(1-methylethyl)-4-(2-methylphenyl)-5-amino-1-pyrazol-3-one.

Of note is a mixture (i.e. composition) comprising at least one solid form of Compound 1 (e.g., polymorph Form B) and at least one fungicidal compound selected from the group consisting of the aforedescribed classes (1) through (46). Also of note is a composition comprising said mixture (in fungicidally effective amount) and further comprising at least one additional component selected from the group consisting of surfactants, solid diluents and liquid diluents. Of particular note is a mixture (i.e. composition) comprising at least one solid form of Compound 1 and at least one fungicidal compound selected from the group of specific compounds listed above in connection with classes (1) through (46). Also of particular note is a composition comprising said mixture (in fungicidally effective amount) and further comprising at least one additional surfactant selected from the group consisting of surfactants, solid diluents and liquid diluents.

In certain instances, combinations of a solid form of Compound 1 (e.g. polymorph Form B) with other biologically active (particularly fungicidal) compounds or agents (i.e. active ingredients) can result in a greater-than-additive (i.e. synergistic) effect. Reducing the quantity of active ingredients released in the environment while ensuring effective pest control is always desirable. When synergism of fungicidal active ingredients occurs at application rates giving agronomically satisfactory levels of fungal control, such combinations can be advantageous for reducing crop production cost and decreasing environmental load. This synergism has been described as "the cooperative action of two components of a mixture, such that the total effect is greater or more prolonged than the sum of the effects of the two (or more) taken independently" (see Tames, P. M. L., *Neth. J. Plant Pathology*, (1964), 70, 73-80).

Of note is a combination of a solid form of Compound 1 (e.g., polymorph Form B) with at least one other fungicidal active ingredient. Of particular note is such a combination where the other fungicidal active ingredient has different site of action from Compound 1. In certain instances, a combination with at least one other fungicidal active ingredient having a similar spectrum of control but a different site of action will be particularly advantageous for resistance management. Thus, a composition of the present invention can further comprise a biologically effective amount of at least one additional fungicidal active ingredient having a similar spectrum of control but a different site of action.

Of further note are combinations of a solid form of Compound 1 (e.g., polymorph Form B) with the fungicides: amisulbrom, azoxystrobin, benthiavalicarb, benthiavalicarb-isopropyl, Bordeaux mixture, boscalid (nicobifen), carboxin, chlorothalonil, copper hydroxide, copper oxychloride, copper sulfate, cyazofamid, cymoxanil, cyproconazole, difenoconazole, dimethomorph, famoxadone, fluazinam, fludioxonil, fluopicolide, flusilazole, folpet, fosetyl-aluminum, Initium® (ametoctradin), iprovalicarb, kresoxim-methyl, mancozeb, mandipropamid, metalaxyl M, myclobutanil, orysastrobin, penthiopyrad, phosphonic acid, phosphorous acids and salts, picoxystrobin, propamocarb, propamocarb-HCl, propiconazole, proquinazid, pyraclostrobin, quinoxyfen, spiroxamine, tebuconazole, tetraconazole, trifloxystrobin or valiphenal.

For embodiments where one or more of these various mixing partners are used, the weight ratio of these various mixing partners (in total) to a solid form of Compound 1 (e.g., polymorph Form B) is typically between about 1:3000 and about 3000:1. Of note are weight ratios between about 1:300 and about 300:1 (for example ratios between about 1:30 and about 30:1). One skilled in the art can easily determine through simple experimentation the biologically effective amounts of active ingredients necessary for the desired spectrum of biological activity. It will be evident that including these additional components may expand the spectrum of diseases controlled beyond the spectrum controlled by solid forms of Compound 1 alone.

Specific weight ratios illustrative of the mixtures, compositions and methods of the present invention are listed in Table 7. The first column of Table 7 lists the specific mixing partner compound (e.g., "Acibenzolar-S-methyl" in the first line). The second, third and fourth columns of Table 7 lists ranges of weight ratios for rates at which the mixing partner compound is typically applied relative to a solid form of Compound 1. Thus, for example, the first line of Table 7 specifically discloses that combination of acibenzolar-S-methyl with a solid form of Compound 1 (e.g., polymorph Form B) is typically applied in a weight ratio between 22:1 to 1:60. The remaining lines of Table 7 are to be construed similarly.

TABLE 7

| Mixing Partner | Typical Weight Ratio | More Typical Weight Ratio | Most Typical Weight Ratio |
|---|---|---|---|
| acibenzolar-S-methyl | 22:1 to 1:60 | 7:1 to 1:20 | 4:1 to 1:3 |
| aldimorph | 300:1 to 1:1 | 100:1 to 3:1 | 60:1 to 8:1 |
| ametoctradin | 90:1 to 1:6 | 30:1 to 1:2 | 24:1 to 3:1 |
| amisulbrom | 60:1 to 1:6 | 20:1 to 1:2 | 12:1 to 2:1 |
| anilazine | 900:1 to 4:1 | 300:1 to 10:1 | 180:1 to 27:1 |
| azaconazole | 75:1 to 1:6 | 25:1 to 1:2 | 18:1 to 2:1 |
| azoxystrobin | 90:1 to 1:4 | 30:1 to 1:2 | 24:1 to 3:1 |
| benalaxyl | 45:1 to 1:6 | 15:1 to 1:2 | 12:1 to 2:1 |

TABLE 7-continued

| Mixing Partner | Typical Weight Ratio | More Typical Weight Ratio | Most Typical Weight Ratio |
|---|---|---|---|
| benalaxyl-M | 45:1 to 1:12 | 15:1 to 1:4 | 9:1 to 1:1 |
| benodanil | 180:1 to 1:2 | 60:1 to 2:1 | 36:1 to 4:1 |
| benomyl | 450:1 to 1:2 | 150:1 to 3:1 | 90:1 to 10:1 |
| benthiavalicarb | 22:1 to 1:12 | 7:1 to 1:4 | 4:1 to 1:2 |
| benthiavalicarb-isopropyl | 22:1 to 1:12 | 7:1 to 1:4 | 4:1 to 1:2 |
| bethoxazin | 1500:1 to 1:12 | 500:1 to 1:4 | 120:1 to 14:1 |
| binapacryl | 1500:1 to 1:12 | 500:1 to 1:4 | 120:1 to 14:1 |
| biphenyl | 1500:1 to 1:12 | 500:1 to 1:4 | 120:1 to 14:1 |
| bitertanol | 150:1 to 1:2 | 50:1 to 2:1 | 30:1 to 6:1 |
| bixafen | 120:1 to 1:3 | 40:1 to 1:1 | 18:1 to 3:1 |
| blasticidin-S | 30:1 to 1:30 | 10:1 to 1:10 | 1:1 to 1:4 |
| Bordeaux mixture (tribasic copper sulfate) | 4500:1 to 4:1 | 1500:1 to 10:1 | 360:1 to 40:1 |
| boscalid | 180:1 to 1:2 | 60:1 to 2:1 | 36:1 to 4:1 |
| bromuconazole | 150:1 to 1:3 | 50:1 to 1:1 | 24:1 to 3:1 |
| bupirimate | 30:1 to 1:30 | 10:1 to 1:10 | 2:1 to 1:4 |
| captafol | 900:1 to 1:2 | 300:1 to 3:1 | 120:1 to 14:1 |
| captan | 900:1 to 1:2 | 300:1 to 3:1 | 120:1 to 14:1 |
| carbendazim | 450:1 to 1:2 | 150:1 to 3:1 | 90:1 to 10:1 |
| carboxin | 180:1 to 1:2 | 60:1 to 2:1 | 36:1 to 4:1 |
| carpropamid | 150:1 to 1:3 | 50:1 to 1:1 | 24:1 to 3:1 |
| chloroneb | 3000:1 to 4:1 | 1000:1 to 10:1 | 800:1 to 107:1 |
| chlorothalonil | 900:1 to 1:2 | 300:1 to 3:1 | 120:1 to 14:1 |
| chlozolinate | 450:1 to 2:1 | 150:1 to 5:1 | 90:1 to 14:1 |
| clotrimazole | 150:1 to 1:3 | 50:1 to 1:1 | 24:1 to 3:1 |
| copper oxychloride | 2250:1 to 4:1 | 750:1 to 10:1 | 480:1 to 54:1 |
| copper salts such as copper sulfate and copper hydroxide | 1200:1 to 1:2 | 400:1 to 2:1 | 60:1 to 7:1 |
| cyazofamid | 45:1 to 1:6 | 15:1 to 1:2 | 9:1 to 2:1 |
| cyflufenamid | 15:1 to 1:30 | 5:1 to 1:10 | 3:1 to 1:3 |
| cymoxanil | 60:1 to 1:6 | 20:1 to 1:2 | 14:1 to 2:1 |
| cyproconazole | 45:1 to 1:6 | 15:1 to 1:2 | 9:1 to 2:1 |
| cyprodinil | 225:1 to 1:3 | 75:1 to 1:1 | 36:1 to 4:1 |
| dichlofluanid | 1500:1 to 1:12 | 500:1 to 1:4 | 120:1 to 14:1 |
| diclocymet | 1500:1 to 1:12 | 500:1 to 1:4 | 120:1 to 14:1 |
| diclomezine | 150:1 to 1:3 | 50:1 to 1:1 | 30:1 to 4:1 |
| dicloran | 1500:1 to 1:12 | 500:1 to 1:4 | 120:1 to 14:1 |
| diethofencarb | 225:1 to 1:3 | 75:1 to 1:1 | 60:1 to 7:1 |
| difenoconazole | 45:1 to 1:12 | 15:1 to 1:4 | 6:1 to 1:2 |
| diflumetorim | 1500:1 to 1:12 | 500:1 to 1:4 | 120:1 to 14:1 |
| dimethirimol | 30:1 to 1:30 | 10:1 to 1:10 | 2:1 to 1:4 |
| dimethomorph | 90:1 to 1:2 | 30:1 to 2:1 | 24:1 to 4:1 |
| dimoxystrobin | 90:1 to 1:6 | 30:1 to 1:2 | 18:1 to 2:1 |
| diniconazole | 30:1 to 1:12 | 10:1 to 1:4 | 8:1 to 1:1 |
| diniconazole M | 30:1 to 1:30 | 10:1 to 1:10 | 6:1 to 1:2 |
| dinocap | 75:1 to 1:3 | 25:1 to 1:1 | 18:1 to 3:1 |
| dithianon | 150:1 to 1:2 | 50:1 to 3:1 | 40:1 to 7:1 |
| dodemorph | 300:1 to 1:1 | 100:1 to 3:1 | 60:1 to 8:1 |
| dodine | 300:1 to 2:1 | 100:1 to 5:1 | 80:1 to 14:1 |
| edifenphos | 300:1 to 1:3 | 100:1 to 1:1 | 30:1 to 4:1 |
| enestroburin | 90:1 to 1:6 | 30:1 to 1:2 | 18:1 to 2:1 |
| epoxiconazole | 37:1 to 1:12 | 12:1 to 1:4 | 10:1 to 2:1 |
| ethaboxam | 75:1 to 1:3 | 25:1 to 1:1 | 18:1 to 3:1 |
| etridiazole | 300:1 to 1:3 | 100:1 to 1:1 | 60:1 to 7:1 |
| famoxadone | 90:1 to 1:6 | 30:1 to 1:2 | 18:1 to 2:1 |
| fenamidone | 60:1 to 1:6 | 20:1 to 1:2 | 16:1 to 2:1 |
| fenarimol | 30:1 to 1:30 | 10:1 to 1:10 | 3:1 to 1:3 |
| fenbuconazole | 30:1 to 1:10 | 10:1 to 1:4 | 6:1 to 1:2 |
| fenfuram | 180:1 to 1:2 | 60:1 to 2:1 | 36:1 to 4:1 |
| fenhexamid | 300:1 to 2:1 | 100:1 to 5:1 | 80:1 to 14:1 |
| fenoxanil | 1500:1 to 1:12 | 500:1 to 1:4 | 120:1 to 14:1 |
| fenpiclonil | 750:1 to 1:3 | 250:1 to 1:1 | 120:1 to 14:1 |
| fenpropidin | 300:1 to 1:1 | 100:1 to 3:1 | 60:1 to 8:1 |
| fenpropimorph | 300:1 to 1:1 | 100:1 to 3:1 | 60:1 to 8:1 |
| fenpyrazamine | 150:1 to 1:3 | 50:1 to 1:1 | 36:1 to 4:1 |
| fentin acetate | 150:1 to 1:3 | 50:1 to 1:1 | 24:1 to 3:1 |
| fentin chloride | 150:1 to 1:3 | 50:1 to 1:1 | 24:1 to 3:1 |
| fentin hydroxide | 150:1 to 1:3 | 50:1 to 1:1 | 24:1 to 3:1 |
| ferbam | 3000:1 to 2:1 | 1000:1 to 5:1 | 240:1 to 27:1 |
| ferimzone | 300:1 to 1:2 | 100:1 to 2:1 | 60:1 to 7:1 |
| fluazinam | 225:1 to 1:2 | 75:1 to 2:1 | 30:1 to 6:1 |
| fludioxonil | 75:1 to 1:4 | 25:1 to 1:2 | 18:1 to 2:1 |
| flumetover | 90:1 to 1:2 | 30:1 to 2:1 | 24:1 to 4:1 |
| flumorph | 90:1 to 1:6 | 30:1 to 1:2 | 24:1 to 3:1 |
| fluopicolide | 37:1 to 1:6 | 12:1 to 1:2 | 9:1 to 2:1 |
| fluopyram | 150:1 to 1:30 | 50:1 to 1:10 | 24:1 to 3:1 |
| fluoromide | 1500:1 to 4:1 | 500:1 to 10:1 | 300:1 to 34:1 |
| fluoxastrobin | 45:1 to 1:6 | 15:1 to 1:2 | 12:1 to 2:1 |

TABLE 7-continued

| Mixing Partner | Typical Weight Ratio | More Typical Weight Ratio | Most Typical Weight Ratio |
|---|---|---|---|
| fluquinconazole | 45:1 to 1:4 | 15:1 to 1:2 | 12:1 to 2:1 |
| flusilazole | 150:1 to 1:3 | 50:1 to 1:1 | 24:1 to 3:1 |
| flusulfamide | 900:1 to 2:1 | 300:1 to 5:1 | 120:1 to 14:1 |
| flutianil | 75:1 to 1:12 | 25:1 to 1:4 | 12:1 to 2:1 |
| flutolanil | 180:1 to 1:2 | 60:1 to 2:1 | 36:1 to 4:1 |
| flutriafol | 45:1 to 1:4 | 15:1 to 1:2 | 12:1 to 2:1 |
| fluxapyroxad | 90:1 to 1:6 | 30:1 to 1:2 | 24:1 to 3:1 |
| folpet | 900:1 to 1:2 | 300:1 to 3:1 | 120:1 to 14:1 |
| fosetyl-aluminum | 2250:1 to 5:1 | 750:1 to 15:1 | 240:1 to 40:1 |
| fuberidazole | 450:1 to 1:2 | 150:1 to 3:1 | 90:1 to 10:1 |
| furalaxyl | 150:1 to 1:15 | 50:1 to 1:5 | 12:1 to 2:1 |
| furametpyr | 1500:1 to 1:12 | 500:1 to 1:4 | 120:1 to 14:1 |
| guazatine | 1500:1 to 1:12 | 500:1 to 1:4 | 120:1 to 14:1 |
| hexaconazole | 150:1 to 1:12 | 50:1 to 1:4 | 15:1 to 2:1 |
| hymexazol | 2250:1 to 4:1 | 750:1 to 10:1 | 600:1 to 67:1 |
| imazalil | 75:1 to 1:6 | 25:1 to 1:2 | 15:1 to 2:1 |
| imibenconazole | 150:1 to 1:12 | 50:1 to 1:4 | 15:1 to 2:1 |
| iodocarb | 1500:1 to 1:12 | 500:1 to 1:4 | 120:1 to 14:1 |
| ipconazole | 150:1 to 1:12 | 50:1 to 1:4 | 15:1 to 2:1 |
| iprobenfos | 1500:1 to 1:12 | 500:1 to 1:4 | 120:1 to 14:1 |
| iprodione | 1200:1 to 2:1 | 400:1 to 5:1 | 120:1 to 14:1 |
| iprovalicarb | 90:1 to 1:3 | 30:1 to 1:1 | 18:1 to 3:1 |
| isoprothiolane | 1500:1 to 4:1 | 500:1 to 10:1 | 360:1 to 40:1 |
| isopyrazam | 120:1 to 1:3 | 40:1 to 1:1 | 18:1 to 3:1 |
| isotianil | 120:1 to 1:3 | 40:1 to 1:1 | 18:1 to 3:1 |
| kasugamycin | 75:1 to 1:30 | 25:1 to 1:10 | 3:1 to 1:3 |
| kresoxim-methyl | 75:1 to 1:6 | 25:1 to 1:2 | 18:1 to 2:1 |
| mancozeb | 1800:1 to 2:1 | 600:1 to 4:1 | 180:1 to 20:1 |
| mandipropamid | 60:1 to 1:6 | 20:1 to 1:2 | 16:1 to 2:1 |
| maneb | 1800:1 to 2:1 | 600:1 to 4:1 | 180:1 to 20:1 |
| mepanipyrim | 180:1 to 1:1 | 60:1 to 3:1 | 48:1 to 8:1 |
| mepronil | 75:1 to 1:12 | 25:1 to 1:4 | 12:1 to 2:1 |
| meptyldinocap | 75:1 to 1:3 | 25:1 to 1:1 | 18:1 to 3:1 |
| metalaxyl | 150:1 to 1:15 | 50:1 to 1:5 | 12:1 to 2:1 |
| metalaxyl-M | 75:1 to 1:15 | 25:1 to 1:5 | 6:1 to 1:1 |
| metconazole | 30:1 to 1:6 | 10:1 to 1:2 | 8:1 to 2:1 |
| methasulfocarb | 1500:1 to 1:12 | 500:1 to 1:4 | 120:1 to 14:1 |
| metiram | 1500:1 to 1:12 | 500:1 to 1:4 | 120:1 to 14:1 |
| metominostrobin | 90:1 to 1:4 | 30:1 to 1:2 | 24:1 to 3:1 |
| metrafenone | 60:1 to 1:4 | 20:1 to 1:2 | 16:1 to 2:1 |
| myclobutanil | 52:1 to 1:9 | 17:1 to 1:3 | 9:1 to 1:1 |
| naftifine | 1500:1 to 1:12 | 500:1 to 1:4 | 120:1 to 14:1 |
| neo-asozin (ferric methanearsonate) | 1500:1 to 1:12 | 500:1 to 1:4 | 120:1 to 14:1 |
| nuarimol | 150:1 to 1:3 | 50:1 to 1:1 | 24:1 to 3:1 |
| octhilinone | 1500:1 to 1:12 | 500:1 to 1:4 | 120:1 to 14:1 |
| ofurace | 150:1 to 1:15 | 50:1 to 1:5 | 12:1 to 2:1 |
| orysastrobin | 90:1 to 1:4 | 30:1 to 1:2 | 24:1 to 3:1 |
| oxadixyl | 150:1 to 1:15 | 50:1 to 1:5 | 12:1 to 2:1 |
| oxolinic acid | 300:1 to 1:3 | 100:1 to 1:1 | 60:1 to 7:1 |
| oxpoconazole | 150:1 to 1:12 | 50:1 to 1:4 | 15:1 to 2:1 |
| oxycarboxin | 180:1 to 1:2 | 60:1 to 2:1 | 36:1 to 4:1 |
| oxytetracycline | 150:1 to 1:3 | 50:1 to 1:1 | 30:1 to 4:1 |
| pefurazoate | 1500:1 to 1:12 | 500:1 to 1:4 | 120:1 to 14:1 |
| penconazole | 15:1 to 1:15 | 5:1 to 1:5 | 3:1 to 1:2 |
| pencycuron | 1500:1 to 2:1 | 500:1 to 5:1 | 90:1 to 14:1 |
| penflufen | 120:1 to 1:3 | 40:1 to 1:1 | 18:1 to 3:1 |
| penthiopyrad | 120:1 to 1:3 | 40:1 to 1:1 | 18:1 to 3:1 |
| phosphorous acid and salts | 1500:1 to 1:12 | 500:1 to 1:4 | 120:1 to 14:1 |
| phthalide | 1500:1 to 1:12 | 500:1 to 1:4 | 120:1 to 14:1 |
| picoxystrobin | 75:1 to 1:6 | 25:1 to 1:2 | 15:1 to 2:1 |
| piperalin | 150:1 to 1:3 | 50:1 to 1:1 | 24:1 to 3:1 |
| polyoxin | 150:1 to 1:3 | 50:1 to 1:1 | 30:1 to 4:1 |
| probenazole | 150:1 to 1:3 | 50:1 to 1:1 | 24:1 to 3:1 |
| prochloraz | 225:1 to 1:2 | 75:1 to 3:1 | 60:1 to 7:1 |
| procymidone | 450:1 to 1:1 | 150:1 to 3:1 | 90:1 to 10:1 |
| propamocarb | 300:1 to 2:1 | 100:1 to 5:1 | 80:1 to 14:1 |
| propamocarb-hydrochloride | 300:1 to 2:1 | 100:1 to 5:1 | 80:1 to 14:1 |
| propiconazole | 45:1 to 1:6 | 15:1 to 1:2 | 12:1 to 2:1 |
| propineb | 450:1 to 2:1 | 150:1 to 5:1 | 90:1 to 14:1 |
| proquinazid | 30:1 to 1:12 | 10:1 to 1:4 | 6:1 to 1:2 |
| prothioconazole | 60:1 to 1:6 | 20:1 to 1:2 | 15:1 to 2:1 |
| pyraclostrobin | 90:1 to 1:6 | 30:1 to 1:2 | 18:1 to 2:1 |
| pyrametostrobin | 90:1 to 1:6 | 30:1 to 1:2 | 18:1 to 2:1 |
| pyraoxystrobin | 90:1 to 1:6 | 30:1 to 1:2 | 18:1 to 2:1 |
| pyrazophos | 1500:1 to 1:12 | 500:1 to 1:4 | 120:1 to 14:1 |
| pyribencarb | 150:1 to 1:2 | 50:1 to 2:1 | 36:1 to 4:1 |
| pyrifenox | 150:1 to 1:3 | 50:1 to 1:1 | 24:1 to 3:1 |

TABLE 7-continued

| Mixing Partner | Typical Weight Ratio | More Typical Weight Ratio | Most Typical Weight Ratio |
|---|---|---|---|
| pyrimethanil | 300:1 to 1:2 | 100:1 to 2:1 | 30:1 to 4:1 |
| pyriofenone | 90:1 to 1:6 | 30:1 to 1:2 | 24:1 to 3:1 |
| pyroquilon | 150:1 to 1:3 | 50:1 to 1:1 | 24:1 to 3:1 |
| pyrrolnitrin | 1500:1 to 1:12 | 500:1 to 1:4 | 120:1 to 14:1 |
| quinmethionate | 1500:1 to 1:12 | 500:1 to 1:4 | 120:1 to 14:1 |
| quinoxyfen | 45:1 to 1:6 | 15:1 to 1:2 | 9:1 to 2:1 |
| quintozene | 1500:1 to 1:12 | 500:1 to 1:4 | 120:1 to 14:1 |
| sedaxane | 120:1 to 1:3 | 40:1 to 1:1 | 18:1 to 3:1 |
| silthiofam | 75:1 to 1:6 | 25:1 to 1:2 | 18:1 to 2:1 |
| simeconazole | 150:1 to 1:12 | 50:1 to 1:4 | 15:1 to 2:1 |
| spiroxamine | 225:1 to 1:2 | 75:1 to 3:1 | 45:1 to 7:1 |
| streptomycin | 150:1 to 1:3 | 50:1 to 1:1 | 30:1 to 4:1 |
| sulfur | 3000:1 to 9:1 | 1000:1 to 25:1 | 600:1 to 67:1 |
| tebuconazole | 75:1 to 1:6 | 25:1 to 1:2 | 15:1 to 2:1 |
| tebufloquin | 45:1 to 1:6 | 15:1 to 1:2 | 9:1 to 2:1 |
| tecloftalam | 1500:1 to 1:12 | 500:1 to 1:4 | 120:1 to 14:1 |
| tecnazene | 1500:1 to 1:12 | 500:1 to 1:4 | 120:1 to 14:1 |
| terbinafine | 1500:1 to 1:12 | 500:1 to 1:4 | 120:1 to 14:1 |
| tetraconazole | 150:1 to 1:12 | 50:1 to 1:4 | 15:1 to 2:1 |
| thiabendazole | 450:1 to 1:2 | 150:1 to 3:1 | 90:1 to 10:1 |
| thifluzamide | 150:1 to 1:3 | 50:1 to 1:1 | 24:1 to 3:1 |
| thiophanate | 450:1 to 2:1 | 150:1 to 4:1 | 90:1 to 11:1 |
| thiophanate-methyl | 450:1 to 2:1 | 150:1 to 4:1 | 90:1 to 11:1 |
| thiram | 1500:1 to 2:1 | 500:1 to 5:1 | 300:1 to 34:1 |
| tiadinil | 120:1 to 1:3 | 40:1 to 1:1 | 18:1 to 3:1 |
| tolclofos-methyl | 1500:1 to 2:1 | 500:1 to 5:1 | 300:1 to 34:1 |
| tolylfluanid | 1500:1 to 1:12 | 500:1 to 1:4 | 120:1 to 14:1 |
| triadimefon | 150:1 to 1:12 | 50:1 to 1:4 | 15:1 to 2:1 |
| triadimenol | 150:1 to 1:12 | 50:1 to 1:4 | 15:1 to 2:1 |
| triazoxide | 1500:1 to 1:12 | 500:1 to 1:4 | 120:1 to 14:1 |
| tricyclazole | 150:1 to 1:3 | 50:1 to 1:1 | 24:1 to 3:1 |
| tridemorph | 300:1 to 1:1 | 100:1 to 3:1 | 60:1 to 8:1 |
| trifloxystrobin | 60:1 to 1:6 | 20:1 to 1:2 | 16:1 to 2:1 |
| triflumizole | 150:1 to 1:3 | 50:1 to 1:1 | 24:1 to 3:1 |
| triforine | 150:1 to 1:3 | 50:1 to 1:1 | 24:1 to 3:1 |
| trimorphamide | 450:1 to 1:3 | 150:1 to 1:1 | 60:1 to 7:1 |
| triticonazole | 150:1 to 1:12 | 50:1 to 1:4 | 15:1 to 2:1 |
| uniconazole | 150:1 to 1:12 | 50:1 to 1:4 | 15:1 to 2:1 |
| validamycin | 1500:1 to 1:12 | 500:1 to 1:4 | 24:1 to 3:1 |
| valifenalate | 60:1 to 1:6 | 20:1 to 1:2 | 16:1 to 2:1 |
| valiphenal | 60:1 to 1:6 | 20:1 to 1:2 | 16:1 to 2:1 |
| vinclozolin | 1200:1 to 2:1 | 400:1 to 5:1 | 120:1 to 14:1 |
| zineb | 1500:1 to 2:1 | 500:1 to 5:1 | 300:1 to 34:1 |
| ziram | 1500:1 to 2:1 | 500:1 to 5:1 | 300:1 to 34:1 |
| zoxamide | 60:1 to 1:6 | 20:1 to 1:2 | 16:1 to 2:1 |
| 5-chloro-6-(2,4,6-trifluorophenyl)-7-(4-metylpiperidin-1-yl)[1,2,4]triazolo-[1,5-a]pyrimidine | 150:1 to 1:12 | 50:1 to 1:4 | 12:1 to 2:1 |
| N-[2-[4-[[3-(4-chlorophenyl)-2-propyn-1-yl]oxy]-3-methoxyphenyl]ethyl]-3-methyl-2-[(methylsulfonyl)amino]butanamide | 60:1 to 1:6 | 20:1 to 1:2 | 16:1 to 2:1 |
| N-[2-[4-[[3-(4-chlorophenyl)-2-propyn-1-yl]oxy]-3-methoxyphenyl]ethyl]-3-methyl-2-[(ethylsulfonyl)amino]butanamide | 60:1 to 1:6 | 20:1 to 1:2 | 16:1 to 2:1 |
| 2-butoxy-6-iodo-3-propyl-4H-1-benzopyran-4-one | 30:1 to 1:12 | 10:1 to 1:4 | 6:1 to 1:2 |
| 3-[5-(4-chlorophenyl)-2,3-dimethyl-3-isoxazolidinyl]pyridine | 150:1 to 1:3 | 50:1 to 1:1 | 24:1 to 3:1 |
| 4-fluorophenyl N-[1-[[[1-(4-cyanophenyl)ethyl]sulfonyl]methyl]propyl]carbamate | 60:1 to 1:6 | 20:1 to 1:2 | 16:1 to 2:1 |
| N-[[(cyclopropylmethoxy)amino][6-(difluoromethoxy)-2,3-difluorophenyl]-methylene]benzeneacetamide | 15:1 to 1:30 | 5:1 to 1:10 | 3:1 to 1:3 |
| α-[methoxyimino]-N-methyl-2-[[[1-[3-(trifluoromethyl)phenyl]ethoxy]imino]-methyl]benzeneacetamide | 90:1 to 1:6 | 30:1 to 1:2 | 24:1 to 3:1 |
| N'-[4-[4-chloro-3-(trifluoromethyl)phenoxy]-2,5-dimethylphenyl]-N-ethyl-N-methylmethanimidamide | 150:1 to 1:6 | 50:1 to 1:2 | 24:1 to 3:1 |
| N-(4-chloro-2-nitrophenyl)-N-ethyl-4-methylbenzenesulfonamide | 150:1 to 1:6 | 50:1 to 1:2 | 24:1 to 3:1 |
| 2-[[[3-(2,6-dichlorophenyl)-1-methyl-2-propen-1-ylidene]amino]oxy]methyl]-α-(methoxyimino)-N-methylbenzeneacetamide | 90:1 to 1:6 | 30:1 to 1:2 | 18:1 to 2:1 |
| 2-[[[3-(2,6-dichlorophenyl)-1-methyl-2-propen-1-ylidene]amino]oxy]methyl]-α- | 150:1 to 1:3 | 50:1 to 1:1 | 36:1 to 4:1 |

TABLE 7-continued

| Mixing Partner | Typical Weight Ratio | More Typical Weight Ratio | Most Typical Weight Ratio |
|---|---|---|---|
| (methoxyimino)-N-methylbenzeneacetamide | | | |
| 3-chloro-5-(4-chlorophenyl)-6-methyl-4-(2,4,6-trifluorophenyl)pyridazine | 90:1 to 1:6 | 30:1 to 1:2 | 24:1 to 3:1 |
| N-[9-(dichloromethylene)-1,2,3,4-tetrahydro-1,4-methanonaphthalen-5-yl]-3-(difluoromethyl)-1-methyl-1H-pyrazole-4-carboxamide | 90:1 to 1:6 | 30:1 to 1:2 | 24:1 to 3:1 |
| pentyl N-[6-[[[[(1-methyl-1H-tetrazol-5-yl)phenylmethylene]amino]oxy]methyl]-2-pyridinyl]carbamate | 90:1 to 1:6 | 30:1 to 1:2 | 24:1 to 3:1 |

Examples of other biologically active compounds or agents with which a solid form of Compound 1 can be formulated are: insecticides such as abamectin, acephate, acetamiprid, amidoflumet (S-1955), avermectin, azadirachtin, azinphos-methyl, bifenthrin, bifenazate, 3-bromo-1-(3-chloro-2-pyridinyl)-N-[4-cyano-2-methyl-6-[(methylamino)carbonyl]phenyl]-1H-pyrazole-5-carboxamide, buprofezin, carbofaran, cartap, chlorantraniliprole chlorfenapyr, chlorfluazuron, chlorpyrifos, chlorpyrifos-methyl, chromafenozide, clothianidin, cyflumetofen, cyfluthrin, beta-cyfluthrin, cyhalothrin, lambda-cyhalothrin, cypermethrin, cyromazine, deltamethrin, diafenthiuron, diazinon, dieldrin, diflubenzuron, dimefluthrin, dimethoate, dinotefuran, diofenolan, emamectin, endosulfan, esfenvalerate, ethiprole, fenothiocarb, fenoxycarb, fenpropathrin, fenvalerate, fipronil, flonicamid, flubendiamide, flucythrinate, tau-fluvalinate, flufenerim (UR-50701), flufenoxuron, fonophos, halofenozide, hexaflumuron, hydramethylnon, imidacloprid, indoxacarb, isofenphos, lufenuron, malathion, meperfluthrin, metaflumnzone, metaldehyde, methamidophos, methidathion, methomyl, methoprene, methoxychlor, metofluthrin, monocrotophos, methoxyfenozide, nitenpyram, nithiazine, novaluron, noviflumuron (XDE-007), oxamyl, parathion, parathion-methyl, permethrin, phorate, phosalone, phosmet, phosphamidon, pirimicarb, profenofos, profluthrin, pymetrozine, pyrafluprole, pyrethrin, pyridalyl, pyrifluquinazon, pyriprole, pyriproxyfen, rotenone, ryanodine, spinetoram, spinosad, spirodiclofen, spiromesifen (BSN 2060), spirotetramat, sulfoxaflor, sulprofos, tebufenozide, teflubenzuron, tefluthrin, terbufos, tetrachlorvinphos, tetramethylfluthrin, thiacloprid, thiamethoxam, thiodicarb, thiosultap-sodium, tralomethrin, triazamate, trichlorfon and triflumuron; and biological agents including entomopathogenic bacteria, such as *Bacillus thuringiensis* subsp. *aizawai*, *Bacillus thuringiensis* subsp. *urstaki*, and the encapsulated delta-endotoxins of *Bacillus thuringiensis* (e.g., Cellcap, MPV, MPVII); entomopathogenic fungi, such as green muscardine fungus; and entomopathogenic virus including baculovirus, nucleopolyhedro virus (NPV) such as HzNPV, AfNPV; and granulosis virus (GV) such as CpGV.

Solid forms of Compound 1 and compositions thereof can be applied to plants genetically transformed to express proteins toxic to invertebrate pests (such as *Bacillus thuringiensis* delta-endotoxins). The effect of the exogenously applied fungicidal compositions of this invention may be synergistic with the expressed toxin proteins.

Table 8 lists specific combinations of invertebrate pest control agents with a component (a) illustrative mixtures or compositions of the present invention comprising solid forms of Compound 1. The first column of Table 8 lists the specific invertebrate pest control agents (e.g., "Abamectin" in the first line). The second column of Table 8 lists the mode of action (if known) or chemical class of the invertebrate pest control agents. The third column of Table 8 lists embodiment(s) of ranges of weight ratios for rates at which the invertebrate pest control agent is typically applied relative to a component (a) (e.g., "50:1 to 1:50" of abamectin relative to an illustrative mixtures or compositions of the present invention comprising a solid form of Compound 1 by weight). Thus, for example, the first line of Table 8 specifically discloses the combination of a component (a) mixtures or compositions of the present invention comprising a solid form of Compound 1 (e.g., polymorph Form B) with abamectin is typically applied in a weight ratio between 50:1 to 1:50. The remaining lines of Table 8 are to be construed similarly.

TABLE 8

| Invertebrate Pest Control Agent | Mode of Action or Chemical Class | Typical Weight Ratio |
|---|---|---|
| Abamectin | macrocyclic lactones | 50:1 to 1:50 |
| Acetamiprid | neonicotinoids | 150:1 to 1:200 |
| Amitraz | octopamine receptor ligands | 200:1 to 1:100 |
| Avermectin | macrocyclic lactones | 50:1 to 1:50 |
| Azadirachtin | ecdysone agonists | 100:1 to 1:120 |
| Beta-cyfluthrin | sodium channel modulators | 150:1 to 1:200 |
| Bifenthrin | sodium channel modulators | 100:1 to 1:10 |
| Buprofezin | chitin synthesis inhibitors | 500:1 to 1:50 |
| Cartap | nereistoxin analogs | 100:1 to 1:200 |
| Chlorantraniliprole | ryanodine receptor ligands | 100:1 to 1:120 |
| Chlorfenapyr | mitochondrial electron transport inhibitors | 300:1 to 1:200 |
| Chlorpyrifos | cholinesterase inhibitors | 500:1 to 1:200 |
| Clothianidin | neonicotinoids | 100:1 to 1:400 |
| Cyfluthrin | sodium channel modulators | 150:1 to 1:200 |
| Cyhalothrin | sodium channel modulators | 150:1 to 1:200 |
| Cypermethrin | sodium channel modulators | 150:1 to 1:200 |
| Cyromazine | chitin synthesis inhibitors | 400:1 to 1:50 |
| Deltamethrin | sodium channel modulators | 50:1 to 1:400 |
| Dieldrin | cyclodiene insecticides | 200:1 to 1:100 |
| Dinotefuran | neonicotinoids | 150:1 to 1:200 |
| Diofenolan | molting inhibitor | 150:1 to 1:200 |
| Emamectin | macrocyclic lactones | 50:1 to 1:10 |
| Endosulfan | cyclodiene insecticides | 200:1 to 1:100 |
| Esfenvalerate | sodium channel modulators | 100:1 to 1:400 |
| Ethiprole | GABA-regulated chloride channel blockers | 200:1 to 1:100 |
| Fenothiocarb | | 150:1 to 1:200 |
| Fenoxycarb | juvenile hormone mimics | 500:1 to 1:100 |
| Fenvalerate | sodium channel modulators | 150:1 to 1:200 |
| Fipronil | GABA-regulated chloride channel blockers | 150:1 to 1:100 |
| Flonicamid | | 200:1 to 1:100 |
| Flubendiamide | ryanodine receptor ligands | 100:1 to 1:120 |
| Flufenoxuron | chitin synthesis inhibitors | 200:1 to 1:100 |
| Hexaflumuron | chitin synthesis inhibitors | 300:1 to 1:50 |
| Hydramethylnon | mitochondrial electron transport inhibitors | 150:1 to 1:250 |
| Imidacloprid | neonicotinoids | 1000:1 to 1:1000 |
| Indoxacarb | sodium channel modulators | 200:1 to 1:50 |
| Lambda-cyhalothrin | sodium channel modulators | 50:1 to 1:250 |

TABLE 8-continued

| Invertebrate Pest Control Agent | Mode of Action or Chemical Class | Typical Weight Ratio |
|---|---|---|
| Lufenuron | chitin synthesis inhibitors | 500:1 to 1:250 |
| Metaflumizone | | 200:1 to 1:200 |
| Methomyl | cholinesterase inhibitors | 500:1 to 1:100 |
| Methoprene | juvenile hormone mimics | 500:1 to 1:100 |
| Methoxyfenozide | ecdysone agonists | 50:1 to 1:50 |
| Nitenpyram | neonicotinoids | 150:1 to 1:200 |
| Nithiazine | neonicotinoids | 150:1 to 1:200 |
| Novaluron | chitin synthesis inhibitors | 500:1 to 1:150 |
| Oxamyl | cholinesterase inhibitors | 200:1 to 1:200 |
| Pymetrozine | | 200:1 to 1:100 |
| Pyrethrin | sodium channel modulators | 100:1 to 1:10 |
| Pyridaben | mitochondrial electron transport inhibitors | 200:1 to 1:100 |
| Pyridalyl | | 200:1 to 1:100 |
| Pyriproxyfen | juvenile hormone mimics | 500:1 to 1:100 |
| Ryanodine | ryanodine receptor ligands | 100:1 to 1:120 |
| Spinetoram | macrocyclic lactones | 150:1 to 1:100 |
| Spinosad | macrocyclic lactones | 500:1 to 1:10 |
| Spirodiclofen | lipid biosynthesis inhibitors | 200:1 to 1:200 |
| Spiromesifen | lipid biosynthesis inhibitors | 200:1 to 1:200 |
| Tebufenozide | ecdysone agonists | 500:1 to 1:250 |
| Thiacloprid | neonicotinoids | 100:1 to 1:200 |
| Thiamethoxam | neonicotinoids | 1250:1 to 1:1000 |
| Thiodicarb | cholinesterase inhibitors | 500:1 to 1:400 |
| Thiosultap-sodium | | 150:1 to 1:100 |
| Tralomethrin | sodium channel modulators | 150:1 to 1:200 |
| Triazamate | cholinesterase inhibitors | 250:1 to 1:100 |
| Triflumuron | chitin synthesis inhibitors | 200:1 to 1:100 |
| *Bacillus thuringiensis* | biological agents | 50:1 to 1:10 |
| *Bacillus thuringiensis* delta-endotoxin | biological agents | 50:1 to 1:10 |
| NPV (e.g., Gemstar) | biological agents | 50:1 to 1:10 |

One embodiment of invertebrate pest control agents (e.g., insecticides and acaricides) for mixing with a solid form of Compound 1 (e.g., polymorph Form B) include sodium channel modulators such as bifenthrin, cypermethrin, cyhalothrin, lambda-cyhalothrin, cyfluthrin, beta-cyfluthrin, deltamethrin, dimefluthrin, esfenvalerate, fenvalerate, indoxacarb, metofluthrin, profluthrin, pyrethrin and tralomethrin; cholinesterase inhibitors such as chlorpyrifos, methomyl, oxamyl, thiodicarb and triazamate; neonicotinoids such as acetamiprid, clothianidin, dinotefuran, imidacloprid, nitenpyram, nithiazine, thiacloprid and thiamethoxam; insecticidal macrocyclic lactones such as spinetoram, spinosad, abamectin, avermectin and emamectin; GABA (γ-aminobutyric acid)-regulated chloride channel blockers such as endosulfan, ethiprole and fipronil; chitin synthesis inhibitors such as buprofezin, cyromazine, flufenoxuron, hexaflumuron, lufenuron, novaluron, noviflumuron and triflumuron; juvenile hormone mimics such as diofenolan, fenoxycarb, methoprene and pyriproxyfen; octopamine receptor ligands such as amitraz; ecdysone agonists such as azadirachtin, methoxyfenozide and tebufenozide; ryanodine receptor ligands such as ryanodine, anthranilic diamides such as chlorantraniliprole, flubendiamide, 3-bromo-1-(3-chloro-2-pyridinyl)-N-[4-cyano-2-methyl-6-[[(1-methylethyl)amino]carbonyl]phenyl]-1H-pyrazole-5-carboxamide, 3-bromo-1-(3-chloro-2-pyridinyl)-N-[4-cyano-2-methyl-6-[(methylamino)carbonyl]phenyl]-1H-pyrazole-5-carboxamide, 3-chloro-1-(3-chloro-2-pyridinyl)-N-[4-cyano-2-methyl-6-[(methylamino)carbonyl]phenyl]-1H-pyrazole-5-carboxamide and 3-chloro-1-(3-chloro-2-pyridinyl)-N-[4-cyano-2-methyl-6-[[(1-methylethyl)amino]carbonyl]phenyl]-1H-pyrazole-5-carboxamide; nereistoxin analogs such as cartap; mitochondrial electron transport inhibitors such as chlorfenapyr, hydramethylnon and pyridaben; lipid biosynthesis inhibitors such as spirodiclofen and spiromesifen; cyclodiene insecticides such as dieldrin; cyflumetofen; fenothiocarb; flonicamid; metaflumizone; pyrafluprole; pyridalyl; pyriprole; pymetrozine; spirotetramat; and thiosultap-sodium. One embodiment of biological agents for mixing with a solid form of Compound 1 include nucleopolyhedro virus such as HzNPV and AfNPV; *Bacillus thuringiensis* and encapsulated delta-endotoxins of *Bacillus thuringiensis* such as Cellcap, MPV and MPVII; as well as naturally occurring and genetically modified viral insecticides including members of the family Baculoviridae as well as entomophagous fungi. Of note is a composition comprising a solid form of Compound 1 and at least one additional biologically active compound or agent selected from the Invertebrate Pest Control Agents listed in Table 8 above.

General references for agricultural protectants (i.e. insecticides, fungicides, nematocides, acaricides, herbicides and biological agents) include *The Pesticide Manual, 13th Edition*, C. D. S. Tomlin, Ed., British Crop Protection Council, Farnham, Surrey, U.K., 2003 and *The BioPesticide Manual, 2nd Edition*, L. G. Copping, Ed., British Crop Protection Council, Farnham, Surrey, U.K., 2001.

The following TESTS demonstrate the control efficacy of formulations of solid forms of Compound 1 on specific pathogens. The pathogen control protection afforded by the formulations of solid forms of Compound 1 is not limited, however, to these species.

BIOLOGICAL EXAMPLES OF THE INVENTION

General protocol for preparing test suspensions for Tests A-E: The formulated compositions comprising polymorph Form B of Compound 1 tested were dispersed in water to provide aqueous suspensions containing 54 ppm of Compound 1. The diluted aqueous suspensions were then sprayed on young test plants just prior to the point of run-off to provide an application rate equivalent to 50 g ai/ha.

Test A

Grape seedlings were inoculated with a spore suspension of *Plasmopara viticola* (the causal agent of grape downy mildew) and incubated in a saturated atmosphere at 20° C. for 24 h. After an additional 24 hr drying period, the test suspension was sprayed on the grape seedlings and then moved to a growth chamber at 20° C. for 4 days, after which the test units were placed back into a saturated atmosphere at 20° C. for 24 h. Upon removal, disease ratings were visually made.

Test B

The test suspension was sprayed on grape seedlings which were then allowed to dry in a drying room overnight. The following day the seedlings were inoculated with a spore suspension of *Plasmopara viticola* (the causal agent of grape downy mildew) and incubated in a saturated atmosphere at 20° C. for 24 h. The seedlings were then moved to a growth chamber at 20° C. for 5 days, after which the test units were placed back into a saturated atmosphere at 20° C. for 24 h. Upon removal, disease ratings were visually made.

Test C

Four-week-old potato plants were inoculated with a spore suspension of *Phytophthora infestans* (the causal agent of potato late blight) and incubated in a saturated atmosphere at ° C. for 24 h. After a short drying period, the test suspension was sprayed on the potato plants and then moved to a growth chamber at 20° C. for 5 days, after which disease ratings were made.

Test D

The test suspension was sprayed on 4-week old potato plants which were then allowed to dry in a drying room overnight. The following day the plants were inoculated with a spore suspension of *Phytophthora infestans* (the causal agent of potato late blight) and incubated in a saturated atmosphere at 20° C. for 24 h, and then moved to a growth chamber at 20° C. for 4 days, after which disease ratings were visually made.

Test E

Four-week-old potato plants were inoculated with single 5 μl drop containing a spore suspension of *Phytophthora infestans* (the causal agent of potato late blight) on each of 2 leaves. They were incubated in a saturated atmosphere at 20° C. for 24 h. After an additional 24 hr drying period, the test suspension was sprayed on the potato plants and then they were moved to a growth chamber at 20° C. for 3 days after which the test units were placed back into a saturated atmosphere at 20° C. for 24 h and the % inhibition of sporulation was measured. Percent inhibition of sporulation was measured by excising lesions from the leaf; placing in sterile water and counting the number of spores per ml using a hemacytometer.

Results for Tests A-E are given in Table A. In the table, a rating of 100 indicates 100% disease control (Tests A-D) or 100% inhibition of sporulation (Test E), and a rating of 0 indicates no disease control (relative to the controls). A dash (-) indicates no test results. An asterisk (*) indicates the compounds were tested at 5.4 ppm.

TABLE A

| Formulation Example No. | Test A | Test B* | Test C | Test D* | Test E |
|---|---|---|---|---|---|
| 14d | 99 | 100 | 100 | 100 | — |
| 14c | 99 | 100 | 99 | 100 | — |
| 13a | 74 | 99 | 99 | 100 | — |
| 14a | 99 | 100 | 99 | 100 | — |
| 13b | 98 | 100 | 99 | 100 | — |
| 13c | 99 | 100 | 99 | 100 | — |
| 14e | 99 | 100 | 99 | 99 | — |
| 13d | 99 | — | 99 | — | — |
| 13e | 96 | — | 99 | 100 | — |
| 12b | — | — | — | — | 87 |
| 12c | — | — | 39 | — | — |

General protocol for preparing test suspensions for Tests F-H: The formulated compositions comprising polymorph Form B of Compound 1 tested were dispersed in water to provide aqueous suspensions of Compound 1. The diluted aqueous suspensions were then sprayed on young test plants just prior to the point of run-off to provide an application rate equivalent to 90 or 100 g ai/ha for grape testing (Test F) and an application rate of 25 g ai/ha for potato testing (Test G and H).

Test F

Grape seedlings were inoculated with a spore suspension of *Plasmopara viticola* (the causal agent of grape downy mildew) and incubated in a saturated atmosphere at 20° C. for 24 h. After an additional 48 hr drying in a growth chamber at 20° C., the test suspension was sprayed on the grape seedlings. Seedlings were then moved into a growth chamber at 20° C. for 4 days, after which the test units were placed back into a saturated atmosphere at 20° C. for 24 h. Upon removal, disease ratings were visually made.

Test G

Ten-week-old, clonally propagated potato plants were inoculated with a spore suspension of *Phytophthora infestans* (the causal agent of potato late blight) and incubated in a saturated atmosphere at 15° C. for 24 h. After a short drying period, the test suspension was sprayed on the potato plants and then moved to a growth chamber at 24° C. for 5 days, after which disease ratings were visually made.

Test H

Eleven-week-old, clonally propagated potato plants were inoculated with a spore suspension of *Phytophthora infestans* (the causal agent of potato late blight) and incubated in a saturated atmosphere at 15° C. for 24 h. After a short drying period, the test suspension was sprayed on the potato plants and then moved to a greenhouse at constant 27° C. for 5 days, after which disease ratings were visually made.

Results for Tests F-H are given in Table B. In the table, a rating of 100 indicates 100% disease control and a rating of 0 indicates no disease control (relative to the controls). A dash (-) indicates no test results for a particular formulation.

TABLE B

| Formulation Example No. | Test F | Test G | Test H |
|---|---|---|---|
| 16a | 90 | — | 66 |
| 16b | 88 | — | 91 |
| 16c | 92 | 90 | 83 |
| 16d | — | 100 | — |
| 16e | 94 | 100 | 89 |
| 16f | — | 100 | — |
| 16h | — | 99 | — |
| 16i | — | 90 | — |
| 16g | 91 | 99 | — |
| 16j | 95 | 100 | 93 |
| 16m | 93 | 99 | 97 |
| 16k | 86 | 100 | — |
| 16l | 96 | 100 | 91 |
| 15a | — | 82 | 69 |
| 15b | — | 93 | — |
| 15c | — | 92 | — |
| 15d | — | 98 | — |
| 15e | — | 96 | 87 |

General protocol for preparing test compositions for Tests I-K: Amisulbrom was formulated and ametoctradin was obtained as unformulated, technical-grade materials. Compound 1 were formulated as an oil dispersion containing a mixture of POE (polyoxyethylene) 40 sorbitol hexaoleate, POE 20 sorbitan trioleate, and alkyl-peg resin surfactants in a liquid carrier consisting of a distilled C18 fatty acid methyl ester. Ametoctradin was first dissolved in acetone and then suspended at the desired concentration (in ppm) in acetone and purified water (50/50 mix by volume) containing 250 ppm of the surfactant Trem® 014 (polyhydric alcohol esters). Amisulbrom was dispersed in sufficient water to give the desired concentration, and neither organic solvent nor surfactant was added to the suspension. The resulting test mixtures were then used in Tests I-K. Spraying a 200 ppm test mixture to the point of run-off on the test plants was the equivalent of a rate of 800 g/ha. The tests were replicated three times and the results reported as the mean average of the three replicates.

The presence of a synergistic effect between two active ingredients was established with the aid of the Colby equation (see Colby, S. R. "Calculating Synergistic and Antagonistic Responses of Herbicide Combinations", *Weeds*, (1967), 15, 20-22):

$$p = A + B - \left[\frac{A \times B}{100}\right].$$

Using the method of Colby, the presence of a synergistic interaction between two active ingredients is established by first calculating the predicted activity, p, of the mixture based on activities of the two components applied alone. If p is lower than the experimentally established effect, synergism has occurred. In the equation above, A is the fungicidal activity in percentage control of one component applied alone at rate x. The B term is the fungicidal activity in percentage control of the second component applied at rate y. The equation estimates p, the expected fungicidal activity of the mixture of A at rate x with B at rate y if their effects are strictly additive and no interaction has occurred.

Test I

The test mixture was sprayed to the point of run-off on tomato seedlings. The following day the seedlings were inoculated with a spore suspension of *Phytophthora infestans* (the causal agent of tomato late blight) and incubated in a saturated atmosphere at 20° C. for 24 h, and then moved to a growth chamber at 20° C. for 4 days, after which time disease ratings were made.

Test J

The test mixture was sprayed to the point of run-off on cucumber seedlings. The following day the seedlings were inoculated with a spore suspension of *Pseudoperonospora cubensis* (the causal agent of cucumber downy mildew) and incubated in saturated atmosphere at 20° C. for 24 h, and moved to a growth chamber at 20° C. for 6 days, after which time disease ratings were made.

Test K

Tomato seedlings were inoculated with a spore suspension of *Phytophthora infestans* (the causal agent of tomato late blight) and incubated in a saturated atmosphere at 20° C. for 17 h. After a short drying period, the test suspension was sprayed to the point of run-off on the tomato seedlings, which were then moved to a growth chamber at 20° C. for 3 days, after which time visual disease ratings were made.

Results for Tests I to K are given in Tables C-E. Each table corresponds to a set of evaluations performed together at the same time. In each table, a rating of 100 indicates 100% disease control and a rating of 0 indicates no disease control (relative to the controls). Columns labeled "Obsd" indicate the average of results observed from three replications. Columns labeled "Exptd" indicate the expected value for each treatment mixture using the Colby equation.

TABLE C

Observed and Expected Effects of Compound 1 Alone and Mixtures with Amisulbrom and Ametoctradin in Controlling Tomato Late Blight and Cucumber Downy Mildew

| Application Rate (ppm) of Compound 1 | Component | Application Rate (ppm) of Component (b) | Test I | | Test J | |
|---|---|---|---|---|---|---|
| | | | Obsd | Exptd | Obsd | Exptd |
| 0 | — | 0 | 0 | — | 0 | — |
| 0.00001 | — | 0 | 39 | — | 17 | — |
| 0.0001 | — | 0 | 63 | — | 47 | — |
| 0.001 | — | 0 | 72 | — | 40 | — |
| 0.01 | — | 0 | 100 | — | 94 | — |
| 0.1 | — | 0 | 100 | — | 100 | — |
| 0 | amisulbrom | 0.08 | 57 | — | 0 | — |
| 0 | amisulbrom | 0.4 | 52 | — | 0 | — |
| 0 | amisulbrom | 2 | 82 | — | 95 | — |
| 0 | amisulbrom | 10 | 100 | — | 100 | — |
| 0 | amisulbrom | 40 | 100 | — | 100 | — |
| 0.001 | amisulbrom | 0.08 | 46 | 88 | 0 | 40 |
| 0.001 | amisulbrom | 0.4 | 67 | 86 | 0 | 40 |
| 0.001 | amisulbrom | 2 | 80 | 95 | 85 | 97 |
| 0.001 | amisulbrom | 10 | 100 | 100 | 100 | 100 |
| 0.001 | amisulbrom | 40 | 100 | 100 | 100 | 100 |
| 0.01 | amisulbrom | 0.08 | 91 | 100 | 40 | 94 |
| 0.01 | amisulbrom | 0.4 | 99 | 100 | 82 | 94 |
| 0.01 | amisulbrom | 2 | 100 | 100 | 100 | 100 |
| 0.01 | amisulbrom | 10 | 100 | 100 | 100 | 100 |
| 0.01 | amisulbrom | 40 | 100 | 100 | 100 | 100 |
| 0 | ametoctradin | 0.08 | 8 | — | 0 | — |
| 0 | ametoctradin | 0.4 | 23 | — | 0 | — |
| 0 | ametoctradin | 2 | 63 | — | 0 | — |
| 0 | ametoctradin | 10 | 83 | — | 26 | — |
| 0 | ametoctradin | 40 | 83 | — | 95 | — |
| 0.001 | ametoctradin | 0.08 | 8 | 74 | 0 | 40 |
| 0.001 | ametoctradin | 0.4 | 39 | 78 | 0 | 40 |
| 0.001 | ametoctradin | 2 | 63 | 90 | 0 | 40 |
| 0.001 | ametoctradin | 10 | 67 | 95 | 63 | 56 |
| 0.001 | ametoctradin | 40 | 97 | 95 | 96 | 97 |
| 0.01 | ametoctradin | 0.08 | 100 | 100 | 53 | 94 |
| 0.01 | ametoctradin | 0.4 | 90 | 100 | 77 | 94 |
| 0.01 | ametoctradin | 2 | 100 | 100 | 93 | 94 |
| 0.01 | ametoctradin | 10 | 100 | 100 | 97 | 96 |
| 0.01 | ametoctradin | 40 | 100 | 100 | 100 | 100 |

TABLE D

Observed and Expected Effects of Compound 1 Alone and Mixtures with Amisulbrom and Ametoctradin in Controlling Tomato Late Blight

| Application Rate (ppm) of Compound 1 | Component (b) | Application Rate (ppm) of Component (b) | Test I | |
|---|---|---|---|---|
| | | | Obsd | Exptd |
| 0 | — | 0 | 0 | — |
| 0.00001 | — | 0 | 0 | — |
| 0.0001 | — | 0 | 0 | — |
| 0.001 | — | 0 | 80 | — |
| 0.01 | — | 0 | 93 | — |
| 0.1 | — | 0 | 100 | — |
| 0 | amisulbrom | 0.016 | 0 | — |
| 0 | amisulbrom | 0.08 | 9 | — |
| 0 | amisulbrom | 0.4 | 63 | — |
| 0 | amisulbrom | 2 | 85 | — |
| 0 | amisulbrom | 10 | 86 | — |
| 0.0001 | amisulbrom | 0.016 | 0 | 0 |
| 0.0001 | amisulbrom | 0.08 | 50 | 9 |
| 0.0001 | amisulbrom | 0.4 | 40 | 63 |
| 0.0001 | amisulbrom | 2 | 74 | 85 |
| 0.0001 | amisulbrom | 10 | 97 | 86 |
| 0.001 | amisulbrom | 0.016 | 53 | 80 |
| 0.001 | amisulbrom | 0.08 | 9 | 90 |
| 0.001 | amisulbrom | 0.4 | 0 | 88 |
| 0.001 | amisulbrom | 2 | 92 | 95 |

TABLE D-continued

Observed and Expected Effects of Compound 1 Alone and Mixtures with Amisulbrom and Ametoctradin in Controlling Tomato Late Blight

| Application Rate (ppm) of Compound 1 | Component (b) | Application Rate (ppm) of Component (b) | Test I Obsd | Test I Exptd |
|---|---|---|---|---|
| 0.001 | amisulbrom | 10 | 97 | 99 |
| 0 | ametoctradin | 0.08 | 9 | — |
| 0 | ametoctradin | 0.4 | 0 | — |
| 0 | ametoctradin | 2 | 0 | — |
| 0 | ametoctradin | 10 | 94 | — |
| 0 | ametoctradin | 40 | 93 | — |
| 0.0001 | ametoctradin | 0.08 | 24 | 9 |
| 0.0001 | ametoctradin | 0.4 | 47 | 0 |
| 0.0001 | ametoctradin | 2 | 80 | 0 |
| 0.0001 | ametoctradin | 10 | 79 | 94 |
| 0.0001 | ametoctradin | 40 | 87 | 93 |
| 0.001 | ametoctradin | 0.08 | 0 | 85 |
| 0.001 | ametoctradin | 0.4 | 9 | 89 |
| 0.001 | ametoctradin | 2 | 26 | 96 |
| 0.001 | ametoctradin | 10 | 76 | 96 |
| 0.001 | ametoctradin | 40 | 87 | 97 |

TABLE E

Observed and Expected Effects of Compound 1 Alone and Mixtures with Amisulbrom and Ametoctradin in Controlling Tomato Late Blight

| Application Rate (ppm) of Compound 1 | Component (b) | Application Rate (ppm) of Component (b) | Test K Obsd | Test K Exptd |
|---|---|---|---|---|
| 0 | — | 0 | 0 | — |
| 0.001 | — | 0 | 0 | — |
| 0.01 | — | 0 | 17 | — |
| 0.1 | — | 0 | 80 | — |
| 1 | — | 0 | 99 | — |
| 10 | — | 0 | 100 | — |
| 0 | amisulbrom | 0.4 | 0 | — |
| 0 | amisulbrom | 2 | 0 | — |
| 0 | amisulbrom | 10 | 0 | — |
| 0 | amisulbrom | 40 | 0 | — |
| 0 | amisulbrom | 200 | 0 | — |
| 0.01 | amisulbrom | 0.4 | 0 | 17 |
| 0.01 | amisulbrom | 2 | 0 | 17 |
| 0.01 | amisulbrom | 10 | 0 | 17 |
| 0.01 | amisulbrom | 40 | 0 | 17 |
| 0.01 | amisulbrom | 200 | 0 | 17 |
| 0.1 | amisulbrom | 0.4 | 64 | 80 |
| 0.1 | amisulbrom | 2 | 40 | 80 |
| 0.1 | amisulbrom | 10 | 33 | 80 |
| 0.1 | amisulbrom | 40 | 63 | 80 |
| 0.1 | amisulbrom | 200 | 77 | 80 |
| 0 | ametoctradin | 0.4 | 0 | — |
| 0 | ametoctradin | 2 | 0 | — |
| 0 | ametoctradin | 10 | 0 | — |
| 0 | ametoctradin | 40 | 0 | — |
| 0 | ametoctradin | 200 | 0 | — |
| 0.01 | ametoctradin | 0.4 | 0 | 17 |
| 0.01 | ametoctradin | 2 | 0 | 17 |
| 0.01 | ametoctradin | 10 | 0 | 17 |
| 0.01 | ametoctradin | 40 | 0 | 17 |
| 0.01 | ametoctradin | 200 | 0 | 17 |
| 0.1 | ametoctradin | 0.4 | 72 | 80 |
| 0.1 | ametoctradin | 2 | 72 | 80 |
| 0.1 | ametoctradin | 10 | 80 | 80 |
| 0.1 | ametoctradin | 40 | 86 | 80 |
| 0.1 | ametoctradin | 200 | 88 | 80 |

Tables C-E show compositions of the present invention comprising mixtures of Compound 1 with component (b) compounds demonstrating synergistic control of tomato late blight and cucumber downy mildew. As control cannot exceed 100%, the increase above expected fungicidal activity can be greatest when the separate active ingredient components alone are at application rates providing considerably less than 100% control. Synergy may not be evident at low application rates where the individual active ingredient components alone have little activity. However, in some instances greater activity was observed for combinations wherein individual active ingredients alone at the same application rates had essentially no activity. As demonstrated above, this invention provides an advantageous method of combating tomato late blight (*Phytophthora infestans*) and cucumber downy mildew (*Pseudoperonospora cubensis*) diseases.

What is claimed is:

1. A crystalline form of 1-[4-[4-[5-(2,6-difluorophenyl)-4,5-dihydro-3-isoxazolyl]-2-thiazolyl]-1-piperidinyl]-2[5-methyl-3-(trifluoromethyl)-1H-pyrazol-1-yl]ethanone designated Form B having a powder Cu(Kα) X-ray diffraction pattern substantially in accordance with that shown in FIG. 2.

2. The crystalline form of claim 1 characterized by a powder Cu(Kα) X-ray diffraction pattern having at least the 2θ reflection positions 14.902, 18.123, 18.87, 20.204, 20.883, 21.79, 24.186 and 26.947.

3. A method for preparing the crystalline form of claim 1 comprising forming a reaction mixture by contacting 2-bromo-1-[4,5-dihydro-5-(2,6-difluorophenyl)-3-isoxazoly]ethanone and 1-[2-[5-methyl-3-(trifluoromethyl)-1H-pyrazol-1-yl]acetyl]-4-piperidinecarbothioamide in the presence of an alkanol solvent selected from methanol and ethanol, including mixtures thereof; neutralizing the reaction mixture with base; and adding up to 50% water by volume and seed crystals of the crystalline form of claim 1 to the reaction mixture.

4. A method for preparing the crystalline form of claim 1 comprising mixing a crystalline form of 1-[4-[4-[5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone designated Form A having a powder Cu(Kα) X-ray diffraction pattern substantially in accordance with that shown in FIG. 1 with a solvent comprising an alkanol selected from methanol and ethanol, including mixtures thereof, and optionally up to about 30% water by volume to form a slurry; adding seed crystals of the crystalline form of claim 1 to the slurry; and maintaining the slurry while Form A converts to the crystalline form of claim 1.

5. The method of claim 4 wherein the slurry consists essentially of a mixture of 1-[4-[4-[5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone with methanol or with methanol and water, or consists essentially of a mixture of 1-[4-[4-[5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone with ethanol or with ethanol and water.

6. The method of claim 4 wherein the crystalline Form A mixed with the solvent is in admixture with the crystalline form of claim 1.

7. A fungicidal composition comprising (a) a fungicidally effective amount of the the crystalline form as defined by claim 1 and (b) at least one additional component selected from the group consisting of surfactants, solid diluents and liquid carriers.

8. The fungicidal composition of claim 7 comprising a liquid carrier forming a continuous liquid phase in which component (a) is dispersed.

9. The fungicidal composition of claim 8 wherein the liquid carrier forming the continuous liquid phase contains at least about 50% water by weight of the liquid carrier.

10. The fungicidal composition of claim 9 further comprising a water-immiscible liquid component emulsified in the continuous liquid phase.

11. The fungicidal composition of claim 8 wherein the liquid carrier forming the continuous liquid phase is water-immiscible.

12. A method for controlling plant diseases caused by Oomycete fungal plant pathogens comprising applying to a plant or portion thereof, or to a plant seed, a fungicidally effective amount of the crystalline form as defined by claim 1.

* * * * *